(12) United States Patent
Kawasaki et al.

(10) Patent No.: US 8,147,842 B2
(45) Date of Patent: Apr. 3, 2012

(54) MUTANT LUCIFERASE

(75) Inventors: Kosei Kawasaki, Hokkaido (JP); Yousuke Morita, Hokkaido (JP); Satoru Ohgiya, Hokkaido (JP); Yoshihiro Ohmiya, Osaka (JP); Yasushi Ohyama, Hokkaido (JP)

(73) Assignee: National Institute of Advanced Industrial Science and Technology, Tokyo (JP)

( * ) Notice: Subject to any disclaimer, the term of this patent is extended or adjusted under 35 U.S.C. 154(b) by 546 days.

(21) Appl. No.: 12/304,631

(22) PCT Filed: Jan. 26, 2007

(86) PCT No.: PCT/JP2007/051279
§ 371 (c)(1), (2), (4) Date: Dec. 12, 2008

(87) PCT Pub. No.: WO2007/144990
PCT Pub. Date: Dec. 21, 2007

(65) Prior Publication Data
US 2009/0263880 A1 Oct. 22, 2009

(30) Foreign Application Priority Data
Jun. 12, 2006 (JP) .................................. 2006-162662

(51) Int. Cl.
*A61K 39/00* (2006.01)
*C12N 9/02* (2006.01)
*C07H 21/04* (2006.01)

(52) U.S. Cl. .................. 424/192.1; 435/189; 435/252.3; 435/320.1; 536/23.2

(58) Field of Classification Search .................. 435/189, 435/252.3, 320.1; 536/23.2
See application file for complete search history.

(56) References Cited

U.S. PATENT DOCUMENTS
7,871,803 B2 *  1/2011  Takenaka ...................... 435/189

FOREIGN PATENT DOCUMENTS
| JP | 2003512071 A | 4/2003 |
| JP | 2004187652 A | 7/2004 |
| WO | WO9836081 A2 * | 8/1998 |
| WO | 2004022600 A1 | 3/2004 |
| WO | 2004052934 A1 | 6/2004 |

OTHER PUBLICATIONS

Sequence alignment between Accession No. 018560 (1998) and SEQ ID No. 2 of the instant application.*
Sequence alignment between Accession No. AAV41716 and SEQ ID No. 1.*
Yoshihiro Nakajima, et al.; "cDNA Cloning and Characterization of a Secreted Luciferase from the Luminous Japanese Ostracod, *Cypridina noctiluca*"; Biosci. Biotechnol. Biochem.; 2004; pp. 565-570; vol. 68, No. 3.
Vadim Viviani, et al.; "Thr226 is a Key Residue for Bioluminescence Spectra Determination in Beetle Luciferases"; Biochemical and Biophysical Research Communications; 2001; pp. 1286-1291; vol. 280, No. 5.
Morita, Y., "Preparation of mutants of luciferase (CLuc) derived from *Cypridina noctiluca* for improvement of a reporter assay system and biochemical analysis", Abstract, Dept. of Biol. Sci., Faculty of Science, Hokkaido University, Nishi 8-chome, Kita 10-jo, Kita-ku, Sapporo-shi, Hokkaido, Japan, Feb. 3, 2006.
Morita, Y., "Preparation of mutants of luciferase (CLuc) as derived from *Cypridina noctiluca* for improvement of a reporter assay system and biochemical analysis", Power Point Presentation, Faculty of Science, Hokkaido University, Nishi 8-chome, Kita 10-jo, Kita-ku, Sapporo-shi, Hokkaido, Japan, Feb. 10, 2006.

* cited by examiner

*Primary Examiner* — Tekchand Saidha
(74) *Attorney, Agent, or Firm* — Sughrue Mion, PLLC

(57) ABSTRACT

An object of the present invention is to provide a mutant luciferase having luciferase activity with an altered emission spectrum. A specific amino acid residue(s) is substituted in a luciferase derived from *Cypridina noctiluca* and then the resulting mutant luciferase having luciferase activity with an emission spectrum differing from that of the wild-type luciferase is screened for.

10 Claims, 1 Drawing Sheet

MUTANT LUCIFERASE

TECHNICAL FIELD

The present invention relates to a mutant luciferase having luciferase activity with an altered emission spectrum, for example.

BACKGROUND OF THE INVENTION

Reporter assay is a means for quantifying the transcriptional activity of a transcriptional regulatory sequence. Reporter assay is carried out by ligating a gene (hereinafter, referred to as "reporter gene") encoding a reporter protein under the control of a transcriptional regulatory sequence (e.g., promoter and enhancer) to be examined, introducing the resultant into a host cell, and then causing the expression of the protein. At this time, the transcriptional activity of a promoter is positively correlated with the amount of reporter protein generated by transcription and translation, for example. Hence, through quantification of the amount of reporter protein, the degree (high or low) of the relative transcriptional activity of a promoter can be evaluated.

Reporter assay can be carried out using various proteins as reporter proteins. For example, when a fluorescent protein is used as reporter protein, the thus expressed fluorescent protein is irradiated with excitation light and then the thus generated fluorescence intensity is measured, so that the relative amount of the reporter protein can be quantified (this method is referred to as a fluorescence method).

Furthermore, for example, reporter assay can be carried out using an enzyme such as β-galactosidase or alkaline phosphatase as a reporter protein. When an enzyme is used as a reporter protein, the relative amount of the reporter protein can be quantified by colorimetry with the use of a substrate that is degraded by the action of the enzyme so as to generate a color substance (this method is referred to as calorimetric method). Another method involves the use of a substrate that causes the generation of a luminescent substance instead of a substrate that causes the generation of a color substance. In this case, the relative amount of reporter protein can be quantified through measurement of the amount of luminescence (this method is referred to as a luminescent method).

Such a luminescent method has the following excellent characteristics. First, the method does not require any excitation light unlike a fluorescence method, so that the background is small and a high ratio of signal to noise can be obtained. Furthermore, the method has high sensitivity, by which a broad dynamic range can be obtained. Moreover, the method is excellent in terms of quantitative capability.

An example of an enzyme reaction system that is generally used in the luminescent method is a luciferase/luciferin reaction system.

Various types of luciferase are known, and they differ significantly from each other in terms of primary structure. For example, there are various luciferases derived from various organisms, including firefly and *Renilla*.

Meanwhile, various types of luciferins are present as substrates, which differ greatly from each other in terms of chemical structure.

Types of luciferin that each luciferase recognizes as a substrate are limited to some extent. A technique generally referred to as a dual reporter assay involves adding a luciferin derived from firefly (hereinafter, referred to as "firefly luciferin") and a luciferin derived from *Renilla* (hereinafter, referred to as "*Renilla* luciferin") (coelenterazine) successively to a sample solution containing a mixture of a luciferase derived from firefly (hereinafter, referred to as "firefly luciferase") and a luciferase derived from *Renilla* (hereinafter, referred to as "*Renilla* luciferase") and then separately measuring the activity of the firefly luciferase and the activity of the *Renilla* luciferase.

Sea-firefly includes species such as *Vargula hilgendorfii* and *Cypridina noctiluca*. In such species of sea-firefly, luciferase is released ex vivo (specifically, in sea water) and then luciferin reacts with oxygen in sea water because of the catalytic action of the luciferase so as to produce luminescence.

Genes encoding a luciferase derived from *Vargula hilgendorfii* (hereinafter, referred to as "VLuc") and a luciferase derived from *Cypridina noctiluca* (hereinafter, referred to as "CLuc"), respectively, have been cloned (Thompson, E. M., Nagata S., Tsuji F. I., "Proceedings of the National Academy of Sciences of the United States of America," 1989, Vol. 86, p. 6567-6571; and Nakajima, Y., Kobayashi, K., Yamagishi, K., Enomoto, T., Ohmiya, Y., "Bioscience and Biotechnology and Biochemistry," 2004, Vol. 68, p. 565-570). Both VLuc and CLuc are expressed in cultured cells and can be caused to be secreted extracellularly (JP Patent Publication (Kokai) No. 3-30678 A (1991) and International Publication No. 2006/132350 Pamphlet). Specifically, VLuc and CLuc are secretory luciferases. Therefore, such a gene encoding the luciferase (hereinafter, referred to as a "luciferase gene") is used as a reporter gene, and the transcriptional activity of a transcriptional regulatory sequence such as a promoter can be measured without disrupting cells (International Patent Publication No. 2006/132350 Pamphlet).

In the case of secretory luciferases, a culture solution containing a secretory luciferase can be directly used as a solution to be tested. Hence, secretory luciferases are appropriate for construction of, namely, a high-throughput reporter assay system for treatment of many samples. On the other hand, in the case of non-secretory luciferases, collection of cells by centrifugation and disruption (or enhancement of cell permeabilization) of cells by ultrasonication, treatment with a surfactant, treatment with an organic solvent, or the like are essential. These procedures are inappropriate for treatment of numerous samples. Furthermore, in the case of secretory luciferases, a sample for measurement can be obtained by collecting a portion of a culture solution without disrupting cells. Thus, sampling can be carried out consecutively for the same cells. On the other hand, in the case of non-secretory luciferases, cells are always damaged by cell disruption or the like. Hence, consecutive sampling with the use of the same cells is impossible and as many different cells should be prepared as the number of measurement points.

It has been reported that the above CLuc is secreted in a culture solution at a level 320 times greater than VLuc, when expressed in NIH3T3 cells, and 410 times greater than VLuc, when expressed in HeLaS3 cells (Nakajima, Y., Kobayashi, K., Yamagishi, K., Enomoto, T., Ohmiya, Y., "Bioscience and Biotechnology and Biochemistry," 2004, Vol. 68, p. 565-570). Therefore, compared with VLuc, CLuc is appropriate for use in a high-sensitivity, high-throughput reporter assay system using cultured cells as hosts.

Furthermore, a secretory high-throughput reporter assay system using a budding yeast *Saccharomyces cerevisiae* into which a CLuc gene has been introduced has also been conceived (International Publication No. 2006/132350 Pamphlet).

The luminescence mechanism of a luciferase/luciferin reaction system is generally considered to be as follows. First, luciferin is oxidized by catalytic action of luciferase into oxyluciferin in its excited state. Subsequently, oxyluciferin in its excited state immediately returns to the ground state, during which the oxyluciferin releases energy in the form of light (produces luminescence). The amount of luminescence produced per unit of time is thought to be proportional to the amount of luciferase existing in the system. Thus, the relative amount of luciferase can be quantified based on the luminescence.

With the above luminescence mechanism, luminescence can be obtained in accordance with the difference in energy level between the excited state and the ground state of oxyluciferin. A change in energy level difference appears as an emission spectrum change. Specifically, when the energy level in the excited state changes for some reason upon production of luminescence, luminescence with a color differing from that of a general case is obtained. This effect is known to take place due to a significant difference or a local difference in terms of the primary structure of luciferase (Viviani, V., Uchida, A., Suenaga, N., Ryufuku, M., Ohmiya, Y., "Biochemistry and Biophysics Research Communication," 2001, Vol. 280, p. 1286-1291).

Meanwhile, there are at least two methods (referred to as "multi-reporter assay") for simultaneously carrying out reporter assays of 2 or more types of promoter activity using a luciferase gene as a reporter gene, as follows.

A first method involves the use of a plurality of different chemical species of luciferins and luciferases having substrate specificity for each luciferin. In the case of this method, no reaction takes place with combinations other than the combination of a luciferase and a luciferin that form a pair, because of differences in substrate specificity. Furthermore, appropriate conditions (e.g., compositions of reaction solutions and hydrogen ion concentrations) differ depending on the reaction of each luciferase/luciferin reaction system. In the case of this method, reaction conditions should be varied depending on each luciferase/luciferin reaction, for one specimen, and the reactions should be carried out in order or in parallel. In accordance therewith, multiple luminescence measurements should be carried out for one specimen by employing different conditions appropriate for each luciferase/luciferin reaction. As described above, this method is problematic in terms of its complicated measurement procedures.

A second method involves the use of luciferins of the same chemical species as substrates. In this case, multiple types of luciferase whose substrates are luciferins of the same chemical species are used as reporter proteins. The amino acid sequences of these luciferases partially differ from each other, and they are characterized in that different emission spectra are generated from luciferases. The luminescence intensity originating from each luciferase should be determined and quantified based on differences in spectrum.

A multi-reporter assay using the above second method has the advantage of being simple because only a single type of substrate is used, and because the luminous reaction and the measurement can each be completed at one time.

In the case of luminescence simultaneously produced from luciferases with different luminescent colors, the spectra thereof may overlap. However, even under such circumstances, a method for estimating the luminescence intensity originating from each luciferase has been conceived (JP Patent Publication (Kokai) No. 2004-333457 A).

An example of a multi-reporter assay using the principle of the above second method is a method that involves the use of a luciferase gene derived from a luminescent beetle and a mutant gene thereof (Yoshihiro Nakajima and Yoshihiro Ohmiya, "Biotechnology Journal," 2006, Vol. 6, No. 2, p. 230-232). However, such a luciferase derived from a luminescent beetle is non-secretory. Therefore, the luciferase is inappropriate for use in high-throughput reporter assays for the reasons as described above.

As described above, no high-throughput multi-reporter assay using the principle of the above second method is currently known. Furthermore, concerning sea-firefly luciferase, the presence of any mutant luciferase that alters luminescent color is unknown.

Meanwhile, a phenomenon referred to as BRET (Bioluminescence resonance energy transfer) is used as a method for detecting the structural changes of proteins at the biochemical level or the cellular level, for example (Otsuji, T., Okuda-Ashitaka, E., Kojima, S., Akiyama, H., Ito, S., Ohmiya, Y., "Analytical Biochemistry," 2004, Vol. 329, p. 230-237).

In BRET, a luminous object and a fluorescing object form a pair. As a luminous object, a bioluminescent substance such as luciferase, luciferin, or the like is used. On the other hand, as a fluorescing object, for example, a chemical substance producing fluorescence or a fluorescent protein such as a green fluorescent protein (GFP) is used. When a luminous object and a fluorescing object are located at positions that enable (in terms of distance) topological energy transfer, the luminous object is excited and the energy released when it returns to the ground state is transferred to the fluorescing object. Subsequently the fluorescing object is excited and it emits light when it returns to the ground state. Each fluorescing object has its unique excitation spectrum and excitation efficiency is known to depend on the emission spectrum of the luminous object and the excitation spectrum of the fluorescing object. A luminous object emitting light at a wavelength that efficiently excites a fluorescing object is most preferable for composing an efficient BRET pair.

Hence, luciferase to be used in BRET analysis using luciferase and luciferin as luminous objects preferably emits light at a wavelength that efficiently excites the fluorescing object, with reference to the excitation spectrum of a fluorescing object to be used in the form of a pair. Therefore, the presence of mutant luciferases emitting light at different wavelengths makes it possible to form BRET pairs appropriate for various fluorescing objects.

DISCLOSURE OF THE INVENTION

Object to be Achieved by the Invention

In view of the above circumstances, an object of the present invention is to provide a mutant luciferase having luciferase activity with an altered emission spectrum.

Means to Achieve the Object

As a result of intensive studies to achieve the above object, it has been found that a specific amino acid residue can be substituted in luciferase (CLuc) derived from *Cypridina noctiluca*, so that a mutant luciferase having luciferase activity that exhibits an emission spectrum differing from that of a wild-type luciferase can be obtained. Thus, the present invention has been completed.

The present invention encompasses the following (1) to (34).

(1) A mutant luciferase consisting of any one of the following proteins (a) to (d):

(a) a protein consisting of an amino acid sequence that has, with respect to the amino acid sequence shown in SEQ ID NO: 2, a substitution of lysine at position 375 with another amino acid;

(b) a protein consisting of an amino acid sequence that has, with respect to the amino acid sequence of (a) above, a deletion, a substitution, or an addition of one or several amino acids at positions other than position 375 of such amino acid and having luciferase activity with an emission spectral peak of 457 nm or more;

(c) a protein consisting of an amino acid sequence that has, with respect to the amino acid sequence shown in SEQ ID NO: 2, a deletion of amino acids at positions 1 to 18 and a substitution of lysine at position 375 with another amino acid; and (d) a protein consisting of an amino acid sequence that has, with respect to the amino acid sequence of (c) above, a deletion, a substitution, or an addition of one or several amino acids at positions other than position 375 of such amino acid and having luciferase activity with an emission spectral peak of 457 nm or more.

(2) The mutant luciferase according to (1), wherein lysine at position 375 is substituted with an amino acid selected from the group consisting of alanine, cysteine, aspartic acid, glutamic acid, phenylalanine, glycine, histidine, isoleucine, leucine, methionine, asparagine, proline, glutamine, arginine, serine, threonine, valine, tryptophan, and tyrosine.

(3) The mutant luciferase according to (1), wherein the emission spectral peak ranges from 457 nm to 490 nm.

(4) A mutant luciferase consisting of any one of the following proteins (a) to (d):

(a) a protein consisting of an amino acid sequence that has, with respect to the amino acid sequence shown in SEQ ID NO: 2, a substitution of methionine at position 178 with another amino acid;

(b) a protein consisting of an amino acid sequence that has, with respect to the amino acid sequence of (a) above, a deletion, a substitution, or an addition of one or several amino acids at positions other than position 178 of such amino acid and having luciferase activity with an emission spectral peak of 449 nm or less;

(c) a protein consisting of an amino acid sequence that has, with respect to the amino acid sequence shown in SEQ ID NO: 2, a deletion of amino acids at positions 1 to 18 and a substitution of methionine at position 178 with another amino acid; and (d) a protein consisting of an amino acid sequence that has, with respect to the amino acid sequence of (c) above, a deletion, a substitution, or an addition of one or several amino acids at positions other than position 178 of such amino acid and having luciferase activity with an emission spectral peak of 449 nm or less.

(5) The mutant luciferase according to (4), which has the substitution of methionine at position 178 with lysine.

(6) The mutant luciferase according to (4), wherein the emission spectral peak ranges from 420 nm to 449 nm.

(7) A mutant luciferase consisting of any one of the following proteins (a) to (d):

(a) a protein consisting of an amino acid sequence that has, with respect to the amino acid sequence shown in SEQ ID NO: 2, a substitution of threonine at position 167 with another amino acid;

(b) a protein consisting of an amino acid sequence that has, with respect to the amino acid sequence of (a) above, a deletion, a substitution, or an addition of one or several amino acids at positions other than position 167 of such amino acid and having luciferase activity with an emission spectral peak of 458 nm or more;

(c) a protein consisting of an amino acid sequence that has, with respect to the amino acid sequence shown in SEQ ID NO: 2, a deletion of amino acids at positions 1 to 18 and a substitution of threonine at position 167 with another amino acid; and (d) a protein consisting of an amino acid sequence that has, with respect to the amino acid sequence of (c) above, a deletion, a substitution, or an addition of one or several amino acids at positions other than position 167 of such amino acid and having luciferase activity with an emission spectral peak of 458 nm or more.

(8) The mutant luciferase according to (7), which has the substitution of threonine at position 167 with lysine.

(9) The mutant luciferase according to (7), wherein the emission spectral peak ranges from 458 nm to 490 nm.

(10) A mutant luciferase consisting of any one of the following proteins (a) to (d):

(a) a protein consisting of an amino acid sequence that has, with respect to the amino acid sequence shown in SEQ ID NO: 2, a substitution of asparagine at position 404 with another amino acid;

(b) a protein consisting of an amino acid sequence that has, with respect to the amino acid sequence of (a) above, a deletion, a substitution, or an addition of one or several amino acids at positions other than position 404 of such amino acid and having luciferase activity with an emission spectral peak of 458 nm or more;

(c) a protein consisting of an amino acid sequence that has, with respect to the amino acid sequence shown in SEQ ID NO: 2, a deletion of amino acids at positions 1 to 18 and a substitution of asparagine at position 404 with another amino acid; and (d) a protein consisting of an amino acid sequence that has, with respect to the amino acid sequence of (c) above, a deletion, a substitution, or an addition of one or several amino acids at positions other than position 404 of such amino acid and having luciferase activity with an emission spectral peak of 458 nm or more.

(11) The mutant luciferase according to (10), which has the substitution of asparagine at position 404 with glycine or serine.

(12) The mutant luciferase according to (10), wherein the emission spectral peak ranges from 458 nm to 490 nm.

(13) A mutant luciferase consisting of any one of the following proteins (a) to (d):

(a) a protein consisting of an amino acid sequence that has, with respect to the amino acid sequence shown in SEQ ID NO: 2, a substitution of threonine at position 405 with another amino acid;

(b) a protein consisting of an amino acid sequence that has, with respect to the amino acid sequence of (a) above, a deletion, a substitution, or an addition of one or several amino acids at positions other than position 405 of such amino acid and having luciferase activity with an emission spectral peak of 457 nm or more;

(c) a protein consisting of an amino acid sequence that has, with respect to the amino acid sequence shown in SEQ ID NO: 2, a deletion of amino acids at positions 1 to 18 and a substitution of threonine at position 405 with another amino acid; and (d) a protein consisting of an amino acid sequence that has, with respect to the amino acid sequence of (c) above, a deletion, a substitution, or an addition of one or several amino acids at positions other than position 405 of such amino acid and having luciferase activity with an emission spectral peak of 457 nm or more.

(14) The mutant luciferase according to (13), which has the substitution of threonine at position 405 with isoleucine or methionine.

(15) The mutant luciferase according to (13), wherein the emission spectral peak ranges from 457 nm to 490 nm.

(16) A mutant luciferase consisting of any one of the following proteins (a) to (d):

(a) a protein consisting of an amino acid sequence that has, with respect to the amino acid sequence shown in SEQ ID NO: 2, a substitution of serine at position 406 with another amino acid;

(b) a protein consisting of an amino acid sequence that has, with respect to the amino acid sequence of (a) above, a deletion, a substitution, or an addition of one or several amino acids at positions other than position 406 of such amino acid and having luciferase activity with an emission spectral peak of 460 nm or more;

(c) a protein consisting of an amino acid sequence that has, with respect to the amino acid sequence shown in SEQ ID NO: 2, a deletion of amino acids at positions 1 to 18 and a substitution of serine at position 406 with another amino acid; and (d) a protein consisting of an amino acid sequence that has, with respect to the amino acid sequence of (c) above, a deletion, a substitution, or an addition of one or several amino acids at positions other than position 406 of such amino acid and having luciferase activity with an emission spectral peak of 460 nm or more.

(17) The mutant luciferase according to (16), which has the substitution of serine at position 406 with leucine.

(18) The mutant luciferase according to (16), wherein the emission spectral peak ranges from 460 nm to 490 nm.

(19) A mutant luciferase consisting of any one of the following proteins (a) to (d):

(a) a protein consisting of an amino acid sequence that has, with respect to the amino acid sequence shown in SEQ ID NO: 2, a substitution of isoleucine at position 407 with another amino acid;

(b) a protein consisting of an amino acid sequence that has, with respect to the amino acid sequence of (a) above, a deletion, a substitution, or an addition of one or several amino acids at positions other than position 407 of such amino acid and having luciferase activity with an emission spectral peak of 460 nm or more;

(c) a protein consisting of an amino acid sequence that has, with respect to the amino acid sequence shown in SEQ ID NO: 2, a deletion of amino acids at positions 1 to 18 and a substitution of isoleucine at position 407 with another amino acid; and (d) a protein consisting of an amino acid sequence that has, with respect to the amino acid sequence of (c) above, a deletion, a substitution, or an addition of one or several amino acids at positions other than position 407 of such amino acid and having luciferase activity with an emission spectral peak of 460 nm or more.

(20) The mutant luciferase according to (19), which has the substitution of isoleucine at position 407 with alanine.

(21) The mutant luciferase according to (19), wherein the emission spectral peak ranges from 460 nm to 490 nm.

(22) A mutant luciferase consisting of any one of the following proteins (a) to (d):

(a) a protein consisting of an amino acid sequence that has, with respect to amino acid sequence shown in SEQ ID NO: 2, substitutions of leucine at position 191, glutamine at position 235, tyrosine at position 280, arginine at position 372, glutamine at position 403, asparagine at position 404, and threonine at position 405 with other amino acids;

(b) a protein consisting of an amino acid sequence that has, with respect to the amino acid sequence of (a) above, a deletion, a substitution, or an addition of one or several amino acids at positions other than the positions of such amino acids and having luciferase activity with an emission spectral peak of 466 nm or more;

(c) a protein consisting of an amino acid sequence that has, with respect to the amino acid sequence shown in SEQ ID NO: 2, a deletion of amino acids at positions 1 to 18 and substitutions of leucine at position 191, glutamine at position 235, tyrosine at position 280, arginine at position 372, glutamine at position 403, asparagine at position 404, and threonine at position 405 with other amino acids; and (d) a protein consisting of an amino acid sequence that has, with respect to the amino acid sequence of (c) above, a deletion, a substitution, or an addition of one or several amino acids at positions other than the positions of such amino acids and having luciferase activity with an emission spectral peak of 466 nm or more.

(23) The mutant luciferase according to (22), containing the following amino acid substitutions (A) to (G):

(A) a substitution of leucine at position 191 with glutamine;
(B) a substitution of glutamine at position 235 with arginine;
(C) a substitution of tyrosine at position 280 with aspartic acid;
(D) a substitution of arginine at position 372 with leucine;
(E) a substitution of glutamine at position 403 with proline;
(F) a substitution of asparagine at position 404 with glycine; and
(G) a substitution of threonine at position 405 with methionine.

(24) The mutant luciferase according to (22), wherein the emission spectral peak ranges from 466 nm to 490 nm.

(25) A mutant luciferase consisting of any one of the following proteins (a) to (d):

(a) a protein consisting of an amino acid sequence that has, with respect to the amino acid sequence shown in SEQ ID NO: 2, substitutions of methionine at position 178, leucine at position 191, tyrosine at position 280, arginine at position 372, glutamine at position 403, asparagine at position 404, and threonine at position 405 with other amino acids;

(b) a protein consisting of an amino acid sequence that has, with respect to the amino acid sequence of (a) above, a deletion, a substitution, or an addition of one or several amino acids at positions other than the positions of such amino acids and having luciferase activity with an emission spectral peak of 435 nm or less;

(c) a protein consisting of an amino acid sequence that has, with respect to the amino acid sequence shown in SEQ ID NO: 2, a deletion of amino acids at positions 1 to 18 and substitutions of methionine at position 178, leucine at position 191, tyrosine at position 280, arginine at position 372, glutamine at position 403, asparagine at position 404, and threonine at position 405 with other amino acids; and (d) a protein consisting of an amino acid sequence that has, with respect to the amino acid sequence of (c) above, a deletion, a substitution, or an addition of one or several amino acids at positions other than the positions of such amino acids and having luciferase activity with an emission spectral peak of 435 nm or less.

(26) The mutant luciferase according to (25), containing the following amino acid substitutions (A) to (G):

(A) a substitution of methionine at position 178 with arginine;
(B) a substitution of leucine at position 191 with glutamine;
(C) a substitution of tyrosine at position 280 with aspartic acid;
(D) a substitution of arginine at position 372 with leucine;
(E) a substitution of glutamine at position 403 with proline;
(F) a substitution of asparagine at position 404 with glycine; and (G) a substitution of threonine at position 405 with methionine.

(27) The mutant luciferase according to (25), wherein the emission spectral peak ranges from 420 nm to 435 nm.

(28) A fusion protein, wherein a foreign protein or peptide is linked to the mutant luciferase according to any one of (1) to (27).

(29) A gene encoding the mutant luciferase according to any one of (1) to (27) or the fusion protein according to (28).

(30) A recombinant vector containing the gene according to (29).

(31) A transformant having the recombinant vector according to (30).

(32) The transformant according to (31), wherein two or more genes selected from the group consisting of the gene according to (29) and the genes encoding luciferases or fusion protein consisting of the following proteins (a) to (c) are each placed under the control of different promoters:

(a) a protein consisting of the amino acid sequence shown in SEQ ID NO: 2;

(b) a protein consisting of an amino acid sequence that has, with respect to the amino acid sequence shown in SEQ ID NO: 2, a deletion of amino acids at positions 1 to 18; and (c) a fusion protein in which a foreign protein or peptide is linked to the protein (a) or (b).

(33) A method for evaluating the transcriptional activity of a promoter, comprising a step of causing a culture or a culture supernatant of the transformant according to (32) to come into contact with a luciferin or a derivative thereof and a step of measuring the luminescence intensity of the emission spectrum based on the activity of each luciferase, wherein the transcriptional activity of 2 or more promoters is evaluated.

(34) A method for emitting light or a method for releasing energy, comprising a step of causing the mutant luciferase according to any one of (1) to (27) or the fusion protein according to (28) to come into contact with a luciferin or a derivative thereof and a step of causing an oxyluciferin or a derivative thereof in its excited state to act on a chemical substance, wherein light emission or energy release is caused based on excitation of the chemical substance.

Effects of the Invention

According to the present invention, a mutant luciferase having luciferase activity resulting in an emission spectrum differing from that of a wild-type luciferase can be provided. Furthermore, with the use of the mutant luciferase according to the present invention, a simple and highly sensitive multireporter assay system can be provided. Moreover, upon BRET analysis, the mutant luciferase according to the present invention can be an excellent energy donor.

The present specification includes part or all of the contents as disclosed in the specification and/or drawing of Japanese Patent Application No. 2006-162662, which is a priority document of the present application.

PREFERRED EMBODIMENTS OF THE INVENTION

Figure 1:
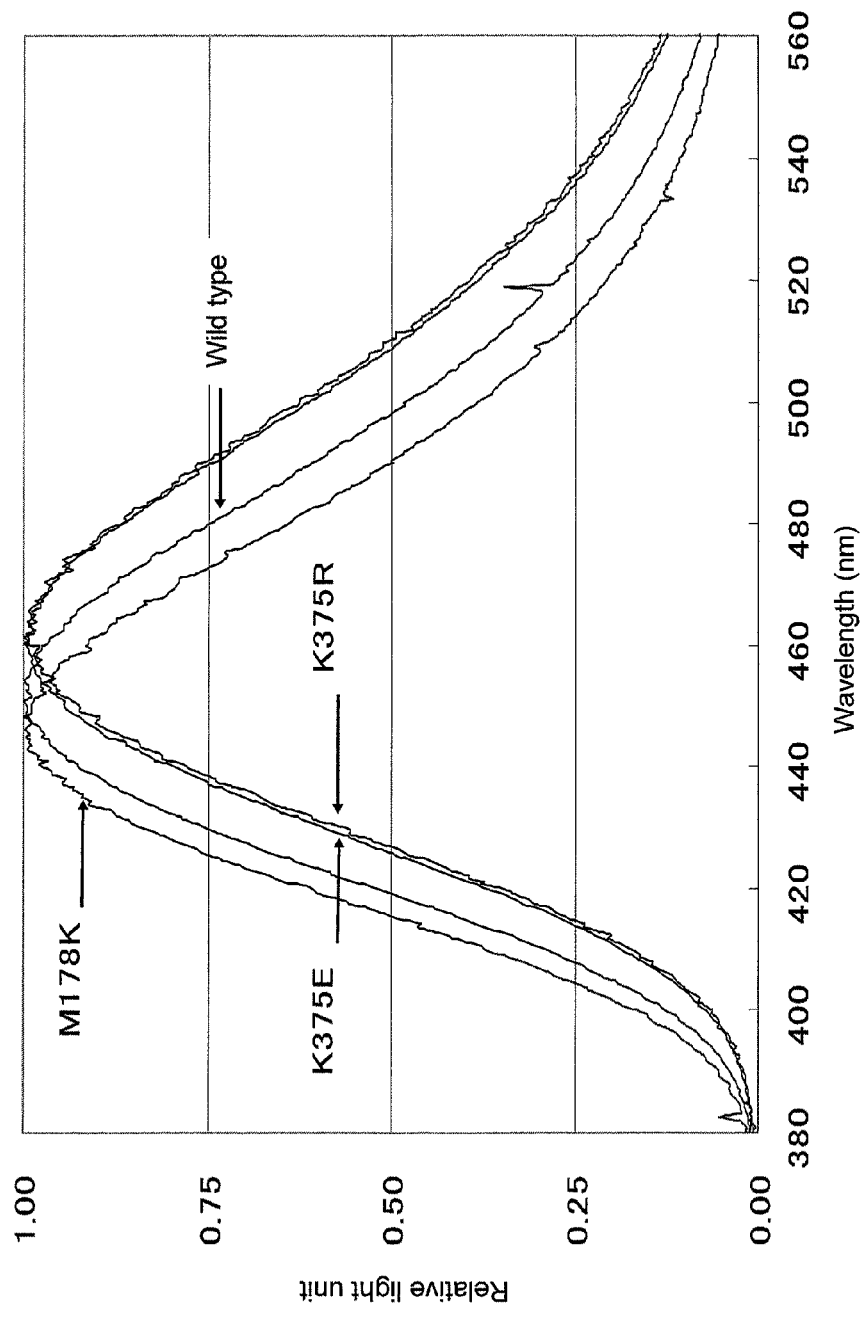
FIG. 1 shows the relative luminescence intensity (or relative light unit) to wavelength of each luciferase.

Hereinafter, the present invention will be described in more detail.

A 1$^{st}$ mutant luciferase according to the present invention is any one of the following proteins (a) to (d) (hereinafter, referred to as "the 1$^{st}$ mutant luciferase(s)"):

(a) a protein consisting of an amino acid sequence that has, with respect to the amino acid sequence shown in SEQ ID NO: 2, a substitution of lysine at position 375 with another amino acid;

(b) a protein consisting of an amino acid sequence that has, with respect to the amino acid sequence of (a) above, a deletion, a substitution, or an addition of one or several amino acids at positions other than position 375 of such amino acid and having luciferase activity with an emission spectral peak of 457 nm or more;

(c) a protein consisting of an amino acid sequence that has, with respect to the amino acid sequence shown in SEQ ID NO: 2, a deletion of amino acids at positions 1 to 18 and a substitution of lysine at position 375 with another amino acid; and (d) a protein consisting of an amino acid sequence that has, with respect to the amino acid sequence of (c) above, a deletion, a substitution, or an addition of one or several amino acids at positions other than position 375 of such amino acid and having luciferase activity with an emission spectral peak of 457 nm or more.

The protein consisting of the amino acid sequence shown in SEQ ID NO: 2 is a luciferase (CLuc) derived from *Cypridina noctiluca*. Furthermore, the nucleotide sequence shown in SEQ ID NO: 1 is a gene (cDNA) encoding CLuc.

The mutant luciferase according to (a) above among the 1$^{st}$ mutant luciferases is a protein consisting of an amino acid sequence that has, with respect to the amino acid sequence of CLuc, a substitution of lysine at position 375 with another amino acid. This protein exerts luciferase activity similarly to that of CLuc. However, because of the amino acid substitution, the protein is characterized by the emission spectral peak of 457 nm or more and particularly the emission spectral peak ranging from 457 nm to 490 nm (e.g., 457 nm to 463 nm) when luminescence is produced upon luciferin oxidation by the luciferase activity, whereas the same of CLuc is 454 nm. Here, "another amino acid" may be any amino acid other than lysine.

Meanwhile, the mutant luciferase according to (b) above among the 1$^{st}$ mutant luciferases consists of an amino acid sequence that has, with respect to the mutant luciferase according to (a), a deletion, a substitution, or an addition of one or several (e.g., 1 to 10, preferably 1 to 5, and particularly preferably 1 to 3) amino acids at positions other than position 375 of such amino acid and has luciferase activity with an emission spectral peak of 457 nm or more. Examples of the positions other than position 375 of the amino acid include threonine at position 167, glutamine at position 403, asparagine at position 404, threonine at position 405, serine at position 406, and isoleucine at position 407.

Furthermore, the mutant luciferase according to (c) above among the 1$^{st}$ mutant luciferases is a mature protein in which a secretory signal peptide (consisting of an amino acid sequence ranging from amino acids at positions 1 to 18 of the amino acid sequence shown in SEQ ID NO: 2) of CLuc has been removed from the amino acid sequence of the mutant luciferase according to (a). In general, secretory proteins including CLuc are synthesized in the forms of precursors each having a secretory signal peptide on the N-terminus. Such a precursor is cleaved with a signal peptidase during a transmembrane process to be a mature protein. In the present invention, the term "mature protein" refers to a protein that is secreted outside the cell membranes or cell walls.

Furthermore, the mutant luciferase according to (d) above among the 1st mutant luciferases is a mature protein in which a secretory signal peptide of CLuc has been removed from the amino acid sequence of the mutant luciferase according to (b).

Meanwhile, a 2nd mutant luciferase according to the present invention is any one of the following proteins (a) to (d) (hereinafter, referred to as "the 2nd mutant luciferase(s)"):

(a) a protein consisting of an amino acid sequence that has, with respect to the amino acid sequence shown in SEQ ID NO: 2, a substitution of methionine at position 178 with another amino acid;

(b) a protein consisting of an amino acid sequence that has, with respect to the amino acid sequence of (a) above, a deletion, a substitution, or an addition of one or several amino acids at positions other than position 178 of such amino acid and having luciferase activity with an emission spectral peak of 449 nm or less;

(c) a protein consisting of an amino acid sequence that has, with respect to the amino acid sequence shown in SEQ ID NO: 2, a deletion of amino acids at positions 1 to 18 and a substitution of methionine at position 178 with another amino acid; and (d) a protein consisting of an amino acid sequence that has, with respect to the amino acid sequence of (c) above, a deletion, a substitution, or an addition of one or several amino acids at positions other than position 178 of such amino acid and having luciferase activity with an emission spectral peak of 449 nm or less.

The mutant luciferase according to (a) above among the 2nd mutant luciferases is a protein consisting of an amino acid sequence that has, with respect to the amino acid sequence of CLuc, a substitution of methionine at position 178 with another amino acid. This protein exerts luciferase activity similarly to that of CLuc. However, because of the amino acid substitution, the protein is characterized by the emission spectral peak of 449 nm or less and particularly the emission spectral peak ranging from 420 nm to 449 nm (e.g., 447 nm to 449 nm) when luminescence is produced upon luciferin oxidation by the luciferase activity, whereas the same of CLuc is 454 nm. Here, "another amino acid" may be any amino acid other than methionine and is particularly desirably lysine.

Meanwhile, the mutant luciferase according to (b) above among the 2nd mutant luciferases consists of an amino acid sequence that has, with respect to the mutant luciferase according to (a), a deletion, a substitution, or an addition of one or several (e.g., 1 to 10, preferably 1 to 5, and particularly preferably 1 to 3) amino acids at positions other than position 178 of such amino acid and has luciferase activity with an emission spectral peak of 449 nm or less. An example of the positions other than position 178 of the amino acid is leucine at position 197.

Furthermore, the mutant luciferase according to (c) above among the 2nd mutant luciferases is a mature protein in which a secretory signal peptide of CLuc has been removed from the amino acid sequence of the mutant luciferase according to (a).

Furthermore, the mutant luciferase according to (d) above among the 2nd mutant luciferases is a mature protein in which a secretory signal peptide of CLuc has been removed from the amino acid sequence of the mutant luciferase according to (b).

Meanwhile, a 3rd mutant luciferase according to the present invention is any one of the following proteins (a) to (d) (hereinafter, referred to as "the 3rd mutant luciferase(s)"):

(a) a protein consisting of an amino acid sequence that has, with respect to the amino acid sequence shown in SEQ ID NO: 2, a substitution of threonine at position 167 with another amino acid;

(b) a protein consisting of an amino acid sequence that has, with respect to the amino acid sequence of (a) above, a deletion, a substitution, or an addition of one or several amino acids at positions other than position 167 of such amino acid and having luciferase activity with an emission spectral peak of 458 nm or more;

(c) a protein consisting of an amino acid sequence that has, with respect to the amino acid sequence shown in SEQ ID NO: 2, a deletion of amino acids at positions 1 to 18 and a substitution of threonine at position 167 with another amino acid; and (d) a protein consisting of an amino acid sequence that has, with respect to the amino acid sequence of (c) above, a deletion, a substitution, or an addition of one or several amino acids at positions other than position 167 of such amino acid and having luciferase activity with an emission spectral peak of 458 nm or more.

The mutant luciferase according to (a) above among the 3rd mutant luciferases is a protein consisting of an amino acid sequence that has, with respect to the amino acid sequence of CLuc, a substitution of threonine at position 167 with another amino acid. This protein exerts luciferase activity similarly to that of CLuc. However, because of the amino acid substitution, the protein is characterized by the emission spectral peak of 458 nm or more and particularly the emission spectral peak ranging from 458 nm to 490 nm (e.g., 458 nm to 460 nm) when luminescence is produced upon luciferin oxidation by the luciferase activity, whereas the same of CLuc is 454 nm. Here, "another amino acid" may be any amino acid other than threonine and examples of which include isoleucine, leucine, and lysine and is particularly desirably isoleucine or lysine.

Meanwhile, the mutant luciferase according to (b) above among the 3rd mutant luciferases consists of an amino acid sequence that has, with respect to the mutant luciferase according to (a), a deletion, a substitution, or an addition of one or several (e.g., 1 to 10, preferably 1 to 5, and particularly preferably 1 to 3) amino acids at positions other than position 167 of the amino acid and has luciferase activity with an emission spectral peak of 458 nm or more. Examples of the positions other than position 167 of the amino acid include lysine at position 375, glutamine at position 403, asparagine at position 404, threonine at position 405, serine at position 406, and isoleucine at position 407.

Furthermore, the mutant luciferase according to (c) above among the 3rd mutant luciferases is a mature protein in which a secretory signal peptide of CLuc has been removed from the amino acid sequence of the mutant luciferase according to (a).

Furthermore, the mutant luciferase according to (d) above among the 3rd mutant luciferases is a mature protein in which a secretory signal peptide of CLuc has been removed from the amino acid sequence of the mutant luciferase according to (b).

Meanwhile, a 4 h mutant luciferase according to the present invention is any one of the following proteins (a) to (d) (hereinafter, referred to as "the 4th mutant luciferase(s)"):

(a) a protein consisting of an amino acid sequence that has, with respect to the amino acid sequence shown in SEQ ID NO: 2, a substitution of asparagine at position 404 with another amino acid;

(b) a protein consisting of an amino acid sequence that has, with respect to the amino acid sequence of (a) above, a deletion, a substitution, or an addition of one or several amino acids at positions other than position 404 of such amino acid and having luciferase activity with an emission spectral peak of 458 nm or more;

(c) a protein consisting of an amino acid sequence that has, with respect to the amino acid sequence shown in SEQ ID NO: 2, a deletion of amino acids at positions 1 to 18 and a substitution of asparagine at position 404 with another amino acid; and (d) a protein consisting of an amino acid sequence that has, with respect to the amino acid sequence of (c) above, a deletion, a substitution, or an addition of one or several amino acids at positions other than position 404 of such amino acid and having luciferase activity with an emission spectral peak of 458 nm or more.

The mutant luciferase according to (a) above among the $4^{th}$ mutant luciferases is a protein consisting of an amino acid sequence that has, with respect to the amino acid sequence of CLuc, a substitution of asparagine at position 404 with another amino acid. This protein exerts luciferase activity similarly to that of CLuc. However, because of the amino acid substitution, the protein is characterized by the emission spectral peak of 458 nm or more and particularly the emission spectral peak ranging from 458 nm to 490 nm (e.g., 458 nm to 460 nm) when luminescence is produced upon luciferin oxidation by the luciferase activity, whereas the same of CLuc is 454 nm. Here, "another amino acid" may be any amino acid other than asparagine. Examples of such amino acid include glycine, alanine, serine, and threonine and a particularly desirable example thereof is glycine or serine.

Meanwhile, the mutant luciferase according to (b) above among the $4^{th}$ mutant luciferases consists of an amino acid sequence that has, with respect to the mutant luciferase according to (a), a deletion, a substitution, or an addition of one or several (e.g., 1 to 10, preferably 1 to 5, and particularly preferably 1 to 3) amino acids at positions other than position 404 of the above amino acid and has luciferase activity with an emission spectral peak of 458 nm or more. Examples of the positions other than position 404 of the amino acid include lysine at position 38, serine at position 45, valine at position 75, arginine at position 79, arginine at position 87, aspartic acid at position 112, lysine at position 126, threonine at position 167, glutamic acid at position 170, leucine at position 191, methionine at position 223, glutamine at position 235, valine at position 258, isoleucine at position 276, tyrosine at position 280, methionine at position 291, threonine at position 313, arginine at position 372, lysine at position 375, glutamine at position 403, threonine at position 405, serine at position 406, isoleucine at position 407, and glutamic acid at position 479.

Furthermore, the mutant luciferase according to (c) above among the $4^{th}$ mutant luciferases is a mature protein in which a secretory signal peptide of CLuc has been removed from the amino acid sequence of the mutant luciferase according to (a).

Furthermore, the mutant luciferase according to (d) above among the $4^{th}$ mutant luciferases is a mature protein in which a secretory signal peptide of CLuc has been removed from the amino acid sequence of the mutant luciferase according to (b).

Meanwhile, a $5^{th}$ mutant luciferase according to the present invention is any one of the following proteins (a) to (d) (hereinafter, referred to as "the $5^{th}$ mutant luciferase(s)"):

(a) a protein consisting of an amino acid sequence that has, with respect to the amino acid sequence shown in SEQ ID NO: 2, a substitution of threonine at position 405 with another amino acid;

(b) a protein consisting of an amino acid sequence that has, with respect to the amino acid sequence of (a) above, a deletion, a substitution, or an addition of one or several amino acids at positions other than position 405 of such amino acid and having luciferase activity with an emission spectral peak of 457 nm or more;

(c) a protein consisting of an amino acid sequence that has, with respect to the amino acid sequence shown in SEQ ID NO: 2, a deletion of amino acids at positions 1 to 18 and a substitution of threonine at position 405 with another amino acid; and (d) a protein consisting of an amino acid sequence that has, with respect to the amino acid sequence of (c) above, a deletion, a substitution, or an addition of one or several amino acids at positions other than position 405 of such amino acid and having luciferase activity with an emission spectral peak of 457 nm or more.

The mutant luciferase according to (a) above among the $5^{th}$ mutant luciferases is a protein consisting of an amino acid sequence that has, with respect to the amino acid sequence of CLuc, a substitution of threonine at position 405 with another amino acid. This protein exerts luciferase activity similarly to that of CLuc. However, because of the amino acid substitution, the protein is characterized by the emission spectral peak of 457 nm or more and particularly the emission spectral peak ranging from 457 nm to 490 nm (e.g., 457 nm to 460 nm) when luminescence is produced upon luciferin oxidation by the luciferase activity, whereas the same of CLuc is 454 nm. Here, "another amino acid" may be any amino acid other than threonine. Examples of such amino acid include isoleucine, methionine, and leucine and a particularly desirable example thereof is isoleucine or methionine.

Meanwhile, the mutant luciferase according to (b) above among the $5^{th}$ mutant luciferases consists of an amino acid sequence that has, with respect to the mutant luciferase according to (a), a deletion, a substitution, or an addition of one or several (e.g., 1 to 10, preferably 1 to 5, and particularly preferably 1 to 3) amino acids at positions other than position 405 of the above amino acid and has luciferase activity with an emission spectral peak of 457 nm or more. Examples of the positions other than position 405 of the amino acid include lysine at position 38, serine at position 45, valine at position 75, arginine at position 79, arginine at position 87, aspartic acid at position 112, lysine at position 126, threonine at position 167, glutamic acid at position 170, leucine at position 191, methionine at position 223, glutamine at position 235, valine at position 258, isoleucine at position 276, tyrosine at position 280, methionine at position 291, threonine at position 313, arginine at position 372, lysine at position 375, glutamine at position 403, asparagine at position 404, serine at position 406, isoleucine at position 407, and glutamic acid at position 479.

Furthermore, the mutant luciferase according to (c) above among the $5^{th}$ mutant luciferases is a mature protein in which a secretory signal peptide of CLuc has been removed from the amino acid sequence of the mutant luciferase according to (a).

Furthermore, the mutant luciferase according to (d) above among the $5^{th}$ mutant luciferases is a mature protein in which a secretory signal peptide of CLuc has been removed from the amino acid sequence of the mutant luciferase according to (b).

Meanwhile, a $6^{th}$ mutant luciferase according to the present invention is any one of the following proteins (a) to (d) (hereinafter, referred to as "the $6^{th}$ mutant luciferase(s)"):

(a) a protein consisting of an amino acid sequence that has, with respect to the amino acid sequence shown in SEQ ID NO: 2, a substitution of serine at position 406 with another amino acid;

(b) a protein consisting of an amino acid sequence that has, with respect to the amino acid sequence of (a) above, a deletion, a substitution, or an addition of one or several amino acids at positions other than position 406 of such amino acid and having luciferase activity with an emission spectral peak of 460 nm or more;

(c) a protein consisting of an amino acid sequence that has, with respect to the amino acid sequence shown in SEQ ID NO: 2, a deletion of amino acids at positions 1 to 18 and a substitution of serine at position 406 with another amino acid; and (d) a protein consisting of an amino acid sequence that has, with respect to the amino acid sequence of (c) above, a deletion, a substitution, or an addition of one or several amino acids at positions other than position 406 of such amino acid and having luciferase activity with an emission spectral peak of 460 nm or more.

The mutant luciferase according to (a) above among the $6^{th}$ mutant luciferases is a protein consisting of an amino acid sequence that has, with respect to the amino acid sequence of CLuc, a substitution of serine at position 406 with another amino acid. This protein exerts luciferase activity similarly to that of CLuc. However, because of the amino acid substitution, the protein is characterized by the emission spectral peak of 460 nm or more and particularly the emission spectral peak ranging from 460 nm to 490 nm (e.g., 460 nm to 462 nm) when luminescence is produced upon luciferin oxidation by the luciferase activity, whereas the same of CLuc is 454 nm. Here, "another amino acid" may be any amino acid other than serine. Examples of such amino acid include leucine and isoleucine and a particularly desirable example thereof is leucine.

Meanwhile, the mutant luciferase according to (b) above among the $6^{th}$ mutant luciferases consists of an amino acid sequence that has, with respect to the mutant luciferase according to (a), a deletion, a substitution, or an addition of one or several (e.g., 1 to 10, preferably 1 to 5, and particularly preferably 1 to 3) amino acids at positions other than position 406 of the above amino acid and has luciferase activity with an emission spectral peak of 460 nm or more. Examples of the positions other than position 406 of the amino acid include threonine at position 167, lysine at position 375, glutamine at position 403, asparagine at position 404, threonine at position 405, and isoleucine at position 407.

Furthermore, the mutant luciferase according to (c) above among the $6^{th}$ mutant luciferases is a mature protein in which a secretory signal peptide of CLuc has been removed from the amino acid sequence of the mutant luciferase according to (a).

Furthermore, the mutant luciferase according to (d) above among the $6^{th}$ mutant luciferases is a mature protein in which a secretory signal peptide of CLuc has been removed from the amino acid sequence of the mutant luciferase according to (b).

Meanwhile, a $7^{th}$ mutant luciferase according to the present invention is any one of the following proteins (a) to (d) (hereinafter, referred to as "the $7^{th}$ mutant luciferase(s)"):

(a) a protein consisting of an amino acid sequence that has, with respect to the amino acid sequence shown in SEQ ID NO: 2, a substitution of isoleucine at position 407 with another amino acid;

(b) a protein consisting of an amino acid sequence that has, with respect to the amino acid sequence of (a) above, a deletion, a substitution, or an addition of one or several amino acids at positions other than position 407 of the above amino acid and having luciferase activity with an emission spectral peak of 460 nm or more;

(c) a protein consisting of an amino acid sequence that has, with respect to the amino acid sequence shown in SEQ ID NO: 2, a deletion of amino acids at positions 1 to 18 and a substitution of isoleucine at position 407 with another amino acid; and (d) a protein consisting of an amino acid sequence that has, with respect to the amino acid sequence of (c) above, a deletion, a substitution, or an addition of one or several amino acids at positions other than position 407 of such amino acid and having luciferase activity with an emission spectral peak of 460 nm or more.

The mutant luciferase according to (a) above among the $7^{th}$ mutant luciferases is a protein consisting of an amino acid sequence that has, with respect to the amino acid sequence of CLuc, a substitution of isoleucine at position 407 with another amino acid. This protein exerts luciferase activity similarly to CLuc. However, because of the amino acid substitution, the protein is characterized by the emission spectral peak of 460 nm or more and particularly the emission spectral peak ranging from 460 nm to 490 nm (e.g., 460 nm to 462 nm) when luminescence is produced upon luciferin oxidation by the luciferase activity, whereas the same of CLuc is 454 nm. Here, "another amino acid" may be any amino acid other than isoleucine. Examples of such amino acid include glycine and alanine and a particularly desirable example thereof is alanine.

Meanwhile, the mutant luciferase according to (b) above among the $7^{th}$ mutant luciferases consists of an amino acid sequence that has, with respect to the mutant luciferase according to (a), a deletion, a substitution, or an addition of one or several (e.g., 1 to 10, preferably 1 to 5, and particularly preferably 1 to 3) amino acids at positions other than position 407 of the above amino acid and has luciferase activity with an emission spectral peak of 460 nm or more. Examples of the positions other than position 407 of the amino acid include threonine at position 167, lysine at position 375, glutamine at position 403, asparagine at position 404, threonine at position 405, and serine at position 406.

Furthermore, the mutant luciferase according to (c) above among the $7^{th}$ mutant luciferases is a mature protein from which a secretory signal peptide of CLuc has been removed from the amino acid sequence of the mutant luciferase according to (a).

Furthermore, the mutant luciferase according to (d) above among the $7^{th}$ mutant luciferases is a mature protein from which a secretory signal peptide of CLuc has been removed from the amino acid sequence of the mutant luciferase according to (b).

The mutant luciferases according to the present invention also includes a protein containing multiple amino acid substitutions that form a combination of any two or more (e.g., 2 to 10, preferably 2 to 8, and particularly preferably 2 to 6) of each predetermined amino acid substitution in the $1^{st}$ and the $3^{rd}$ to the $7^{th}$ mutant luciferases above and amino acid substitutions at the other positions in the amino acid sequence shown in SEQ ID NO: 2, and having luciferase activity with an emission spectral peak of 458 nm or more and particularly an emission spectral peak ranging from 458 nm to 490 nm (e.g., 458 nm to 475 nm). An example of such mutant luciferase containing such multiple amino acid substitutions is an $8^{th}$ mutant luciferase (hereinafter, referred to as "the $8^{th}$ mutant luciferase(s)") represented by any one of the following proteins (a) to (d):

(a) a protein consisting of an amino acid sequence that has, with respect to amino acid sequence shown in SEQ ID NO: 2, a substitution of leucine at position 191, glutamine at position 235, tyrosine at position 280, arginine at position 372, glutamine at position 403, asparagine at position 404, and threonine at position 405 with other amino acids;

(b) a protein consisting of an amino acid sequence that has, with respect to the amino acid sequence of (a) above, a deletion, a substitution, or an addition of one or several amino acids at positions other than the positions of such amino acids and having luciferase activity with an emission spectral peak of 466 nm or more;

(c) a protein consisting of an amino acid sequence that has, with respect to the amino acid sequence shown in SEQ ID NO: 2, a deletion of amino acids at positions 1 to 18 and substitutions of leucine at position 191, glutamine at position 235, tyrosine at position 280, arginine at position 372, glutamine at position 403, asparagine at position 404, and threonine at position 405 with other amino acids; and (d) a protein consisting of an amino acid sequence that has, with respect to the amino acid sequence of (c) above, a deletion, a substitution, or an addition of one or several amino acids at positions other than the positions of such amino acids and having luciferase activity with an emission spectral peak of 466 nm or more.

The mutant luciferase according to (a) above among the $8^{th}$ mutant luciferases is a protein consisting of an amino acid sequence that has, with respect to the amino acid sequence of CLuc, in addition to substitutions of asparagine at position 404 corresponding to the position of an amino acid substitution in the $4^{th}$ mutant luciferases and threonine at position 405 corresponding to the position of an amino acid substitution in the $5^{th}$ mutant luciferases, substitutions of leucine at position 191, glutamine at position 235, tyrosine at position 280, arginine at position 372, and glutamine at position 403 with other amino acids. This protein exerts luciferase activity similarly to CLuc. However, because of the amino acid substitutions, the protein is characterized by an emission spectral peak of 466 nm or more and particularly an emission spectral peak ranging from 466 nm to 490 nm (e.g., 466 nm to 475 nm) when luminescence is produced upon luciferin oxidation by the luciferase activity, whereas the same of CLuc is 454 nm. Here, examples of the amino acid substitution at each amino acid position include a combination of the following (A) to (G):

(A) a substitution of leucine at position 191 with glutamine;
(B) a substitution of glutamine at position 235 with arginine;
(C) a substitution of tyrosine at position 280 with aspartic acid;
(D) a substitution of arginine at position 372 with leucine;
(E) a substitution of glutamine at position 403 with proline;
(F) a substitution of asparagine at position 404 with glycine; and
(G) a substitution of threonine at position 405 with methionine.

Meanwhile, the mutant luciferase according to (b) above among the $8^{th}$ mutant luciferases consists of an amino acid sequence that has, with respect to the mutant luciferase according to (a), a deletion, a substitution, or an addition of one or several (e.g., 1 to 10, preferably 1 to 5, and particularly preferably 1 to 3) amino acids at positions other than the predetermined positions of the above amino acids and has luciferase activity with an emission spectral peak of 466 nm or more. Examples of the positions other than the predetermined positions of the above amino acids include aspartic acid at position 112, methionine at position 291, and threonine at position 313.

Furthermore, the mutant luciferase according to (c) above among the $8^{th}$ mutant luciferases is a mature protein in which a secretory signal peptide of CLuc has been removed from the amino acid sequence of the mutant luciferase according to (a).

Furthermore, the mutant luciferase according to (d) above among the $8^{th}$ mutant luciferases is a mature protein in which a secretory signal peptide of CLuc has been removed from the amino acid sequence of the mutant luciferase according to (b).

The mutant luciferases according to the present invention also include a protein containing multiple amino acid substitutions that form a combination of any two or more (e.g., 2 to 10, preferably 2 to 8, and particularly preferably 2 to 6) of the amino acid substitution in the $2^{nd}$ mutant luciferases and amino acid substitutions at the other positions in the amino acid sequence shown in SEQ ID NO: 2, and having luciferase activity with an emission spectral peak of 449 nm or less and particularly an emission spectral peak ranging from 420 nm to 449 nm (e.g., 425 nm to 449 nm). An example of such mutant luciferase containing such multiple amino acid substitutions is a $9^{th}$ mutant luciferase (hereinafter, referred to as "the $9^{th}$ mutant luciferase(s)") represented by any one of the following proteins (a) to (d):

(a) a protein consisting of an amino acid sequence that has, with respect to the amino acid sequence shown in SEQ ID NO: 2, substitutions of methionine at position 178, leucine at position 191, tyrosine at position 280, arginine at position 372, glutamine at position 403, asparagine at position 404, and threonine at position 405 with other amino acids;

(b) a protein consisting of an amino acid sequence that has, with respect to the amino acid sequence of (a) above, a deletion, a substitution, or an addition of one or several amino acids at positions other than the positions of such amino acids and having luciferase activity with an emission spectral peak of 435 nm or less;

(c) a protein consisting of an amino acid sequence that has, with respect to the amino acid sequence shown in SEQ ID NO: 2, a deletion of amino acids at positions 1 to 18 and substitutions of methionine at position 178, leucine at position 191, tyrosine at position 280, arginine at position 372, glutamine at position 403, asparagine at position 404, and threonine at position 405 with other amino acids; and (d) a protein consisting of an amino acid sequence that has, with respect to the amino acid sequence of (c) above, a deletion, a substitution, or an addition of one or several amino acids at positions other than the positions of such amino acids and having luciferase activity with an emission spectral peak of 435 nm or less.

The mutant luciferase according to (a) above among the $9^{th}$ mutant luciferases is a protein consisting of an amino acid sequence that has, with respect to the amino acid sequence of CLuc, in addition to the substitution of methionine at position 178 corresponding to the position of an amino acid substitution in the $2^{nd}$ mutant luciferases, substitutions of leucine at position 191, tyrosine at position 280, arginine at position 372, glutamine at position 403, asparagine at position 404, and threonine at position 405 with other amino acids. This protein exerts luciferase activity similarly to CLuc. However, because of the amino acid substitutions, the protein is characterized by an emission spectral peak of 435 nm or less and particularly an emission spectral peak ranging from 420 nm to 435 nm (e.g., 425 nm to 435 nm) when luminescence is produced upon luciferin oxidation by the luciferase activity, whereas the same of CLuc is 454 nm. Here, examples of the amino acid substitution at each amino acid position include a combination of the following (A) to (G):

(A) a substitution of methionine at position 178 with arginine;
(B) a substitution of leucine at position 191 with glutamine;
(C) a substitution of tyrosine at position 280 with aspartic acid;
(D) a substitution of arginine at position 372 with leucine;

(E) a substitution of glutamine at position 403 with proline;
(F) a substitution of asparagine at position 404 with glycine; and
(G) a substitution of threonine at position 405 with methionine.

Meanwhile, the mutant luciferase according to (b) above among the 9$^{th}$ mutant luciferases consists of an amino acid sequence that has a deletion, a substitution, or an addition of one or several (e.g., 1 to 10, preferably 1 to 5, and particularly preferably 1 to 3) amino acids at positions other than the predetermined positions of the above amino acids with respect to the mutant luciferase according to (a) and has luciferase activity with an emission spectral peak of 435 nm or less. Examples of the positions other than the predetermined positions of the above amino acids include methionine at position 291 and threonine at position 313.

Furthermore, the mutant luciferase according to (c) above among the 9$^{th}$ mutant luciferases is a mature protein from which a secretory signal peptide of CLuc has been removed from the amino acid sequence of the mutant luciferase according to (a).

Furthermore, the mutant luciferase according to (d) above among the 9$^{th}$ mutant luciferases is a mature protein from which a secretory signal peptide of CLuc has been removed from the amino acid sequence of the mutant luciferase according to (b).

In addition, the mutant luciferases according to the present invention further include a protein that maintains each predetermined amino acid substitution, consists of an amino acid sequence having 80% or more, preferably 90% or more, and particularly preferably 95% or more amino acid identity with respect to the amino acid sequence of the protein according to (a) or (c) of the above-described 1$^{st}$ to the 9$^{th}$ mutant luciferases, and has luciferase activity with a predetermined emission spectral peak.

Furthermore, concerning the emission spectral peaks of luciferases, errors may occur due to a measurement method, a spectrum correction method, smoothing, or the like employed. Hence, the mutant luciferases according to the present invention also includes a mutant luciferase having luciferase activity with an emission spectral peak within an error range of several nm (e.g., ±5 nm, preferably ±4 nm, and particularly preferably ±2 nm) with respect to the above emission spectral peak, as long as the above relative emission spectral peak shifts are involved with respect to the wild-type luciferase (CLuc).

Hereinafter, the 1$^{st}$ to the 9$^{th}$ mutant luciferases are together referred to as "the mutant luciferase(s) according to the present invention."

The above mutant luciferases according to the present invention can be prepared in the form of fusion proteins linked to foreign proteins or peptides. Here, the term "foreign protein or peptide" refers to an exogenous protein or peptide with respect to the mutant luciferases according to the present invention. Examples of foreign proteins or peptides include proteins or peptides (e.g., glutathione S-transferase, a maltose binding protein, thioredoxin, a cellulose binding domain, a streptavidin-binding peptide, and a histidine tag) to be used for protein purification, and signal peptides (e.g., a secretory signal peptide (amino acid sequence: SEQ ID NO: 3) of the α factor of budding yeast, a signal peptide (amino acid sequence: SEQ ID NO: 4) of invertase of budding yeast, and a signal peptide (amino acid sequence: SEQ ID NO: 5) of membrane protein Ste6p of budding yeast) for extracellular secretion or transfer to intracellular organs. For example, a gene encoding a fusion protein prepared by linking a secretory signal peptide appropriate for a host to be transformed to the mature protein of a mutant luciferase according to the present invention is transformed into the host, so that the mutant luciferase according to the present invention can be secreted and expressed extracellularly. A position in such a mutant luciferase according to the present invention, to which a foreign protein or peptide is linked, can be adequately selected so that the mutant luciferase according to the present invention and a foreign protein or peptide can each retain its functions or activity. For example, in the case of a fusion protein prepared by linking a secretory signal peptide to the mature protein of a mutant luciferase according to the present invention, the secretory signal peptide can be linked to the N-terminal side of the mature protein (specifically, the N-terminal side of amino acid at position 19 of the amino acid sequence shown in SEQ ID NO: 2).

The genes according to the present invention are genes encoding the mutant luciferases according to the present invention or genes encoding the above fusion proteins. The mutant luciferases according to the present invention or the fusion proteins can be expressed via introduction of these genes into hosts.

Hosts are not particularly limited. Examples of hosts include yeast, bacteria of the genus *Escherichia* such as *Escherichia coli*, bacteria of the genus *Bacillus* such as *Bacillus subtilis*, or bacteria of the genus *Pseudomonas* such as *Pseudomonas putida*, animal cells such as COS cells, insect cells such as Sf9, or plants belonging to the family Brassicaceae. Yeast may be any yeast and examples of yeast include *Saccharomyces cerevisiae, Shizosaccharomyces pombe, Pichia pastoris, Candida albicans*, and *Hansenula polymorpha*. In particular, *Saccharomyces cerevisiae* is preferred.

First, the genes encoding the mutant luciferases according to the present invention or the genes encoding foreign proteins or peptides are prepared. These genes can be easily obtained by PCR using, for example, genomic DNA or the like of an organism (e.g., *Cypridina noctiluca*) from which the genes are derived as a template and primers complementary to the nucleotide sequences at both ends of the relevant region. However, the mutant luciferases according to the present invention have amino acid substitutions with respect to the amino acid sequence of CLuc. Thus, the genes encoding the mutant luciferases according to the present invention can be obtained by further introducing mutations into the PCR products obtained as described above by site-directed mutagenesis or the like.

Once the nucleotide sequences are confirmed, genes encoding the mutant luciferases according to the present invention or genes encoding foreign proteins or peptides can then be obtained by chemical synthesis, PCR using cloned probes as templates, or hybridization using DNA fragments having the nucleotide sequences as probes. Furthermore, mutants which are derived from genes encoding the mutant luciferases according to the present invention or genes encoding foreign proteins or peptides and have functions equivalent to those before mutation can be synthesized by site-directed mutagenesis or the like.

In addition, for introduction of mutations into genes encoding the mutant luciferases according to the present invention or genes encoding foreign proteins or peptides, a known technique such as the Kunkel method or the Gapped duplex method or a method according thereto can be employed. For example, mutations are introduced using a mutagenesis kit (e.g., Mutant-K (TAKARA) or Mutant-G (TAKARA)) using site-directed mutagenesis or a LA PCR in vitro Mutagenesis series kit (TAKARA).

When a gene encoding a fusion protein is prepared by ligating a gene encoding the mutant luciferase according to the present invention to a gene encoding a foreign protein or peptide, DNA is prepared by ligating the gene encoding the foreign protein or peptide to the gene encoding the mutant luciferase according to the present invention. Such DNA itself may be prepared via ligation, a vector containing the DNA, or the like.

As a method for ligating a gene encoding a foreign protein or peptide to a gene encoding a mutant luciferase according to the present invention, a method is employed, which involves cleaving each purified gene encoding the mutant luciferase according to the present invention and a purified gene encoding a foreign protein or peptide with an appropriate restriction enzyme and then ligating the genes to each other. Furthermore, a method that may be employed herein involves providing a homologous region in a gene encoding a mutant luciferase according to the present invention and a gene encoding a foreign protein or peptide and then ligating them by an in vitro method using PCR or the like or an in vivo method using yeast or the like.

A recombinant vector containing a gene according to the present invention can be obtained by inserting the gene according to the present invention into an appropriate vector. Vectors that can be used herein are not particularly limited, as long as they are capable of replicating within hosts. Examples of such vectors include plasmids, shuttle vectors, and helper plasmids. When a vector is incapable of replicating, the vector may be a DNA fragment that will become capable of replicating when it is inserted into the chromosome of a host, for example.

Examples of plasmid DNA include plasmids derived from *Escherichia coli* (e.g., pBR322, pBR325, pUC118, pUC119, pUC18, pUC19, and pBluescript), plasmids derived from *Bacillus subtilis* (e.g., pUB110 and pTP5), and plasmids derived from yeast (e.g., the YEp line such as YEp13 and the YCp line such as YCp50). Examples of phage DNA include $\lambda$ phages (e.g., Charon4A, Charon21A, EMBL3, EMBL4, $\lambda$gt10, $\lambda$gt11, and $\lambda$ZAP). Furthermore, animal viruses such as a retrovirus or a vaccinia virus and vectors of insect viruses such as a baculovirus can also be used.

A method for inserting the gene according to the present invention into a vector can be carried out in accordance with a method that involves ligating a gene encoding a foreign protein or peptide to a gene encoding a mutant luciferase according to the present invention, as described above.

Moreover, a transformant is prepared by introducing a gene according to the present invention or a recombinant vector (hereinafter, referred to as "the recombinant vector or the like according to the present invention") containing the gene according to the present invention into a host.

A method for introducing the recombinant vector or the like according to the present invention into yeast is not particularly limited, as long as the method is used for introducing DNA into yeast. Examples of the method include electroporation, a spheroplast method, and a lithium acetate method. Moreover, a yeast transformation method that may also be used herein is a type of substitution and/or insertion into a chromosome using a DNA sequence homologous to an arbitrary region in a vector (e.g., YIp vector) or a chromosome. Furthermore, a method for introducing the recombinant vector or the like according to the present invention into yeast may be any method described in general experimental protocols, journal articles, or the like.

A method for introducing the recombinant vector or the like according to the present invention into bacteria is not particularly limited, as long as it is a method for introducing DNA into bacteria. Examples of the method include a method using calcium ions and electroporation.

When animal cells are used as hosts, monkey cells (COS-7 and Vero), Chinese hamster ovary cells (CHO cells), mouse L cells, and the like are used. Examples of a method for introducing the recombinant vector or the like according to the present invention into animal cells include electroporation, a calcium phosphate method, and lipofection.

When insect cells are used as hosts, Sf9 cells and the like are used. Examples of a method for introducing the recombinant vector or the like according to the present invention into insect cells include a calcium phosphate method, lipofection, and electroporation.

When plants are used as hosts, whole plant bodies, plant organs (e.g., leaves, petals, stems, roots, and seeds), plant tissues (e.g., epidermis, phloem, parenchyma, xylem, and vascular bundle), cultured plant cells, and the like are used. Examples of a method for introducing the recombinant vector or the like according to the present invention into plants include electroporation, an *agrobacterium* method, a particle gun method, and the PEG method.

Whether or not the recombinant vector or the like according to the present invention has been incorporated into hosts can be confirmed by the PCR method, Southern hybridization, Northern hybridization, or the like. For example, DNA is prepared from a transformant, DNA-specific primers are designed, and then PCR is carried out. Subsequently, the amplification products are subjected to agarose gel electrophoresis, polyacrylamide gel electrophoresis, capillary electrophoresis, or the like, and then stained with ethidium bromide, SYBR Green solution, or the like. The amplification products are detected as bands, so that transformation is confirmed. Furthermore, PCR is carried out using primers previously labeled with a fluorescent dye or the like, and then amplification products can also be detected. Furthermore, a method that may also be employed herein involves binding amplification products to a solid phase such as a microplate and then confirming the amplification products by fluorescence reaction, enzyme reaction, or the like.

Next, the thus obtained transformant is cultured under conditions that enable the growth. When the culture or culture supernatant of the transformant is directly subjected to measurement of enzyme activity, the transformant is cultured under conditions where the mutant luciferases according to the present invention are not deactivated. For example, when transformed yeast in which the recombinant vector or the like according to the present invention has been introduced is cultured, the temperature is set ranging from 4° C. to 37° C. and preferably ranging from 20° C. to 30° C., for example, so that yeast can grow and the mutant luciferases according to the present invention are not deactivated. Furthermore, pH for medium is set ranging from 3.5 to 6.5 and preferably ranging from 5.5 to 6.0, for example. Time for culturing ranges from 1 to 120 hours and preferably ranges from 1 to 24 hours corresponding to the logarithmic growth phase, for example.

As described above, the mutant luciferases according to the present invention or fusion proteins of the mutant luciferase according to the present invention with foreign proteins or peptides can be obtained from the above transformant.

When the activity of the mutant luciferases according to the present invention is measured, for example, the above transformants are cultured and then the thus obtained culture or culture supernatant is caused to come into contact with luciferin, that is a substrate, (e.g., sea-firefly luciferin) or a derivative thereof under conditions where the enzyme reaction of the mutant luciferases according to the present invention can take place. Here, an example thereof is a luciferin derivative in which the chemical structure of a side chain at position C2, C6, or C8 in the imidazopyrazinone skeleton of the luciferin has been substituted with a functional group (e.g., an aromatic group, aliphatic group, carboxylic acid, or amino group) or the like that is electrolyzed in an aqueous solution. The structure or position of a functional group is not limited, as long as light is emitted (luminescence is produced) by the functions of sea-firefly luciferase. Because of such substitution, enhancement in luminescence intensity, improvement of suppression of autolysis, and the like can be expected.

Moreover, conditions where enzyme reaction takes place mean conditions where luciferin specifically binds to the active center of the mutant luciferase according to the present invention so as to generate a complex and thus the enzyme reaction proceeds. Moreover, the phrase "contact ( . . . to come into contact with . . . )" refers to a condition where the mutant luciferases according to the present invention in cultures or culture supernatants to come close to luciferin, so that enzyme reaction takes place. Furthermore, the term "culture(s)" refers to a culture solution or a medium containing a transformant. For example, when a mutant luciferase according to the present invention is linked to a secretory signal peptide appropriate for a host, the mutant luciferase is secreted in the medium. Therefore, such a culture solution or medium containing a transformant can be used intact. Alternatively, a culture supernatant obtained by separation of a transformant by centrifugation or the like can also be used. Such a culture supernatant can also be subjected to dilution, condensation, dialysis, purification, or the like.

Regarding conditions for causing contact, the temperature is set at 0° C. to 40° C. and preferably 15° C. to 30° C., for example. Furthermore, the pH is set at 4.0 to 9.0 and preferably 6.0 to 8.0, for example. The contact time (reaction time) ranges from 1 second to 30 minutes and preferably ranges from 1 second to 30 seconds, for example. In particular, a solution of luciferin or a derivative thereof, which has been diluted with any one of various buffers is added to a culture or a culture supernatant, so that the pH of the culture or the culture supernatant can be shifted to the pH at which the enzyme activity of the mutant luciferase(s) according to the present invention is high. For example, the above-described pH upon contact can be set by adding to a culture or a culture supernatant containing the mutant luciferase(s) according to the present invention the solution of luciferin or a derivative thereof, which is prepared via dilution with a buffer, such as Tris hydrochloric acid buffer (Tris-HCl) that is 2 M or less (preferably ranges from 50 mM to 200 mM) and has pH ranging from 3.5 to 9.0 (preferably, pH 7.0 to pH 8.0).

Regarding the concentration of luciferin or a derivative thereof, which is a substrate for a culture or a culture supernatant, for example, luciferin or a derivative thereof is added to a final concentration of 0.1 µM or more and preferably ranging from 1.25 µM to 2.5 µM, with respect to 0.05 or more of the turbidity (e.g., absorbance at 600 nm) of the culture or the culture supernatant of a transformant having the mutant luciferase(s) according to the present invention.

Next, the enzyme activity of the mutant luciferases according to the present invention is measured. For example, a measurement method involves subjecting a mixture of the culture or the culture supernatant of a transformant with luciferin or a derivative thereof to luminescence measurement using a luminometer and then measuring the enzyme activity as relative light unit (RLU). Moreover, to standardize a measured value by correcting the enzyme activity upon activity measurement, turbidity (e.g., absorbance at 600 nm) of a culture solution or a culture supernatant is measured and then the relative light unit is divided by turbidity for correction, so that the thus corrected value (RLU/OD) can be obtained as an enzyme activity level. Alternatively, a method that is also preferable for standardization of relative light unit involves measuring the level of ATP contained in a transformant and then dividing the relative light unit by the ATP level. Furthermore, another method that may also be employed herein involves causing simultaneous expression of another enzyme or protein in the transformant, measuring the enzyme or protein amount, and then dividing the relative light unit by the level for correction. The mutant luciferases according to the present invention exert luciferase activity with the emission spectral peaks differing from that of CLuc. With another method that may also be employed herein, luminescence can be distinguished from the other using such characteristics of having different emission spectra. The method involves causing expression of CLuc and then dividing by the luminescence derived from CLuc for correction.

Furthermore, for example, when a host is a microorganism such as *Saccharomyces cerevisiae*, a transformant is grown in agar medium to form colonies. Hence, for example, enzyme activity can be measured by adding luciferin or a derivative thereof to agar medium containing a transformant and then measuring the luminescence intensity of the colonies using a luminescence detector having a CCD camera, for example.

Furthermore, the mutant luciferases according to the present invention exert luciferase activity with emission spectral peaks differing from that of CLuc. Hence, in addition to the above measurement of luciferase activity, whether or not the mutant luciferases according to the present invention have emission spectral peaks within the above range is confirmed by measurement using a luminescence detector with a plurality of optical filters that have different transmission characteristics and a CCD camera, for example.

When significant luciferase activity and expected emission spectral peaks are confirmed through measurement of such luciferase activity and emission spectral peaks, it can be concluded that the mutant luciferases according to the present invention have been obtained.

Furthermore, according to the above-explained measurement of emission spectral peaks, the transcriptional activity of a plurality of promoters can be evaluated simultaneously using CLuc and the mutant luciferases according to the present invention as reporter proteins.

In the method for evaluating the transcriptional activity of promoters according to the present invention, 2 or more luciferases are used from among wild-type CLuc, the mutant luciferases according to the present invention, and fusion proteins of wild-type CLuc or the mutant luciferases according to the present invention with foreign proteins or peptides. Here, the term "wild-type CLuc" refers to the following protein (a) or (b):

(a) CLuc consisting of the amino acid sequence shown in SEQ ID NO: 2; or (b) a mature protein consisting of an amino acid sequence that has a deletion of a secretory signal peptide with respect to the amino acid sequence shown in SEQ ID NO: 2.

Moreover, the term "a fusion protein(s) of wild-type CLuc with a foreign protein(s) or peptide(s)" refers to a fusion protein in which a foreign protein or peptide is linked to the protein (a) or (b) above.

First, DNA in which different promoters to be evaluated have been ligated to the 5' upstream side of each of these two or more luciferase genes is introduced into a host. Ligation of a promoter to the 5' upstream side of the luciferase gene results in arrangement of the luciferase gene under the control of the promoter. Subsequently, the thus obtained transformant is cultured and then a culture or a culture supernatant is obtained. Furthermore, the culture or the culture supernatant is caused to come into contact with luciferin or a derivative thereof. Next, different luminescence intensities due to different emission spectral peaks resulting from the activity of a plurality of luciferases introduced are measured, so that the transcriptional activity of a plurality of promoters can be evaluated simultaneously and quantitatively. At this time, based on the transcriptional activity of one of the plurality of promoters, the transcriptional activity of the other promoters can be corrected. Different luminescence intensities due to a plurality of different emission spectral peaks can be measured by installing an appropriate filter set in a luminometer applicable for multi-reporter assays, "AB-2250 Luminescensor MCA (ATTO Corporation)," for example, which is an apparatus for which the principle according to JP Patent Publication (Kokai) No. 2004-187652 has been applied.

Moreover, the mutant luciferases according to the present invention or fusion proteins of the mutant luciferases according to the present invention with foreign proteins or peptides are used for BRET (Bioluminescence resonance energy transfer) or the like, so that light emission or energy release can be caused.

In the method for emitting light or releasing energy according to the present invention, first, the mutant luciferases according to the present invention or fusion proteins of the mutant luciferases according to the present invention with foreign proteins or peptides is come into contact with luciferin or a derivative thereof. Because of this contact, luciferin is oxidized to oxyluciferin in its excited state. Subsequently, the oxyluciferin in its excited state and a chemical substance are caused to act on each other. Here, the term "chemical substance" refers to a substance that receives excitation energy of a luminous object via energy resonance so as to be able to produce fluorescence because of the energy. Examples of such chemical substance include fluorescein, FITC, TRITC, TAMRA, and fluorescent proteins such as GFP (green fluorescent protein derived from Aequorea victoria) and mutants thereof (e.g., CFP and YFP), and DsRed (red fluorescent protein derived from Porifera). Furthermore, the expression "to act." refers to arrangement of oxyluciferin and a chemical substance at positions that enable (in terms of distance) topological energy transfer.

The oxyluciferin and the chemical substance are then caused to act on each other, so that luminescence or energy involved in luminescence produced when the oxyluciferin returns to the ground state shifts to the chemical substance. The chemical substance is excited so as to be able to emit light or release energy depending on the excitation energy.

As explained above, the use of the mutant luciferases according to the present invention makes it possible to measure (multi-reporter assay) the transcriptional activity of a plurality of different promoters using a single type of substrate and a single time of luminescence measurement. Moreover, with the use of the mutant luciferases according to the present invention, an emission spectrum corresponding to the excitation spectrum of a specific chemical substance is provided, so that higher BRET efficiency is exerted and a strong signal can be obtained. Furthermore, the use of the mutant luciferases according to the present invention makes it possible to conduct simultaneous analysis of structural changes of a plurality of proteins using a plurality of BRETs.

EXAMPLES

Hereinafter, the present invention will be described in detail by examples as follows, but the scope of the present invention is not limited by these examples.

The plurality of mutant luciferases according to the present invention and the luciferase from which the mutant luciferases are derived were expressed in Saccharomyces cerevisiae and the resulting emission spectra were compared.

Example 1

Secretion and Expression of CLuc in Saccharomyces cerevisiae

The plasmid pCLuRA-TDH3 disclosed in the pamphlet of International Publication No. 2006/132350 was used as an expression vector for secretion and expression of CLuc in Saccharomyces cerevisiae.

The plasmid pCLuRA-TDH3 contained a gene (hereinafter, referred to as "αCLuc gene") encoding a fusion protein (hereinafter, referred to as "αCLuc") of a secretory signal peptide (amino acid sequence: SEQ ID NO: 3) of α factor of budding yeast with a CLuc mature protein (the amino acid sequence resulting when an amino acid sequence ranging from positions 1 to 18 had been removed from the amino acid sequence of CLuc shown in SEQ ID NO: 2). The amino acid sequence shown in SEQ ID NO: 6 was the amino acid sequence of αCLuc. The fusion protein of CLuc with the secretory signal peptide derived from α factor was prepared, so that CLuc was secreted outside the microorganisms.

Furthermore, in the plasmid pCLuRA-TDH3, a promoter of the Saccharomyces cerevisiae TDH3 (systematic gene name: YGR192C) gene had been incorporated upstream (5' side) of the αCLuc gene. The expression of the αCLuc gene is controlled by the promoter. The nucleotide sequence shown in SEQ ID NO: 7 is a partial nucleotide sequence of the plasmid pCLuRA-TDH3, containing a 700-bp 5' upstream initiation codon of αCLuc containing a TDH3 promoter sequence, the αCLuc coding region, and a 300-bp 3' downstream termination codon of αCLuc containing a CYC1 terminator sequence.

The Saccharomyces cerevisiae BY4743ΔPRB1 strain was transformed using the plasmid pCLuRA-TDH3. An EZ-transformation kit (BIO101) was used for transformation.

A uracil-free synthetic agar medium (0.67% yeast nitrogen base without amino acids (Becton, Dickinson and Company), 40 μg/ml adenine, 20 μg/ml L-arginine monohydrochloride, 100 μg/ml L-aspartic acid, 100 μg/ml L-sodium glutamate monohydrate, 20 μg/ml L-histidine, 60 μg/ml L-leucine, 30 μg/ml L-lysine hydrochloride, 20 μg/ml L-methionine, 50 μg/ml L-phenylalanine, 375 μg/ml L-serine, 200 μg/ml L-threonine, 40 μg/ml L-tryptophan, 30 μg/ml L-tyrosine, 150 μg/ml L-valine, 2% glucose, and 2.0% agar; hereinafter, referred to simply as "SD-ura agar medium") was coated with the thus obtained transformant, followed by 3 days of culture at 30° C. As a result, a transformant containing the plasmid pCLuRA-TDH3 was obtained.

The transformant containing the plasmid pCLuRA-TDH3 obtained as described above was inoculated into a uracil-free synthetic liquid medium (0.67% yeast nitrogen base without amino acids (Becton, Dickinson and Company), 40 μg/ml adenine, 20 μg/ml L-arginine monohydrochloride, 100 μg/ml L-aspartic acid, 100 μg/ml L-sodium glutamate monohydrate, 20 μg/ml L-histidine, 60 μg/ml L-leucine, 30 μg/ml L-lysine hydrochloride, 20 μg/ml L-methionine, 50 μg/ml L-phenylalanine, 375 μg/ml L-serine, 200 μg/ml L-threonine, 40 μg/ml L-tryptophan, 30 μg/ml L-tyrosine, 150 μg/ml L-valine, 2% glucose, and 200 mM potassium phosphate, pH 6.0; hereinafter, referred to simply as "buffered SD-ura medium") having buffering action, followed by 24 hours of shake culture at 30° C.

After shake culture, a culture solution was centrifuged, so that a culture supernatant was isolated. Eighty (80) µl of a luciferin solution (1 µM luciferin, 100 mM Tris-HCl, pH 7.4) was added to 20 µl of the thus isolated culture supernatant and then luminescence was measured using a Berthold LB960 luminometer. As a result, luminescence was observed at $4\times10^5$ RLU/second. Specifically, secretion and expression of CLuc in the *Saccharomyces cerevisiae* BY4743ΔPRB1 strain was confirmed.

Example 2

Isolation of Mutant Luciferase Via Introduction of Random Mutation 2-1. Construction of Mutant CLuc Gene Library (N-Region Mutant Library)

A random point mutation was introduced into the αCLuc coding region of the plasmid pCLuRA-TDH3 by error prone PCR.

The subject region for introduction of the mutation was the first half portion of the αCLuc coding region (in the nucleotide sequence shown in SEQ ID NO: 7, the nucleotide sequence ranging from positions 900 to 1813; hereinafter, referred to as "N region"). The reason for limiting the range is that amplification of a long region is frequently difficult in error prone PCR. Moreover, the reason for not using as a subject region the nucleotide sequence ranging from positions 701 to 899 of the nucleotide sequence shown in SEQ ID NO: 7 is that this portion is a region encoding most of the secretory signal peptide of a factor.

The following oligo DNA primers were used in error prone PCR of the N region.

```
mut-CLuc-F:
ATACTACTATTGCCAGCATTGCTGCTAAAG    (SEQ ID NO: 8)

mut-CLuc-NR2:
CACGTGTGAGGCTCGCTCGTCTCCACCCAT    (SEQ ID NO: 9)
```

The composition of the reaction solution for error prone PCR of the N region is as follows: Taq DNA polymerase (Roche, 1 unit/µl): 5 µl; 10×PCR buffer without magnesium ion: 10 µl; mixed solution of deoxynucleotide for error prone PCR: 10 µl; 25 mM magnesium chloride: 28 µl; 5 mM manganese chloride: 2.5 µl; plasmid pCLuRA-TDH3 solution (150 ng/µl): 1 µl; mut-Cluc-F (SEQ ID NO: 8) (10 pmol/µl): 3 µl; mut-CLuc-NR2 (SEQ ID NO: 9) (10 pmol/µl): 3 µl; and sterile water: 37.3 µl.

The composition of the above mixed solution of deoxynucleotide for error prone PCR is as follows: 100 mM dCTP: 100 µl; 100 mM dTTP: 100 µl; 100 mM dGTP: 20 µl; 100 mM dATP: 20 µl; and sterile water: 760 µl.

Error prone PCR was carried out for 30 cycles each consisting of 94° C. for 1 minute (denaturation), 45° C. for 1 minute (annealing), and 72° C. for 1 minute (extension).

The PCR product obtained by error prone PCR was electrophoresed with 1% agarose, so that an approximately 900-bp DNA fragment was confirmed. This fragment was purified using GeneElute MINUS EtBr SPIN COLUMNS (Sigma), subjected to ethanol precipitation, and then dissolved in 20 µl of TE buffer (10 mM Tris-HCl, 1 mM EDTA, pH 8.0), thereby preparing a DNA solution.

Next, to ensure the obtainment of DNA in a sufficient amount for introduction into *Saccharomyces cerevisiae*, PCR was further carried out using the above DNA solution as a template (hereinafter, referred to as "2nd PCR").

The composition of the reaction solution of the 2nd PCR is as follows: KOD plus DNA polymerase (TOYOBO Co., Ltd.): 1 µl; 10×KOD plus buffer: 5 µl; 2 mM each dNTP mixture: 5 µl; 25 mM magnesium sulfate: 2 µl; mut-Cluc-F (SEQ ID NO: 8) (10 pmol/µl): 1.5 µl; mut-CLuc-NR2 (SEQ ID NO: 9) (10 pmol/µl): 1.5 µl; the above DNA solution: 1 µl; and sterile water: 33 µl.

The 2nd PCR was carried out for 1 cycle of 94° C. for 2 minutes (deactivation of anti-polymerase antibody) and 30 cycles each consisting of 94° C. for 15 seconds (denaturation), 50° C. for 30 seconds (annealing), and 68° C. for 1 minute (extension).

The PCR product obtained by the 2nd PCR was electrophoresed with 1% agarose, so that an approximately 900-bp DNA fragment was confirmed. The DNA fragment is hereinafter referred to as "N-region fragment."

The N-region fragment was purified from agarose gel using GeneElute MINUS EtBr SPIN COLUMNS (Sigma), subjected to ethanol precipitation, and then dissolved in 20 µl of TE buffer (hereinafter, referred to as "N-region fragment solution").

*Saccharomyces cerevisiae* generally undergoes homologous recombination within cells with high probability. Accordingly, a linear DNA fragment (hereinafter, referred to as a "complementary N-region fragment") lacking the nucleotide sequence ranging from positions 967 to 1703 of the nucleotide sequence as shown in SEQ ID NO: 7 in the nucleotide sequence of the plasmid pCLuRA-TDH3 and the "N-region fragment" in which a mutation has been introduced as described above are simultaneously introduced into *Saccharomyces cerevisiae*. Within *Saccharomyces cerevisiae*, circular DNA (the mutant plasmid pCLuRA-THD3 wherein a mutation has been introduced into the N region) is reconstituted by homologous recombination, so that *Saccharomyces cerevisiae* can be transformed with the reconstituted plasmid.

The "complementary N-region fragment" was prepared by PCR as follows. The following oligo DNA primers were used for PCR.

```
vec-CLuc-R:
GCTTCAGCCTCTCTTTTCTCGAGAG         (SEQ ID NO: 10)

SQ-CLuc-NF2:
TTCTCGAGCCGTACAAGGACAGCTGCCGCA    (SEQ ID NO: 11)
```

The composition of the reaction solution of the PCR is as follows: KOD plus DNA polymerase (TOYOBO Co., Ltd.): 1 µl; 10×KOD plus buffer: 5 µl; 2 mM each dNTP mixture: 5 µl; 25 mM magnesium sulfate: 2 µl; vec-CLuc-R (SEQ ID NO: 10) (10 pmol/µl): 1.5 µl; SQ-CLuc-NF2 (SEQ ID NO: 11) (10 pmol/µl): 1.5 µl; plasmid pCLuRA-TDH3 solution (150 ng/µl): 1 µl; and sterile water: 33 µl.

PCR was carried out for 1 cycle of 94° C. for 2 minutes (deactivation of anti-polymerase antibody) and 30 cycles each consisting of 94° C. for 15 seconds (denaturation) and 68° C. for 8 minutes (annealing and extension).

The thus obtained PCR product was electrophoresed with 1% agarose, so that an approximately 7-kbp DNA fragment was confirmed. The DNA fragment was purified using GeneElute MINUS EtBr SPIN COLUMNS (Sigma), subjected to ethanol precipitation, and then dissolved in 20 µl of TE buffer (hereinafter, referred to as a "complementary N-region fragment solution").

The overlapped portions between the N-region fragment and the complementary N-region fragment were the nucleotide sequence ranging from positions 900 to 966 and the nucleotide sequence ranging from positions 1704 to 1813 of the nucleotide sequence shown in SEQ ID NO: 7.

Five (5) μl of the N-region fragment solution was mixed with 5 μl of the complementary N-region fragment solution. The *Saccharomyces cerevisiae* BY4743ΔPRB1 strain was transformed by the lithium acetate method. An SD-ura agar medium was coated with the *Saccharomyces cerevisiae* BY4743ΔPRB1 strain subjected to transformation, followed by incubation at 30° C. for 48 hours. Many colonies that thus appeared were used as N-region mutant libraries.

2-2. Construction of Mutant CLuc Gene Library (C-Region Mutant Library)

In a manner similar to that used for the above construction of the N-region mutant libraries, C-region mutant libraries were constructed using the last half portion of the αCLuc coding region as the subject region for introduction of mutation.

The subject regions for introduction of mutation were the last half portion of the αCLuc coding region and an approximately 60-bp 3' non-coding region in the αCLuc coding region (the nucleotide sequence ranging from positions 1554 to 2663 of the nucleotide sequence shown in SEQ ID NO: 7; hereinafter, referred to as the "C region"). The reason why the 3' non-coding region of the αCLuc coding region was contained in the C region is to cause intracellular homologous recombination to take place outside the αCLuc coding region into which mutation should have been introduced and thus not to affect the mutagenesis efficiency with respect to the C-terminal coding region in the αCLuc coding region.

A C-region fragment corresponding to the N-region fragment of the above N-region mutant libraries was prepared by carrying out PCR in a manner similar to that used for error prone PCR and the 2nd PCR above except that the following oligo DNA primers were used.

```
mut-CLuc-CF1:
TCTCTGGCCTCTGTGGAGATCTTAAAATGA    (SEQ ID NO: 12)

mut-CLuc-R:
AACTCCTTCCTTTTCGGTTAGAGCGGATGT    (SEQ ID NO: 13)
```

The thus obtained PCR product was electrophoresed with 1% agarose, so that an approximately 1,100-bp DNA fragment was confirmed. Next, the DNA fragment (C-region fragment) was purified from agarose gel using GeneElute MINUS EtBr SPIN COLUMNS (Sigma), subjected to ethanol precipitation, and then dissolved in 20 μl of TE buffer, thereby resulting in a C-region fragment solution.

A complementary C-region fragment corresponding to the complementary N-region fragment of the above N-region mutant libraries was prepared. The complementary C-region fragment was prepared according to the method for preparing a complementary N-region fragment, except that the following oligo DNA primers and PCR reaction conditions were used.

Oligo DNA primers used herein are as follows.

```
vec-CLuc-F:
TCTAGAGGGCCGCATCATGTAATTA         (SEQ ID NO: 14)

SQ-CLuc-CR1:
TGGACAACCGTCAAACTCCTGGTTGATCTT    (SEQ ID NO: 15)
```

PCR was carried out for 1 cycle of 94° C. for 2 minutes (deactivation of anti-polymerase antibody) and 30 cycles each consisting of 94° C. for 15 seconds (denaturation), 55° C. for 30 seconds (annealing), and 68° C. for 8 minutes (extension).

The thus obtained PCR product was electrophoresed with 1% agarose, so that an approximately 6.5-kbp DNA fragment was confirmed. This DNA fragment (complementary C-region fragment) was purified using GeneElute MINUS EtBr SPIN COLUMNS (Sigma), subjected to ethanol precipitation, and then dissolved in 20 μl of TE buffer, thereby resulting in a complementary C-region fragment solution.

The overlapped portions between the C-region fragment and the complementary C-region fragment were the nucleotide sequence ranging from positions 1554 to 1663 and the nucleotide sequence ranging from positions 2576 to 2663 of the nucleotide sequence shown in SEQ ID NO: 7.

Five (5) μl of the C-region fragment solution was mixed with 5 μl of the complementary C-region fragment solution. The *Saccharomyces cerevisiae* BY4743ΔPRB1 strain was transformed by the lithium acetate method. An SD-ura agar medium was coated with the *Saccharomyces cerevisiae* BY4743ΔPRB1 strain subjected to transformation, followed by incubation at 30° C. for 48 hours. Many colonies that thus appeared were used as C-region mutant libraries.

2-3. Screening for Mutant Luciferases

Mutant luciferases with emission spectra that had shifted were screened for by filming sequentially the fluorescence using a CCD camera and 2 types of optical filter with different transmission characteristics. The optical filters used herein are GG495 and BG28 (SCHOTT). The former filter is a long-pass filter with a cut-off wavelength of around 495 nm. The latter filter is a band-pass filter with a maximum transmission wavelength of around 450 nm. The same sample (culture supernatant containing luciferase) was filmed with a CCD camera using these filters successively and then the recorded signal intensities were compared. Differences between the resulting ratio and that of wild-type CLuc indicate the occurrence of an emission spectral shift.

One (1) ml each of a buffered SD-ura medium was dispensed into a 96-well deep well plate (2 ml/well), and colonies of the N-region mutant libraries or the C-region mutant libraries were inoculated in separate wells (one colony per well) using a colony picker. In addition, as a control, *Saccharomyces cerevisiae* (BY4743ΔPRB1 strain transformed with plasmid pCLuRA-TDH3) secreting and expressing wild-type Cluc (into which no mutation had been introduced) was inoculated into 6 wells.

Subsequently, the inoculated plate was subjected to approximately 48 hours of culture at 30° C., centrifugation was carried out at 1,800 rpm, and then 20 μl of the culture supernatant was transferred from each well to a black 96-well plate.

A luciferin solution (1 μM luciferin, 100 mM Tris-HCl, pH 7.4) was added to each well, the plate was then set within a Light Capture (ATTO) provided with GG495, and then filming was carried out for 30 seconds to 2 minutes. Next, the optical glass filter was exchanged with BG28 immediately after filming, and filming was then carried out again for 30 seconds to 2 minutes. The thus filmed images were stored in the form of TIFF files in a computer.

Images filmed with the use of each filter were processed by image processing software (e.g., Adobe Photoshop). The ratio of the signal intensity of the image filmed with GG495 to the same of the image filmed with BG28 was subjected to pseudo-color processing and then the result was visually compared with that for wild-type Cluc. Therefore, clones suspected of having undergone emission spectral shift were selected.

As described above, as a result of screening of one thousand and hundreds of clones in each of the N-region mutant library and the C-region mutant library, an M178K mutant (a clone having M178K mutant CLuc in which methionine at position 178 of the amino acid sequence shown in SEQ ID NO: 2 had been substituted with lysine; corresponding to a transformant having the 2 mutant luciferase(s)) was obtained from the N-region mutant library, in which a shift to the shorter wavelength side was thought to take place; and a K375R mutant and a K375E mutant (a clone having K375R mutant having a substitution of lysine at position 375 of the amino acid sequence shown in SEQ ID NO: 2 with arginine and a clone having K375E mutant Cluc having a substitution of the same with glutamic acid; corresponding to a transformant having the 11 mutant luciferase(s)) were obtained from C-region mutant library, in which a shift to the longer wavelength side was thought to take place.

Here, for example, the term "K375R mutant Cluc" represents the mutant Cluc that has a substitution of lysine corresponding to position 375 of SEQ ID NO: 2 with arginine. The alphabetical letter representing an amino acid is a single letter selected based on the recommendation of the International Union of Pure and Applied Chemistry—International Union of Biochemistry (IUPAC-IUB). Moreover, the term "K375R mutant" refers to a clone having K375R mutant CLuc. Furthermore, a plasmid retained by the K375R mutant is referred to as "pCLuRA-TDH3[K375R]." Hereinafter, mutant CLuc, a mutant (clone) having mutant CLuc, and a plasmid retained by a mutant are designated in a similar manner.

2-4. Measurement of Emission Spectrum of Mutant Luciferase

The following transformed yeast (a) to (d) was separately shake-cultured in a buffered SD-ura medium and then centrifuged, so as to allow collection of the culture supernatant. The thus collected culture supernatants were each concentrated about 10 fold with a VivaSpin (molecular weight cut off: 10,000, SARTORIUS K. K.).

(a) *Saccharomyces cerevisiae* (the BY4743ΔPRB1 strain transformed with plasmid pCLuRA-TDH3) secreting and expressing wild-type CLuc
  (b) M178K mutant
  (c) K375R mutant
  (d) K375E mutant Next, the thus obtained concentrated solution of each culture supernatant was subjected to AB-1850 LumiFLSpectroCapture (emission spectrophotometer) (ATTO) so as to measure the emission spectra.

The composition of the reaction solution is as follows: 1 µM luciferin, 100 mM Tris-HCl, pH 7.5, and the above concentrated solution (approximately 1 µl to 3 µl).

The measured emission spectra are shown in FIG. 1. FIG. 1 shows the relative light unit for each luciferase to the wavelength, wherein "wild-type" denotes the measurement results for wild-type CLuc, "M178K" denotes the same for M178K mutant CLuc, "K375R" denotes the same for K375R mutant CLuc, and "K375E" denotes the same for K375E mutant CLuc.

As understood from FIG. 1, in the case of visual observation, whereas the emission spectral peak of wild-type CLuc was 453 nm, the emission spectral peak of K375R mutant CLuc was 461 nm, indicating a shift to the longer wavelength side of 8 nm. Furthermore, the emission spectral peak of K375E mutant CLuc was 460 nm, indicating a shift to the longer wavelength side of 7 nm. On the other hand, the emission spectral peak of M178K mutant CLuc was 447 nm, indicating a shift to the shorter wavelength side of 6 nm.

As described above, the difference between K375R mutant CLuc and M178K mutant CLuc in terms of emission spectral peak was 14 nm and the difference between K375E mutant CLuc and M178K mutant CLuc in terms of emission spectral peak was 13 nm. Hence, it was considered that they can be used for dual reporter assays.

2-5. Determination of Spectral Peak Wavelength from the Emission Spectra of Mutant Luciferase Regarding spectra measured using AB-1850 LumiFLSpectroCapture (emission spectrophotometer) (ATTO), data were further processed so as to find spectral peaks as follows.

Data comprising the measured wavelengths and luminescence intensities were recorded in a file using the control program attached to the instrument. Next, the recorded data was read by a macro file for correction attached to the instrument (Excel file (Microsoft)), so that the wavelength-dependent sensitivity of the detector was corrected and data were obtained from which the background (obtained by measuring the emission spectrum for the container alone) had been subtracted. Next, the data were recorded in the csv format (comma-deliminated text format) file in which the first line denotes wavelength and the second line denotes (normalized) luminescence intensity.

Furthermore, the thus obtained file was read by digital data analysis software OriginPro v7.5 (OriginLab) and then processed to remove the noise of luminescence intensities. For noise processing, FFT (fast Fourier transformation) analysis was employed. First, FFT analysis was conducted and then the wavelength distribution (in addition, since the horizontal axis on OriginPro is regarded as representing frequency, internal processing is carried out using Hz) was found. Based on the wavelength distribution, harmonic wavelength contents were regarded as noise, LPF (low-pass filter) processing was carried out, and then data filtering was carried out. Regarding the filtering of periodic wavelengths, in view of agreement between the original data containing noise and the processed data, 0.05 was employed for all data. For all data, periodic wavelength components with filtering periodic wavelengths of 0.05 or more were equally cut by LPT processing on OriginPro, inverse Fourier transform was carried out with the functions of the same program, and then the data were output on a file. This processing enabled conversion into a lower-noise smooth spectral curve without changing spectral outline and peak positions.

Finally, the file was read by Microsoft Excel 2003 (Microsoft), a wavelength at which the luminescence intensity reached the maximum was automatically detected, and then the wavelength was determined to be a peak wavelength.

Spectral measurement using wild-type CLuc and each mutant CLuc described in the section 2-4 above was basically carried out twice, and the above-mentioned determination of spectral peak wavelengths was carried out separately. When measurement was carried out more than once, the mean value of the thus obtained spectral peak wavelengths was found and this value was employed. When measurement was carried out twice or more for the same sample, a shift between a spectral peak wavelength and the mean value thereof fell approximately within 1 nm.

According to such method for determination of spectral peak wavelengths, the emission spectral peak of M178K mutant CLuc in the section 2-4 above shifted from visually measured 447 nm based on FIG. 1 to 449 nm. In addition, the emission spectral peak of wild-type CLuc and the emission spectral peaks of the other mutant CLuc shifted from visually measured 453 nm to 454 nm (wild-type CLuc), shifted from visually measured 461 nm to 463 nm (K375R mutant CLuc), and shifted from visually measured 460 nm to 462 nm (K375E mutant CLuc). It was concluded that determination of spectral peak wavelengths by visual measurement results in significant errors. Hence, a method was employed as follows, involving consistently carrying out the above-mentioned data processing and automatically determining spectral peak wavelengths via data processing.

In the following Examples, the emission spectral peaks of mutant CLuc were determined based on the method for determination of spectral peak wavelengths.

In addition, in the following Examples, unless otherwise specified, explanations of amino acid positions concern the amino acid sequence shown in SEQ ID NO: 2.

Example 3

Construction of T167 Saturation Mutant Library and Screening for Mutant CLuc

As a result of screening described in Example 2, a T167I mutant (a clone having T167I mutant CLuc in which threonine at position 167 of the amino acid sequence shown in SEQ ID NO: 2 had been substituted with isoleucine; corresponding to a transformant having the 3$^{rd}$ mutant luciferase(s)) was obtained. A plasmid retained by the clone is referred to as "pCLuRA-TDH3[T167I]." The emission spectral peak of the mutant CLuc secreted from the T167I mutant was 458 nm as measured by the method described in the section 2-5 in Example 2, indicating a shift to the longer wavelength side of 4 nm compared with that of wild-type CLuc.

Accordingly, a mutant library (hereinafter, referred to as the "T167 saturation mutant library") was constructed as follows, in which amino acid at position 167 of the amino acid sequence shown in SEQ ID NO: 2 was substituted with any one of the other amino acids. Then obtainment of a mutant with a shift to the further longer wavelength side was attempted.

The T167 saturation mutant library was constructed as follows.

First, the following PCR was carried out. Oligo DNA primers used herein are FAR-F: AACCCTCACTAAAGGGAA-CAAAAGCTGGCT (SEQ ID NO: 16) and T238-Rev: GTACGGGTTGGCGATGATAGG (SEQ ID NO: 17). The DNA fragment obtained by the PCR corresponded to the nucleotide sequence ranging from positions 1 to 1411 in the nucleotide sequence shown in SEQ ID NO: 7. The composition of the reaction solution for the PCR is as follows: KOD plus DNA polymerase: 0.4 µl; 10×KOD plus buffer: 2 µl; 2 mM each dNTP mixture: 2 µl; 25 mM magnesium sulfate: 0.8 µl; FAR-F (SEQ ID NO: 16) (10 pmol/µl): 0.6 µl; T238-Rev (SEQ ID NO: 17) (10 pmol/µl): 0.6 µl; plasmid pCLuRA-TDH3 solution (3.8 ng/µl): 1 µl; and sterile water: 12.6 µl. PCR was carried out for 1 cycle of 94° C. for 2 minutes (deactivation of anti-polymerase antibody) and 30 cycles each consisting of 94° C. for 15 seconds (denaturation), 50° C. for 30 seconds (annealing), and 68° C. for 2 minutes and 30 seconds (extension).

The total amount of the solution obtained by PCR was electrophoresed with 1% agarose, so that an approximately 1.4-kbp DNA fragment was confirmed. The fragment was purified by the use of GeneElute MINUS EtBr SPIN COLUMNS (Sigma) and ethanol precipitation, and then dissolved in 10 µl of TE buffer, thereby preparing "DNA solution A."

Next, the following PCR was carried out. Oligo DNA primers used herein are T238X-Fw: CCTATCATCGC-CAACCCGTACNNNATCGGCGAGGTCACCATCGCT (SEQ ID NO: 18) and 3'-UTR: GTAATACGACTCACTAT-AGGGCGAA (SEQ ID NO: 19). The letter "N" in the sequence refers to any one of A, T, G, and C. A saturation mutation is introduced by "NNN" in T238X-Fw (SEQ ID NO: 18) into amino acid at position 167 of SEQ ID NO: 2. The DNA fragment obtained by PCR was the nucleotide sequence ranging from positions 1391 to 2875 of the nucleotide sequence shown in SEQ ID NO: 7, in which a random mutation had been introduced into 3 nucleotides (codon corresponding to amino acid at position 167 of SEQ ID NO: 2) following nucleotide at position 1412 by the sequence "NNN" derived from T238X-Fw (SEQ ID NO: 18). The composition of the reaction solution of the PCR is as follows: KOD plus DNA polymerase: 0.4 µl; 10×KOD plus buffer: 2 µl; 2 mM each dNTP mixture: 2 µl; 25 mM magnesium sulfate: 0.8 µl; T238X-Fw (SEQ ID NO: 18) (10 pmol/µl): 0.6 µl; 3'-UTR (SEQ ID NO: 19) (10 pmol/µl): 0.6 µl; plasmid pCLuRA-TDH3 solution (3.8 ng/µl): 1 µl; and sterile water: 12.6 µl. PCR was carried out for 1 cycle of 94° C. for 2 minutes (deactivation of anti-polymerase antibody) and 30 cycles each consisting of 94° C. for 15 seconds (denaturation), 59° C. for 30 seconds (annealing), and 68° C. for 2 minutes and 30 seconds (extension).

The total amount of the solution obtained by PCR was electrophoresed with 1% agarose, so that an approximately 1.5-kbp DNA fragment was confirmed. This fragment was purified by the use of GeneElute MINUS EtBr SPIN COLUMNS (Sigma) and ethanol precipitation, and then dissolved in 10 µl of TE buffer, thereby preparing "DNA solution B."

Furthermore, the following PCR was carried out using a mixture of equivalent amounts of DNA solution A and DNA solution B as a template. The DNA fragment that could be amplified by PCR was the nucleotide sequence ranging from positions 900 to 1813 of the nucleotide sequence shown in SEQ ID NO: 7, in which a mutation had been introduced at random into 3 nucleotides (codon corresponding to amino acid at position 167 of SEQ ID NO: 2) following nucleotide at position 1412 by the sequence "NNN" existing in the DNA molecule in DNA solution B. The composition of the reaction solution of the PCR is as follows: KOD plus DNA polymerase: 1 µl; 10×KOD plus buffer: 5 µl; 2 mM each dNTP mixture: 5 µl; 25 mM magnesium sulfate: 2 µl; mut-CLuc-F (SEQ ID NO: 8) (10 pmol/µl): 1.5 µl; mut-CLuc-NR2 (SEQ ID NO: 9) (10 pmol/µl): 1.5 µl; DNA solution A: 0.5 µl; DNA solution B: 0.5 µl; and sterile water: 33 µl. PCR was carried out for 1 cycle of 94° C. for 2 minutes (deactivation of anti-polymerase antibody) and 30 cycles each consisting of 94° C. for 15 seconds (denaturation), 53° C. for 30 seconds (annealing), and 68° C. for 1 minute (extension).

The total amount of the solution obtained by PCR was electrophoresed with 1% agarose, so that an approximately 900-bp DNA fragment was confirmed. The remaining PCR solution was purified by the use of GeneElute PCR Clean-Up Kit (Sigma) and ethanol precipitation and then dissolved in 25 µl of TE buffer, thereby preparing "DNA solution C."

Next, the *Saccharomyces cerevisiae* BY4743ΔPRB1 strain was transformed by the method described in Example 2 using a mixture of equivalent amounts of DNA solution C and "complementary N-region fragment" DNA solution, thereby constructing a T167 saturation mutant library.

As a result of screening of the T167 saturation mutant library by the method described in Example 2, T167K mutant (a clone having T167K mutant CLuc in which threonine at position 167 of the amino acid sequence shown in SEQ ID NO: 2 had been substituted with lysine; corresponding to a transformant having the 3$^{rd}$ mutant luciferase(s)). The plasmid retained by the mutant is hereinafter referred to as "pCLuRA-TDH3[T167K]."

As a result of measuring emission spectra by the method described in Example 2, the emission spectral peak of T167K mutant CLuc was 459 nm, indicating a shift to the longer wavelength side of 5 nm compared with that of wild-type CLuc.

Example 4

Construction of Plasmid pCLuRA-TDH3[αP21L,K375R]

Based on the plasmid pCLuRA-TDH3[K375R], a mutation was introduced into a portion (of the αCLuc gene) encoding the secretory signal peptide (amino acid sequence: SEQ ID NO: 3) of the α factor. Thus, a new plasmid "pCLuRA-TDH3[αP21L,K375R]" was constructed. In this plasmid, in addition to K375R mutation, proline at position 21 (of SEQ ID NO: 3 and SEQ ID NO: 6) had been substituted with leucine (this is herein after referred to as the "αP21L mutation"). The secretory signal peptide of the α factor having the αP21L mutation improves the secretion amount of the protein to be secreted, which has been linked to the C-terminal side, 7 fold or more. Introduction of the αP21L mutation increased the secretion amount of luciferase, resulting in enhanced luminescence intensity. Naturally CLuc encoded by the plasmid is K375R mutant CLuc. In addition, "plasmid pCLuRA-TDH3 [αP21L]" was a plasmid in which, with respect to the αCLuc gene of pCLuRA-TDH3, nucleotide cytosine at position 762 of SEQ ID NO: 7 had been substituted with nucleotide thymine, so as to cause substitution of proline at position 21 (of SEQ ID NO: 3 and SEQ ID NO: 6) with leucine.

A method for constructing pCLuRA-TDH3[αP21L, K375R] is as follows.

First the following PCR was carried out. The composition of the reaction solution of the PCR is as follows: KOD plus DNA polymerase: 0.4 μl; 10×KOD plus buffer: 2 μl; 2 mM each dNTP mixture: 2 μl; 25 mM magnesium sulfate: 0.8 μl; mut-CLuc-CF1 (SEQ ID NO: 12) (10 pmol/μl): 0.6 μl; mut-CLuc-R (SEQ ID NO: 13) (10 pmol/μl): 0.6 μl; plasmid pCLuRA-TDH3[K375R] solution (1 ng/μl): 1 μl; and sterile water: 12.6 μl. PCR was carried out for 1 cycle of 94° C. for 2 minutes (deactivation of anti-polymerase antibody) and 30 cycles each consisting of 94° C. for 15 seconds (denaturation), 53° C. for 30 seconds (annealing), and 68° C. for 1 minute and 15 seconds (extension).

The total amount of the solution obtained by PCR was electrophoresed with 1% agarose, so that an approximately 1-kbp DNA fragment was confirmed. This fragment was purified by the use of GeneElute MINUS EtBr SPIN COLUMNS (Sigma) and ethanol precipitation and then dissolved in 10 μl of TE buffer, thereby preparing "DNA solution D." The fragment corresponds to a nucleotide sequence (containing a nucleotide substitution involved in K375R amino acid substitution) ranging from positions 1554 to 2663 of the nucleotide sequence shown in SEQ ID NO: 7.

Subsequently, the following PCR was carried out. The composition of the reaction solution of the PCR is as follows: KOD plus DNA polymerase: 0.4 μl; 10×KOD plus buffer: 2 μl; 2 mM each dNTP mixture: 2 μl; 25 mM magnesium sulfate: 0.8 μl; vec-CLuc-F (SEQ ID NO: 14) (10 pmol/μl): 0.6 μl; SQ-CLuc-CR1 (SEQ ID NO: 15) (10 pmol/μl): 0.6 μl; plasmid pCLuRA-TDH3[αP21L] solution (1 ng/μl): 1 μl; and sterile water: 12.6 μl. PCR was carried out for 1 cycle of 94° C. for 2 seconds (deactivation of anti-polymerase antibody) and 30 cycles each consisting of 94° C. for 15 seconds (denaturation), 53° C. for 30 seconds (annealing), and 68° C. for 8 minutes (extension).

The total amount of the solution obtained by PCR was electrophoresed with 1% agarose, so that an approximately 6.5-kbp DNA fragment was confirmed. This fragment was purified by the use of GeneElute MINUS EtBr SPIN COLUMNS (Sigma) and ethanol precipitation and then dissolved in 10 μl of TE buffer, thereby preparing "DNA solution E." The fragment corresponds to, in the nucleotide sequence of the plasmid pCLuRA-TDH3[αP21L], a nucleotide sequence lacking a region ranging from positions 1664 to 2575 of the nucleotide sequence shown in SEQ ID NO: 7.

Next, the *Saccharomyces cerevisiae* BY4743ΔPRB1 strain was transformed by the method described in Example 2 using a mixture of equivalent amounts of DNA solution D and DNA solution E, thereby causing colony formation. A DNA fragment contained in DNA solution D and the same contained in DNA solution E share the nucleotide sequence ranging from positions 1554 to 1663 and the nucleotide sequence ranging from positions 2576 to 2663 of the nucleotide sequence shown in SEQ ID NO: 7.

One of the thus obtained colonies was cultured and then DNA containing the plasmid was extracted and purified from the microorganisms. *Escherichia coli* DH5α was transformed using the DNA and then caused to undergo colony formation. One of the thus obtained colonies was cultured and then plasmid DNA was extracted and purified by a conventional method. The nucleotide sequence ranging from positions 1 to 2875 of the nucleotide sequence shown in SEQ ID NO: 7 was examined. Thus, the occurrence of a desired nucleotide substitution was confirmed, thereby preparing pCLuRA-TDH3 [αP21L,K375R].

Example 5

T405I Mutant CLuc

A new mutant CLuc gene library was constructed by the method described in Example 2. However, as a template for PCR, pCLuRA-TDH3[αP21L] was used instead of plasmid pCLuRA-TDH3. As a result of screening by the method described in Example 2, a clone (corresponding to a transformant having the 5$^{th}$ mutant luciferase) was obtained, having T405I mutant CLuc in which threonine at position 405 had been substituted with isoleucine with respect to the amino acid sequence shown in SEQ ID NO: 2.

As a result of measuring emission spectra by the method described in Example 2, the emission spectral peak of T405I mutant CLuc was 458 nm, indicating a shift to the longer wavelength side of 4 nm compared with that of wild-type CLuc. The plasmid retained by the T405I mutant is hereinafter referred to as "pCLuRA-TDH3[αP21L,T405I]."

Example 6

CLuc Labeled with Histidine Tag

To facilitate the purification of CLuc secreted in a culture supernatant, a plasmid "pCLuRA-TDH3[αP21L,-(GS) 3H6]" was constructed, in which a histidine tag was fused to the C-terminus and αCLuc (SEQ ID NO: 20) containing αP21L mutation was expressed. SEQ ID NO: 23 is a partial nucleotide sequence of the plasmid pCLuRA-TDH3 [αP21L,-(GS)3H6].

The construction method is as follows.

First, the following PCR was carried out using pCLuRA-TDH3 as a template. Oligo DNA primers used herein are CLuc (GS)3H6-F: CACCACCATCACCACCATTAGTCTA-GAGGGCCGCATCATGTAATT (SEQ ID NO: 21) and CLuc (GS)3H6-R: AGAACCAGAACCAGAACCTTTG-CATTCATCTGGTACTTCTAGGGT (SEQ ID NO: 22). The composition of the reaction solution of the PCR is as follows: KOD plus DNA polymerase: 1 µl; 10×KOD plus buffer: 5 µl; 2 mM each dNTP mixture: 5 µl; 25 mM magnesium sulfate: 2 µl; CLuc (GS)3H6-F (SEQ ID NO: 21) (10 pmol/µl): 1.5 µl; CLuc (GS)3H6-R (SEQ ID NO: 22) (10 pmol/µl): 1.5 µl; plasmid pCLuRA-TDH3 solution (10 ng/µl): 0.1 µl; and sterile water: 34 µl. PCR was carried out for 1 cycle of 94° C. for 2 minutes (deactivation of anti-polymerase antibody) and 30 cycles each consisting of 94° C. for 15 seconds (denaturation), 48° C. for 30 seconds (annealing), and 68° C. for 8 minutes (extension).

The total amount of the solution obtained by PCR was electrophoresed with 1% agarose, so that an approximately 7.5-kbp DNA fragment was confirmed. This fragment was purified by the use of GeneElute MINUS EtBr SPIN COLUMNS (Sigma) and ethanol precipitation.

Next, both 5' ends of the thus obtained DNA fragments were phosphorylated using T4 polynucleotide kinase. They were ligated as DNA substrates using T4 DNA ligase for circularization. *Escherichia coli* DH5α was transformed using the circularized DNA. A plasmid was extracted and purified by a conventional method from the transformed *Escherichia coli*. The plasmid was subjected to double digestion with EcoR I and Xba I and then the digest was separated by agarose gel electrophoresis. Next, an approximately 1.1-kbp fragment containing a region encoding a histidine tag was purified by the use of GeneElute MINUS EtBr SPIN COLUMNS (Sigma) and ethanol precipitation (DNA fragment G).

Meanwhile, pCLuRA-TDH3[αP21L] was subjected to double digestion with EcoR I and Xba I and then the digest was separated by agarose electrophoresis. An approximately 6.5-kbp fragment was similarly purified (DNA fragment H).

Next, DNA fragment G and DNA fragment H were ligated as DNA substrates using T4 DNA ligase and then *Escherichia coli* DH5α was transformed with the resultant. The plasmid was extracted and purified by a conventional method from the transformed *Escherichia coli*. The thus obtained plasmid was subjected to examination of the nucleotide sequence (ranging from positions 1 to positions 2875 of SEQ ID NO: 23), so as to confirm that the sequence was the desired nucleotide sequence. Thus, pCLuRA-TDH3[αP21L,-(GS)3H6] was prepared.

Furthermore, the *Saccharomyces cerevisiae* BY4743ΔPRB1 strain was transformed according to the method described in Example 2 using pCLuRA-TDH3 and pCLuRA-TDH3[αP21L,-(GS)3H6] separately. Wild-type CLuc and CLuc labeled with a histidine tag were each secreted and then each emission spectrum was measured according to the method described in Example 2. As a result, no difference was observed in emission spectrum between the two. Specifically, it was confirmed that no difference in emission spectrum is caused due to the presence or the absence of a histidine tag.

Example 7

A Group of Mutant CLuc, each Having a Substitution of Lysine Corresponding to Amino Acid at Position 375 of SEQ ID NO: 2 with Another Amino Acid 7-1. Plasmid for Expression of a Group of Mutant Cluc Each Having a Substitution of Lysine Corresponding to Amino Acid at Position 375 with Another Amino Acid As described in Example 2, substitution of lysine corresponding to amino acid at position 375 of SEQ ID NO: 2 with arginine or glutamic acid results in a shift of the emission spectral peak to the longer wavelength side. Hence, a group of plasmids was constructed by the methods described in the following sections 7-2 and 7-3 for secretion and expression of a group of mutant CLuc (and wild-type CLuc) in which amino acid at position 375 was one of 20 types of amino acid composing general proteins.

7-2. Construction 1 of Expression Plasmid

Saturation mutant libraries of amino acid corresponding to amino acid at position 375 of SEQ ID NO: 2 were constructed by 4 types of PCR and intracellular recombination, as follows.

(1) PCR1

Oligo DNA primers used herein are K446X-F: TGAAGTAGAGAAAGTACGAATCAGGNNNCAATCGACTGTAGTAGTAGAACTCA (SEQ ID NO: 24) and mut-CLuc-R (SEQ ID NO: 13). The composition of the reaction solution of the PCR is as follows: KOD plus DNA polymerase: 0.4 µl; 10×KOD plus buffer: 2 µl; 2 mM each dNTP mixture: 2 µl; 25 mM magnesium sulfate: 0.8 µl; K446X-F (SEQ ID NO: 24) (10 pmol/µl): 0.6 µl; mut-CLuc-R (SEQ ID NO: 13) (10 pmol/µl): 0.6 µl; plasmid pCLuRA-TDH3 [αP21L,-(GS)3H6] solution (1 ng/µl): 1 µl; and sterile water: 12.6 µl. PCR was carried out for 1 cycle of 94° C. for 2 minutes (deactivation of anti-polymerase antibody) and 30 cycles of 94° C. for 15 seconds (denaturation), 45° C. for 30 seconds (annealing), and 68° C. for 1 minute and 30 seconds (extension).

The total amount of the solution obtained by PCR was electrophoresed with 1% agarose, so that an approximately 700-bp DNA fragment was confirmed. The fragment was purified by the use of GeneElute MINUS EtBr SPIN COLUMNS (Sigma) and ethanol precipitation, and then dissolved in 10 µl of TE buffer, thereby preparing "DNA solution J."

(2) PCR2

Oligo DNA primers used herein are K446-R: CCTGATTCGTACTTTCTCTACTTCA (SEQ ID NO: 25) and mut-CLuc-F (SEQ ID NO: 8). The composition of the reaction solution of the PCR is as follows: KOD plus DNA polymerase: 0.4 µl; 10×KOD plus buffer: 2 µl; 2 mM each dNTP mixture: 2 µl; 25 mM magnesium sulfate: 0.8 µl; K446-R (SEQ ID NO: 25) (10 pmol/µl): 0.6 µl; mut-CLuc-F (SEQ ID NO: 8) (10 pmol/µl): 0.6 µl; plasmid pCLuRA-TDH3 [αP21L,-(GS) 3H6] solution (1 ng/µl): 1 µl; and sterile water: 14.6 µl. PCR was carried out for 1 cycle of 94° C. for 2 minutes (deactivation of anti-polymerase antibody) and 30 cycles each consisting of 94° C. for 15 seconds (denaturation), 45° C. for 30 seconds (annealing), and 68° C. for 1 minute and 30 seconds (extension).

The total amount of the solution obtained by PCR was electrophoresed with 1% agarose, so that an approximately 1.1-kbp DNA fragment was confirmed. The fragment was purified by the use of GeneElute MINUS EtBr SPIN COLUMNS (Sigma) and ethanol precipitation, and then dissolved in 10 µl of TE buffer, thereby preparing "DNA solution K."

(3) PCR3

Oligo DNA primers used herein are mut-CLuc-F (SEQ ID NO: 8) and mut-CLuc-R: (SEQ ID NO: 13). The composition of the reaction solution of the PCR is as follows: KOD plus DNA polymerase: 1 µl; 10×KOD plus buffer: 5 µl; 2 mM each dNTP mixture: 5 µl; 25 mM magnesium sulfate: 2 µl; mut-CLuc-F (SEQ ID NO: 8) (10 pmol/µl): 1.5 µl; mut-CLuc-R (SEQ ID NO: 13) (10 pmol/µl): 1.5 µl; DNA solution J: 1 µl; DNA solution K: 1 µl; and sterile water: 33 µl. PCR was carried out for 1 cycle of 94° C. for 2 minutes (deactivation of anti-polymerase antibody) and 30 cycles each consisting of 94° C. for 15 seconds (denaturation), 50° C. for 30 seconds (annealing), and 68° C. for 2 minutes and 20 seconds (extension).

The total amount of the solution obtained by PCR was electrophoresed with 1% agarose, so that an approximately 1.8-kbp DNA fragment was confirmed. The fragment was purified by the use of GeneElute MINUS EtBr SPIN COLUMNS (Sigma) and ethanol precipitation, and then dissolved in 50 µl of TE buffer, thereby preparing "DNA solution L."

(4) PCR4

Oligo DNA primers used herein are vec-CLuc-F (SEQ ID NO: 14) and vec-CLuc-R: (SEQ ID NO: 10). The composition of the reaction solution of the PCR is as follows: KOD plus DNA polymerase: 1 µl; 10×KOD plus buffer: 5 µl; 2 mM each dNTP mixture: 5 µl; 25 mM magnesium sulfate: 2 µl; vec-CLuc-F (SEQ ID NO: 14) (10 pmol/µl): 1.5 µl; vec-CLuc-R (SEQ ID NO: 10) (10 pmol/µl): 1.5 µl; plasmid pCLuRA-TDH3[αP21L,-(GS)3H6] solution (1 ng/µl): 1 µl; and sterile water: 34 µl. PCR was carried out for 1 cycle of 94° C. for 2 minutes (deactivation of anti-polymerase antibody) and 30 cycles each consisting of 94° C. for 15 seconds (denaturation), 50° C. for 30 seconds (annealing), and 68° C. for 7 minutes (extension).

The total amount of the solution obtained by PCR was electrophoresed with 1% agarose, so that an approximately 6-kbp DNA fragment was confirmed. The fragment was purified by the use of GeneElute MINUS EtBr SPIN COLUMNS (Sigma) and ethanol precipitation, and then dissolved in 50 µl of TE buffer, thereby preparing "DNA solution M."

Next, the Saccharomyces cerevisiae BY4743ΔPRB1 strain was transformed using a mixture of equivalent amounts of DNA solution L and DNA solution M and then caused to form colonies. The thus obtained 96 colonies were cultured separately in a buffered SD-ura liquid medium and then DNA containing the plasmid was extracted and purified from each of the media. Escherichia coli DH5α was transformed with these DNA samples. Plasmid DNAs were extracted and purified from the thus obtained Escherichia coli transformants according to a conventional method and then the nucleotide sequences were examined.

As a result, plasmids were obtained in which codons encoding amino acid corresponding to amino acid at position 375 of SEQ ID NO: 2 were codons encoding the following amino acids: alanine, cysteine, aspartic acid, glutamic acid, glycine, isoleucine, lysine, leucine, methionine, asparagine, glutamine, arginine, serine, threonine, valine, tryptophan, and tyrosine. The plasmids were in turn referred to as "pCLuRA-TDH3[αP21L,K375A,-(GS)3H6]," "pCLuRA-TDH3[αP21L,K375C,-(GS)3H6]," "pCLuRA-TDH3[αP21L,K375D,-(GS)3H6]," "pCLuRA-TDH3[αP21L,K375E,-(GS) 3H6]," "pCLuRA-TDH3[αP21L,K375G,-(GS)3H6]," "pCLuRA-TDH3[αP21L,K375I,-(GS)3H6]," "pCLuRA-TDH3[αP21L,K375K,-(GS)3H6]," "pCLuRA-TDH3[αP2 µL,K375L,-(GS)3H6]," "pCLuRA-TDH3[αP21L,K375M,-(GS) 3H6]," "pCLuRA-TDH3[αP21L,K375N,-(GS)3H6]," "pCLuRA-TDH3[αP21L,K375Q,-(GS)3H6]," "pCLuRA-TDH3[αP21L,K375R,-(GS)3H6]," "pCLuRA-TDH3[αP21L,K375S,-(GS)3H6]," "pCLuRA-TDH3[αP21L,K375T,-(GS) 3H6]," "pCLuRA-TDH3[αP21L,K375V,-(GS)3H6]," "pCLuRA-TDH3[αP21L,K375W,-(GS)3H6]," and "pCLuRA-TDH3[αP21L,K375Y,-(GS)3H6]," respectively.

7-3. Construction 2 of Expression Plasmid pCLuRA-TDH3[αP21L,K375F,-(GS)3H6] that was a plasmid in which the codon encoding the amino acid corresponding to amino acid at position 375 of SEQ ID NO: 2 was a codon encoding phenylalanine was constructed as follows.

PCR was carried out using pCLuRA-TDH3[αP21L,-(GS)3H6] as a template. Oligo DNA primers used herein are K446F: TTTCAATCGACTGTAGTAGAACTCA (SEQ ID NO: 26) and K446-R: CCTGATTCGTACTTTCTCTACT-TCA (SEQ ID NO: 25). The composition of the reaction solution for the PCR is as follows: KOD plus DNA polymerase: 0.4 µl; 10×KOD plus buffer: 2 µl; 2 mM each dNTP mixture: 2 µl; 25 mM magnesium sulfate: 0.8 µl; K446F (SEQ ID NO: 26) (10 pmol/µl): 0.6 µl; K446-R (SEQ ID NO: 25) (10 pmol/µl): 0.6 µl; plasmid pCLuRA-TDH3[αP21L,-(GS) 3H6] solution (1 ng/µl): 1 µl; and sterile water: 12.6 µl. PCR was carried out for 1 cycle of 94° C. for 2 minutes (deactivation of anti-polymerase antibody) and 30 cycles each consisting of 94° C. for 15 seconds (denaturation), 48° C. for 30 seconds (annealing), and 68° C. for 8 minutes (extension).

The total amount of the solution obtained by PCR was electrophoresed with 1% agarose, so that an approximately 7.5-kbp DNA fragment was confirmed. The fragment was purified by the use of GeneElute MINUS EtBr SPIN COLUMNS (Sigma) and ethanol precipitation.

Both 5' ends of the thus obtained DNA fragments were phosphorylated by T4 polynucleotide kinase. They were ligated as DNA substrates using T4 DNA ligase for circularization. Escherichia coli DH5α was transformed using the circularized DNA. The plasmid was extracted and purified by a conventional method from the transformed Escherichia coli. The plasmid was subjected to double digestion with BamH I and Xba I and then the digest was separated by agarose electrophoresis. Furthermore, an approximately 2.6-kbp fragment containing a region encoding αCLuc in which the codon encoding the amino acid corresponding to amino acid at position 375 of SEQ ID NO: 2 had been altered was purified by the use of GeneElute MINUS EtBr SPIN COLUMNS (Sigma) and ethanol precipitation (DNA fragment N).

Meanwhile, pCLuRA-TDH3[αP21L,-(GS)3H6] was subjected to double digestion with BamH I and Xba I and then the digest was separated by agarose gel electrophoresis. An approximately 5-kbp fragment was similarly purified (DNA fragment P).

Next, DNA fragment N and DNA fragment P were ligated as DNA substrates using T4 DNA ligase. Escherichia coli DH5α was transformed with the resultant. A plasmid was extracted and purified by a conventional method from the thus transformed Escherichia coli. The thus obtained plasmid was subjected to examination of the nucleotide sequence (the sequence ranging from positions 1 to 2875 of SEQ ID NO: 23), so as to confirm that the sequence was the desired nucleotide sequence. Thus, pCLuRA-TDH3[αP21L,K375F,-(GS) 3H6] was prepared.

Plasmids (referred to as "pCLuRA-TDH3[αP21L,K375H,-(GS)3H6]" and "pCLuRA-TDH3[αP21L,K375P,-(GS)3H6]," respectively) were constructed, in which the codon encoding the amino acid corresponding to amino acid at position 375 of SEQ ID NO: 2 had been substituted with the codon encoding histidine or proline. The construction method employed for them was the same as that employed for construction of pCLuRA-TDH3[αP21L,K375F,-(GS)3H6], except for the use of different oligo DNA primers for PCR. Oligo DNA primers used for construction of pCLuRA-TDH3[αP21L,K375H,-(GS)3H6] are K446H: CATCAATCGACT-GTAGTAGAACTCA (SEQ ID NO: 27) and K446-R (SEQ ID NO: 25). Meanwhile, oligo DNA primers used for construction of pCLuRA-TDH3[αP21L,K375P,-(GS)3H6] are K446P: CCACAATCGACTGTAGTAGAACTCA (SEQ ID NO: 28) and K446-R (SEQ ID NO: 25).

7-4. Emission Spectra of a Group of mutant CLuc Having a Substitution of Lysine Corresponding to Position 375 of SEQ ID NO: 2 with Another Amino Acid The *Saccharomyces cerevisiae* BY4743ΔPRB1 strain was transformed with each of 20 types of plasmid obtained in the sections 7-2 and 7-3 above. CLuc secreted by *Saccharomyces cerevisiae* that had been transformed with the plasmid pCLuRA-TDH3[αP21L,K375K,-(GS)3H6] was wild-type CLuc. CLuc secreted by *Saccharomyces cerevisiae* that had been transformed with each of 19 types of plasmid other than the plasmid was mutant CLuc. They were each cultured by the method described in Example 2 and then emission spectra were measured using the culture supernatants.

Table 1 shows maximum emission spectral wavelengths of the wild-type CLuc and each mutant CLuc.

TABLE 1

| Mutant CLuc | Maximum emission spectral wavelength (nm) |
|---|---|
| Wild type | 454 |
| K375A | 462 |
| K375C | 461 |
| K375D | 461 |
| K375E | 462 |
| K375F | 461 |
| K375G | 460 |
| K375H | 461 |
| K375I | 462 |
| K375L | 462 |
| K375M | 461 |
| K375N | 462 |
| K375P | 459 |
| K375Q | 461 |
| K375R | 463 |
| K375S | 462 |
| K375T | 462 |
| K375V | 463 |
| K375W | 462 |
| K375Y | 457 |

As shown in Table 1, surprisingly, whereas the maximum emission spectral wavelength was 454 nm in the case of the wild-type CLuc, the maximum emission spectral wavelength was 457 nm or more in all the other cases of mutant CLuc. Specifically, all of the mutant CLucs listed in Table 1 were the $1^{st}$ mutant luciferases (K375A mutant CLuc, K375C mutant CLuc, K375D mutant CLuc, K375E mutant CLuc, K375F mutant CLuc, K375G mutant CLuc, K375H mutant CLuc, K375I mutant CLuc, K375L mutant CLuc, K375M mutant CLuc, K375N mutant CLuc, K375P mutant CLuc, K375Q mutant CLuc, K375R mutant CLuc, K375S mutant CLuc, K375T mutant CLuc, K375V mutant CLuc, K375W mutant CLuc, and K375Y mutant CLuc).

Example 8

Construction of N404 Saturation Mutant Library and Screening for Mutant CLuc 8-1. Construction of N404 Saturation Mutant Library A mutant library was constructed in which amino acid at position 404 of the amino acid sequence shown in SEQ ID NO: 2 was substituted any one of the other amino acids.

The nucleotide sequence ranging from positions 1 to 2122 of SEQ ID NO: 7 was amplified by PCR. Hereinafter, the DNA fragment is referred to as "fragment a(475)."

The following oligo DNA primers were used for PCR for amplification of fragment a(475): FAR-F (SEQ ID NO: 16) and N475-rev:ctgagagctgtacgggacgga (SEQ ID NO: 29). Furthermore, the composition of the reaction solution for PCR for amplification of fragment a(475) is as follows: KOD plus DNA polymerase (TOYOBO Co., Ltd.): 0.4 μl; pCLuRA-TDH3 plasmid solution (3.8 ng/μl): 1 μl; 10×KOD plus buffer: 2 μl; 2 mM each dNTP mixture: 2 μl; 25 mM magnesium sulfate: 0.8 μl; FAR-F (SEQ ID NO: 16): 0.6 μl (10 pmol/μl); N475-rev (SEQ ID NO: 29): 0.6 μl (10 pmol/μl); and sterile water: 13.6 μl. PCR was carried out for 1 cycle of 94° C. for 2 minutes (deactivation of anti-polymerase antibody) and 30 cycles each consisting of 94° C. for 15 seconds (denaturation), 49° C. for 30 seconds (annealing), and 68° C. for 2 minutes and 30 seconds (extension).

Meanwhile, the nucleotide sequence ranging from positions 2102 to 2875 of SEQ ID NO: 7 was amplified by PCR. Hereinafter, the DNA fragment is referred to as "fragment b(475X)."

The following oligo DNA primers were used for PCR for amplification of fragment b(475X): N475X-Fw: tccgtcccgta-cagctctcagnnnacttccatctactggcaagat (SEQ ID NO: 30) and 3'-UTR (SEQ ID NO: 19). Furthermore, the composition of the reaction solution for PCR for amplification of fragment b(475X) was the same as that employed for amplification of fragment a(475) except for primers. The PCR reaction conditions were the same as those employed for amplification of fragment a(475) except for annealing temperature. The annealing temperature employed herein was 50° C.

The thus obtained PCR products of fragment a(475) and fragment b(475X) were electrophoresed with 1% agarose, so that an approximately 2100-bp fragment a(475) and an approximately 800-bp fragment b(475X) could be confirmed. They were mixed and then subjected to purification using GeneElute MINUS EtBr SPIN COLUMNS (Sigma), phenol extraction, and then ethanol precipitation. The resultant was dissolved in 10 μl of sterile water (the mixed solution of fragments a(475) and b(475X)).

Next, overlap PCR was carried out using the above mixed solution of fragments a(475) and b(475X), as a template. Thus, one long fragment (the nucleotide sequence ranging from positions 1554 to 2663 of SEQ ID NO: 7) was prepared, in which the codon at target mutation position was substituted with NNN. Hereinafter, the DNA fragment is referred to as "fragment c(475X)."

The following oligo DNA primers were used for PCR for amplification of fragment c(475X): mut-CLuc-CF1 (SEQ ID NO: 12) and mut-CLuc-R (SEQ ID NO: 13). Furthermore, the composition of the reaction solution for PCR for amplification of fragment c(475X) is as follows: KOD plus DNA polymerase (TOYOBO Co., Ltd.): 1 μl; a mixed solution of fragments a(475) and b(475X): 1 μl; 10×KOD plus buffer: 5 μl; 2 mM each dNTP mixture: 5 μl; 25 mM magnesium sulfate: 2 μl; mut-CLuc-CF1 (SEQ ID NO: 12): 1.5 μl (10 pmol/μl); mut-CLuc-R (SEQ ID NO: 13): 1.5 μl (10 pmol/μl); and sterile water: 33 μl. PCR was carried out for 1 cycle of 94° C. for 2 minutes (deactivation of anti-polymerase antibody) and 30 cycles each consisting of 94° C. for 15 seconds (denaturation), 61° C. for 30 seconds (annealing), and 68° C. for 1 minute (extension).

Meanwhile, a linear DNA fragment lacking the nucleotide sequence ranging from positions 1664 to 2575 of SEQ ID NO: 7 in the sequence of pCLuRA-TDH3 was amplified by PCR. Hereinafter, the DNA fragment is referred to as "fragment d."

The following oligo DNA primers were used for PCR for amplification of fragment d: SQ-CLuc-CR1 (SEQ ID NO: 15) and vec-CLuc-F (SEQ ID NO: 14). Furthermore, the composition of the reaction solution for PCR for amplification of fragment d was the same as that employed for amplification of fragment c(475X), except for template DNA and oligo DNA primers. The following template DNA was used: pCLuRA-TDH3 plasmid solution (3.8 ng/µl) (11). The PCR reaction conditions were the same as those employed for amplification of fragment c(475X), except for annealing temperature and extension time. The annealing temperature was 58° C. and the extension time was 8 minutes.

The thus obtained PCR products of fragment c(475X) and fragment d were electrophoresed with 0.7% agarose, so that an approximately 11100-bp fragment c(475X) and an approximately 7000-bp fragment d could be confirmed. They were mixed and then subjected to purification using GeneElute MINUS EtBr SPIN COLUMNS (Sigma), phenol extraction, and then ethanol precipitation. The resultant was dissolved in 10 µl of sterile water (a mixed solution of fragments c(475X) and d).

Next, the *Saccharomyces cerevisiae* BY4743Δprb1 strain was transformed by the lithium acetate method using 10 µl of the mixed solution of fragments c(475X) and d. An SD-Ura agar medium was coated with the resultant, followed by approximately 48 hours of incubation at 30° C. Many colonies that had thus appeared were named "N404 saturation mutant libraries."

8-2. Screening for Luciferase with an Altered (Shifted) Emission Spectrum and an Amino Acid Mutation at Position 404 of SEQ Id No: 2 and Measurement of an Emission Spectrum Hereafter, clones suspected of having undergone emission spectral shift were selected by the method same as that employed for the sections 2.3 and 2.4 in Example 2 and then the emission spectra were measured.

As shown in Table 2 below, the emission spectral peaks of the thus selected N404G mutant CLuc and N404S mutant CLuc (the 4$^{th}$ mutant luciferases) were both found to be 458 nm. pCLuRA-TDH3 plasmid that had, with respect to the amino acid sequence shown of SEQ ID NO: 2, a substitution (mutation) of asparagine at position 404 with glycine is defined as "pCLuRA-TDH3[N404G]."

Example 9

Construction of T405 Saturation Mutant Library and Screening for Mutant CLuc

A mutant library was constructed, in which amino acid at position 405 of the amino acid sequence shown in SEQ ID NO: 2 was substituted with any one of the other amino acids. The method for construction is similar to that in Example 8.

The nucleotide sequence ranging from positions 1 to 2125 of SEQ ID NO: 7 was amplified by PCR. The DNA fragment is hereinafter referred to as "fragment a(476)."

The following oligo DNA primers were used for PCR for amplification of fragment a(476): FAR-F (SEQ ID NO: 16) and T476-rev: gttctgagagctgtacgggac (SEQ ID NO: 31). Furthermore, the composition of the reaction solution for PCR for amplification of fragment a(476) was the same as that employed for amplification of fragment a(475) in Example 8, except for primers. The PCR reaction conditions were the same as those employed for amplification of fragment a(475) in Example 8, except for annealing temperature. Annealing was carried out at 59° C.

Meanwhile, the nucleotide sequence ranging from positions 2105 to 2875 of SEQ ID NO: 7 was amplified by PCR. The DNA fragment is hereinafter referred to as "fragment b(476X)."

The following oligo DNA primers were used for PCR for amplification of fragment b(476X): T476X-Fw: gtcccgtacagctctcagaacnnntccatctactggcaagatggt (SEQ ID NO: 32) and 3'-UTR (SEQ ID NO: 19). Furthermore, the composition of the reaction solution for amplification of fragment b(476X) was the same as that employed for amplification of fragment b(475X) in Example 8, except for primers. The PCR conditions were the same as those employed for amplification of fragment b(475X) in Example 8.

Then, a mixed solution of fragments a(476) and b(476X) was prepared in a manner similar to that in Example 8.

Overlap PCR was carried out using the above mixed solution of fragments a(476) and b(476X) as a template. Thus, one long fragment (the nucleotide sequence ranging from positions 1554 to 2663 of SEQ ID NO: 7) was prepared, in which the codon at target mutation position was substituted with NNN. Hereinafter, the DNA fragment is referred to as "fragment c(476X)."

The composition of the reaction solution for PCR for amplification of fragment c(476X) was the same as that employed for amplification of fragment c(475X) in Example 8, except for template DNA. The following template DNA was used: the mixed solution (1 µl) of fragments a(476) and b(476X). The PCR conditions were the same as those employed for amplification of fragment c(475X) in Example 8.

Moreover, a mixed solution of fragments c (476X) and d was prepared in a manner similar to that in Example 8.

Next, clones suspected of having undergone emission spectral shift were selected in a manner similar to that in Example 8 using 10 µl of the mixed solution of fragments c(476X) and d (Example 8). The emission spectra of the thus obtained clones were measured.

As shown in Table 2, the emission spectral peak of the thus selected T405M mutant CLuc (the 5$^{th}$ mutant luciferase) was 457 nm.

Example 10

Construction of S406 Saturation Mutant Library and Screening for Mutant CLuc

A mutant library was constructed, in which amino acid at position 406 of the amino acid sequence shown in SEQ ID NO: 2 was substituted with any one of the other amino acids. The construction method is similar to that in Example 8.

The nucleotide sequence ranging from positions 1 to 2128 of SEQ ID NO: 7 was amplified by PCR. The DNA fragment is referred to as "fragment a(477)."

The following oligo DNA primers were used for PCR for amplification of fragment a(477): FAR-F (SEQ ID NO: 16) and S477-rev: agtgttctgagagctgtacgg (SEQ ID NO: 33). Furthermore, the composition of the reaction solution for PCR for amplification of fragment a(477) was the same as that employed for amplification of fragment a(475) in Example 8, except for primers. The PCR conditions were the same as those employed for amplification of fragment a(475) in Example 8.

Meanwhile, the nucleotide sequence ranging from positions 2108 to 2875 of SEQ ID NO: 7 was amplified by PCR. The fragment is hereinafter referred to as "fragment b (477X)."

The following oligo DNA primers were used for PCR for amplification of fragment b(477X): S477X-Fw: ccgtacagctctcagaacactnnnatctactggcaagatggtgac (SEQ ID NO: 34) and 3'-UTR (SEQ ID NO: 19). The composition of the reaction solution for PCR for amplification of fragment b(477X) was the same as that employed for amplification of fragment b(475X) in Example 8 except for primers. The PCR conditions were the same as those employed for amplification of fragment b(475X) in Example 8.

Next, a mixed solution of fragments a(477) and b(477X) was prepared in a manner similar to that in Example 8.

Furthermore, overlap PCR was carried out using the above mixed solution of fragments a(477) and b(477X) as a template. Thus, one long fragment (the nucleotide sequence ranging from positions 1554 to 2663 of SEQ ID NO: 7) was prepared, in which the codon at target mutation position was substituted with NNN. Hereinafter, the DNA fragment is referred to as "fragment c(477X)."

The composition of the reaction solution for PCR for amplification of fragment c(477X) was the same as that employed for amplification of fragment c(475X) in Example 8 except for template DNA. The following template DNA was used: the mixed solution (1 μl) of fragments a(477) and b(477X). The PCR conditions employed herein were the same as those in Example 8.

Furthermore, a mixed solution of fragments c(477X) and d (Example 8) was prepared in a manner similar to that in Example 8.

Next, clones suspected of having undergone emission spectral shift were selected in a manner similar to that in Example 8 using 10 μl of the mixed solution of fragments c(477X) and d. The emission spectra of the thus obtained clones were then measured.

As shown in Table 2, the emission spectral peak of the thus selected S406L mutant CLuc (the $6^{th}$ mutant luciferase) was 460 nm.

Example 11

Construction of I407 Saturation Mutant Library and Screening for Mutant CLuc

A mutant library was constructed, in which amino acid at position 407 of the amino acid sequence shown in SEQ ID NO: 2 was substituted with any one of the other amino acids. The construction method was similar to that in Example 8.

The nucleotide sequence ranging from positions 1 to 2131 of SEQ ID NO: 7 was amplified by PCR. The DNA fragment is referred to as "fragment a(478)."

The following oligo DNA primers were used for PCR for amplification of fragment a(478): FAR-F (SEQ ID NO: 16) and I478-rev: ggaagtgttctgagagctgta (SEQ ID NO: 35). Furthermore, the composition of the reaction solution for PCR for amplification of fragment a(478) was the same as that in reaction conditions employed for amplification of fragment a(475) in Example 8 except for primers. The PCR conditions were the same as those employed for amplification of fragment a(475) in Example 8, except for annealing temperature. Annealing was carried out at 55° C.

Meanwhile, the nucleotide sequence ranging from positions 2111 to 2875 of SEQ ID NO: 7 was amplified by PCR. The DNA fragment is referred to as "fragment b(478X)."

The following oligo DNA primers were used for PCR for amplification of fragment b(478X): I478X-Fw: tacagctctcagaacacttccnnnntactggcaagatggtgacata (SEQ ID NO: 36) and 3'-UTR (SEQ ID NO: 19). Furthermore, the composition of the reaction solution for PCR for amplification of fragment b(478X) was the same as that employed for amplification of fragment b(475X) in Example 8, except for primers. The PCR conditions were the same as those employed for amplification of fragment b(475X) in Example 8, except for annealing temperature. Annealing was carried out at 58° C.

The thus obtained PCR products of fragment a(478) and fragment b(478X) were electrophoresed with 1% agarose, so that an approximately 2100-bp fragment a(478) and an approximately 800-bp fragment b(478X) could be confirmed. They were mixed and then subjected to purification using Wizard (trademark) SV Gel and PCR Clean-Up system (Promega), phenol extraction, and then ethanol precipitation. The resultant was dissolved in 10 μl of sterile water (a mixed solution of fragments a(478) and b(478X)).

Next, overlap PCR was carried out using the above mixed solution of fragments a(478) and b(478X) as a template. Thus, one long fragment (the nucleotide sequence ranging from positions 1554 to 2663 of SEQ ID NO: 7) was prepared, in which the codon at target mutation position was substituted with NNN. Hereinafter, the DNA fragment is referred to as "fragment c(478X)."

The composition of the reaction solution for PCR for amplification of fragment c(478X) was the same as that employed for amplification of fragment c(475X) in Example 8 except for template DNA. The following template DNA was used: a mixed solution (1 μl) of fragments a(478) and b(478X). The PCR conditions were the same as those employed for amplification of fragment c(475X) in Example 8 except for annealing temperature. Annealing was carried out at 60° C.

The thus obtained PCR product of fragment c(478X) was electrophoresed with 0.7% agarose, so that an approximately 1100-bp fragment c(478X) could be confirmed. This was mixed with fragment d in Example 8. The mixture was then subjected to purification using Wizard (trademark) SV Gel and PCR Clean-Up system (Promega), phenol extraction, and then ethanol precipitation. The resultant was dissolved in 10 μl of sterile water (a mixed solution of fragments c(478X) and d).

Next, clones suspected of having undergone emission spectral shift were selected in a manner similar to that in Example 8 using 10 μl of a mixed solution of fragments c(478X) and d. The emission spectra of the thus obtained clones were measured.

As shown in Table 2, the emission spectral peak of the thus selected I407A mutant CLuc (the $7^{th}$ mutant luciferase) was 460 nm.

Example 12

T167K/K375R Double Mutant CLuc

DNA encoding double mutant CLuc (the $1^{st}$ and the 3 mutant luciferases) was prepared as described below, in which amino acid (threonine) at position 167 of the amino acid sequence shown in SEQ ID NO: 2 was substituted with lysine and amino acid (lysine) at position 375 of the same was substituted with arginine.

The DNA fragment containing an amino acid mutation at position 167 and consisting of the nucleotide sequence ranging from positions 1 to 1663 of SEQ ID NO: 7 is hereinafter referred to as "fragment a(238)."

The following oligo DNA primers were used for PCR for amplification of fragment a(238): FAR-F (SEQ ID NO: 16) and SQ-CLuc-CR1 (SEQ ID NO: 15). Furthermore, the composition of the reaction solution for PCR for amplification of fragment a(238) was the same as that employed for amplification of fragment a(475) in Example 8 except for the amount of sterile water, template DNA, and primers. The amount of sterile water and template DNA used herein are as follows: sterile water: 12.6 μl and pCLuRA-TDH3[T167K]: 1 μl (4.5 ng/μl). The PCR conditions were the same as those employed for amplification of fragment a(475) in Example 8 except for annealing temperature and extension time. Annealing was carried out at 53° C. and extension was carried out for 2 minutes.

Meanwhile, the DNA fragment containing an amino acid mutation at position 375 and consisting of the nucleotide sequence ranging from positions 1554 to 2875 of SEQ ID NO: 7 is hereinafter referred to as "fragment b(446)."

The following oligo DNA primers were used for PCR for amplification of fragment b(446): mut-CLuc-CF1 (SEQ ID NO: 12) and 3'-UTR (SEQ ID NO: 19). Furthermore, the composition of the reaction solution for PCR for amplification of fragment b(446) was the same as that employed for amplification of fragment a(238) except for template DNA and primers. The following template DNA was used: pCLuRA-TDH3[αP21L,K375R] (1 µl) (2.0 ng/µl). The PCR reaction conditions employed herein were the same as those employed for amplification of fragment a(238).

The thus obtained PCR products of fragment a(238) and fragment b(446) were electrophoresed with 1% agarose, so that they were confirmed to be an approximately 1700-bp DNA fragment and an approximately 1300-bp DNA fragment, respectively. They were mixed and then a mixed solution of fragments a(238) and b(446) was prepared in a manner similar to that in Example 8.

Next, overlap PCR was carried out using the above mixed solution of fragments a(238) and b(446) as a template. Thus, one long fragment (the nucleotide sequence ranging from positions 900 to 2663 of SEQ ID NO: 7) was prepared, in which amino acid at target position was substituted. Hereinafter, the DNA fragment is referred to as "fragment c(238, 446)."

The following oligo DNA primers were used for PCR for amplification of fragment c(238,446): mut-CLuc-F (SEQ ID NO: 8) and mut-CLuc-R (SEQ ID NO: 13). Furthermore, the composition of the reaction solution for PCR for amplification of fragment c(238,446) was the same as that employed for amplification of fragment c(475X) in Example 8 except for template DNA and primers. The following template DNA was used: a mixed solution (1 µl) of fragments a(238) and b(446). The PCR conditions were the same as those employed for amplification of fragment c(475X) in Example 8 except for annealing temperature and extension time. Annealing was carried out at 60° C. and extension was carried out for 2 minutes.

Meanwhile, a linear DNA fragment lacking a portion ranging from positions 967 to 2575 of SEQ ID NO: 7 in the pCLuRA-TDH3 sequence was amplified by PCR. Hereinafter, the DNA fragment is referred to as fragment d(238,446).

The following oligo DNA primers were used for PCR for amplification of fragment d(238,446): vec-CLuc-R (SEQ ID NO: 10) and vec-CLuc-F (SEQ ID NO: 14). Furthermore, the composition of the reaction solution for PCR for amplification of fragment d(238,446) was the same as that employed for amplification of fragment d in Example 8 except for primers. The PCR conditions were the same as those employed for amplification of fragment d in Example 8.

The thus obtained PCR products of fragment c(238,446) and fragment d(238,446) were electrophoresed with 0.7% agarose, so that they were confirmed to be an approximately 1700-bp DNA fragment and an approximately 7000-bp DNA fragment, respectively. They were mixed and then a mixed solution of fragments c(238,446) and d (238,446) was prepared in a manner similar to that in Example 8.

Next, the *Saccharomyces cerevisiae* BY4743Δprb1 strain was transformed using 10 µl of the mixed solution of fragments c(238,446) and d(238,446) and Frozen-EZ Yeast Transformation II™ (ZYMO RESEARCH).

Furthermore, emission spectra of the thus obtained clones were measured in a manner similar to that in Example 8 using 10 µl of the mixed solution of fragments c(238,446) and d(238,446).

As shown in Table 2, the emission spectral peak of the thus prepared T167K/K375R double mutant CLuc (the $1^{st}$ and the $3^{rd}$ mutant luciferases) was 460 nm. A pCLuRA-TDH3 plasmid having, with respect to the amino acid sequence shown in SEQ ID NO: 2, amino acid at position 167 mutated from threonine to lysine and amino acid at position 375 mutated from lysine to arginine is defined as "pCLuRA-TDH3 [T167K,K375R]."

Example 13

T167K/Q403P Double Mutant CLuc

A gene encoding double (T167K and Q403P) mutant CLuc (the $3^{rd}$ mutant luciferase) with respect to the amino acid sequence shown in SEQ ID NO: 2 was prepared. Mutagenesis was carried out in a manner similar to that in Example 12.

The DNA fragment containing an amino acid mutation at position 403 and consisting of the nucleotide sequence ranging from positions 1554 to 2875 of SEQ ID NO: 7 is hereinafter referred to as "fragment b(474)."

Furthermore, the composition of the reaction solution for PCR for amplification of fragment b(474) was the same as that employed for amplification of fragment b(446) in Example 12 except for template DNA. The following template DNA was used: pCLuRA-TDH3[Q403P] (pCLuRA-TDH3 plasmid obtained as a result of screening as described in Example 2, in which amino acid at position 403 of the amino acid sequence shown in SEQ ID NO: 2 was mutated from glutamine to proline) (1 µl) (2.56 ng/µl). The PCR conditions were the same as those employed for amplification of fragment b(446) in Example 12.

Next, a mixed solution of fragments a(238) (Example 12) and b(474) was prepared in a manner similar to that in Example 12.

Overlap PCR was carried out using the above mixed solution of fragments a(238) and b(474) as a template. Thus, one long fragment (the nucleotide sequence ranging from positions 900 to 2663 of SEQ ID NO: 7) was prepared, in which amino acid at target position was substituted. Hereinafter, the DNA fragment is referred to as "fragment c(238,474)."

The composition of the reaction solution for PCR for amplification of fragment c(238,474) was the same as that employed for amplification of fragment c(238,446) in Example 12 except for template DNA. The following template DNA was used: the mixed solution (1 µl) of fragments a(238) and b(474). The PCR conditions were the same as those in Example 12.

The thus obtained PCR products of fragment c(238,474) and fragment d(238,446) in Example 12 were electrophoresed with 0.7% agarose, so that a mixed solution of fragments c(238,474) and d(238,446) was prepared in a manner similar to that in Example 12.

Next, the emission spectra of the thus obtained clones were measured using 10 µl of the mixed solution of fragments c(238,474) and d(238,446) in a manner similar to that in Example 12.

As shown in Table 2, the emission spectral peak of the thus prepared T167K/Q403P double mutant CLuc (the $3^{rd}$ mutant luciferase) was 458 nm.

Example 14

T167K/N404G Double Mutant CLuc

A gene encoding double (T167K and N404G) mutant CLuc (the 3$^{rd}$ and the 4$^{th}$ mutant luciferases) with respect to the amino acid sequence shown in SEQ ID NO: 2 was prepared. Mutagenesis was carried out in a manner similar to that in Example 12.

A DNA fragment containing an amino acid mutation at position 404 and consisting of the nucleotide sequence ranging from positions 1554 to 2875 of SEQ ID NO: 7 is hereinafter referred to as "fragment b(475)."

The composition of the reaction solution for PCR for amplification of fragment b(475) was the same as that employed for amplification of fragment b(446) in Example 12 except for template DNA. The following template DNA was used: pCLuRA-TDH3[N404G] (Example 8) (1 µl) (2.70 ng/µl). The PCR conditions were the same as those employed for amplification of fragment b(446) in Example 12.

Next, a mixed solution of fragments a(238) (Example 12) and b(475) was prepared in a manner similar to that in Example 12.

Overlap PCR was carried out using the above mixed solution of fragments a(238) and b(475) as a template. Thus, one long fragment (the nucleotide sequence ranging from positions 900 to 2663 of SEQ ID NO: 7) was prepared, in which amino acid at target position was substituted. Hereinafter, the DNA fragment is referred to as "fragment c(238,475)."

The composition of the reaction solution for PCR for amplification of fragment c(238,475) was the same as that employed for amplification of fragment c(238,446) in Example 12 except for template DNA. The following template DNA was used: the mixed solution (1 µl) of fragments a(238) and b(475). The PCR conditions were the same as those in Example 12.

The thus obtained PCR products of fragment c(238,475) and fragment d(238,446) in Example 12 were electrophoresed with 0.7% agarose, so that a mixed solution of fragments c(238,475) and d(238,446) was prepared in a manner similar to that in Example 12.

Next, the emission spectra of the thus obtained clones were measured using 10 µl of the mixed solution of fragments c(238,475) and d(238,446) in a manner similar to that in Example 12.

As shown in Table 2, the emission spectral peak of the thus prepared T167K/N404G double mutant CLuc (the 3$^{rd}$ and the 4$^{th}$ mutant luciferases) was 460 nm.

Example 15

T167K/T405I Double Mutant CLuc

A gene encoding a double (T167K and T405I) mutant CLuc (the 3$^{rd}$ and the 5$^{th}$ mutant luciferases) with respect to the amino acid sequence shown in SEQ ID NO: 2 was prepared. Mutagenesis was carried out in a manner similar to that in Example 12.

A DNA fragment containing an amino acid mutation at position 405 and consisting of the nucleotide sequence ranging from positions 1554 to 2875 of SEQ ID NO: 7 is hereinafter referred to as "fragment b(476)."

The composition of the reaction solution for PCR for amplification of fragment b(476) was the same as that employed for amplification of fragment b(446) in Example 12 except for template DNA. The following template DNA was used: pCLuRA-TDH3[αP21L,T405I] (Example 5) (1 µl) (2.0 ng/µl). The PCR conditions were the same as those employed for amplification of fragment b(446) in Example 12.

Next, a mixed solution of fragments a(238) (Example 12) and b(476) was prepared in a manner similar to that in Example 12.

Overlap PCR was carried out using the above mixed solution of fragments a(238) and b(476) as a template. Thus, one long fragment (the nucleotide sequence ranging from positions 900 to 2663 of SEQ ID NO: 7) was prepared, in which amino acid at target position was substituted. Hereinafter, the DNA fragment is referred to as "fragment c(238,476)."

The composition of the reaction solution for PCR for amplification of fragment c(238,476) was the same as that employed for amplification of fragment c(238,446) in Example 12 except for template DNA. The following template DNA was used: the mixed solution (1 µl) of fragments a(238) and b(476). The PCR conditions were the same as those in Example 12.

The thus obtained PCR products of fragment c(238,476) and fragment d(238,446) in Example 12 were electrophoresed with 0.7% agarose, so that the mixed solution of fragments c(238,476) and d(238,446) was prepared in a manner similar to that in Example 12.

Next, the emission spectra of the thus obtained clones were measured using 10 µl of the mixed solution of fragments c(238,476) and d(238,446) in a manner similar to that in Example 12.

As shown in Table 2, the emission spectral peak of the thus prepared T167K/T405I double mutant CLuc (the 3$^{rd}$ and the 5$^{th}$ mutant luciferases) was 460 nm.

Example 16

Construction of L197 Saturation Mutant Library and Screening for Mutant CLuc 16-1. Construction of L197 Saturation Mutant Library A mutant library was constructed, in which amino acid at position 197 of the amino acid sequence shown in SEQ ID NO: 2 was substituted with any one of the other amino acids. The construction method is similar to that in Example 8.

The nucleotide sequence ranging from positions 1 to 1501 of SEQ ID NO: 7 was amplified by PCR. The DNA fragment is referred to as "fragment a(268)."

The following oligo DNA primers were used for PCR for amplification of fragment a(268): FAR-F (SEQ ID NO: 16) and L268-rev: gatgtcgatcacgatcagttt (SEQ ID NO: 37). Furthermore, the composition of the reaction solution for PCR for amplification of fragment a(268) was the same as that employed for amplification of fragment a(475) in Example 8 except for primers. The PCR conditions were the same as those employed for amplification of fragment a(475) in Example 8.

Meanwhile, the nucleotide sequence ranging from positions 1481 to 2875 of SEQ ID NO: 7 was amplified by PCR. The DNA fragment is referred to as "fragment b(268X)."

The following oligo DNA primers were used for PCR for amplification of fragment b(268X): L268X-Fw: aaactgatcgt-gatcgacatcnnnggaggaagatctgtaagaatc (SEQ ID NO: 38) and 3'-UTR (SEQ ID NO: 19). Furthermore, the composition of the reaction solution for PCR for amplification of fragment b(268X) was the same as that employed for amplification of fragment b(475X) in Example 8 except for primers. The PCR conditions were the same as those employed for amplification of fragment b(475X) in Example 8.

The thus obtained PCR products of fragment a(268) and fragment b(268X) were electrophoresed with 1% agarose, so that an approximately 1500-bp fragment a(268) and an approximately 1400-bp fragment b(268X) could be confirmed. Next, a mixed solution of fragments a(268) and b(268X) was prepared in a manner similar to that in Example 8.

Overlap PCR was carried out using the above mixed solution of fragments a(268) and b(268X) as a template. Thus, one long fragment (the nucleotide sequence ranging from positions 900 to 1813 of SEQ ID NO: 7) was prepared, in which the codon at target mutation position was substituted with NNN. Hereinafter, the DNA fragment is referred to as "fragment c(268X)."

The following oligo DNA primers were used for PCR for amplification of fragment c(268X): mut-CLuc-F (SEQ ID NO: 8) and mut-CLuc-NR2 (SEQ ID NO: 9). Furthermore, the composition of the reaction solution for PCR for amplification of fragment c(268X) was the same as that employed for amplification of fragment c(475X) in Example 8 except for template DNA and primers. The following template DNA was used: the mixed solution (1 µl) of fragments a(268) and b(268X). The PCR conditions were the same as those employed for amplification of fragment c(475X) in Example 8 except for annealing temperature. Annealing was carried out at 53° C.

Meanwhile, linear DNA lacking a portion ranging from positions 967 to 1703 of SEQ ID NO: 7 in the pCLuRA-TDH3 sequence was amplified by PCR. The DNA fragment is referred to as "fragment d(268)."

The following oligo DNA primers were used for PCR for amplification of fragment d(268): vec-CLuc-R (SEQ ID NO: 10) and SQ-CLuc-NF2 (SEQ ID NO: 11). Furthermore, the composition of the reaction solution for PCR for amplification of fragment d(268) was the same as that employed for amplification of fragment d in Example 8 except for primers. The PCR conditions were the same as those employed for amplification of fragment d in Example 8 except for annealing temperature. Annealing was carried out at 62° C.

The thus obtained PCR products of fragment c(268X) and fragment d(268) were electrophoresed with 0.7% agarose, so that an approximately 900-bp fragment c(268X) and an approximately 7000-bp fragment d(268) could be confirmed.

Next, a mixed solution of fragments c(268X) and d(268) was prepared in a manner similar to that in Example 8.

Furthermore, in a manner similar to that in Example 8 using the mixed solution of fragments c(268X) and d(268), a clone with an altered spectral peak position was obtained, in which amino acid at position 197 of the amino acid sequence shown in SEQ ID NO: 2 was mutated from leucine to proline. A pCLuRA-TDH3 plasmid, in which amino acid at position 197 of the amino acid sequence shown in SEQ ID NO: 2 was mutated from leucine to proline, is defined as "pCLuRA-TDH3[L197P]."

16-2. Preparation of M178K/L197P Double Mutant CLuc Gene

A gene encoding double (M178K and L197P) mutant CLuc (the $2^{nd}$ mutant luciferase) with respect to the amino acid sequence shown in SEQ ID NO: 2 was prepared. Mutagenesis was carried out in a manner similar to that in Example 12.

A DNA fragment containing amino acid mutation at position 178 shown in SEQ ID NO: 2 and consisting of the nucleotide sequence ranging from positions 1 to 1492 of SEQ ID NO: 7 was amplified by PCR. Hereinafter, the DNA fragment is referred to as "fragment a(249)."

The following oligo DNA primers were used for PCR for amplification of fragment a(249): FAR-F (SEQ ID NO: 16) and SQ-CLuc-F001-rev:cacgatcagtttgaagaattctatgacggt (SEQ ID NO: 39). Furthermore, the composition of the reaction solution for PCR for amplification of fragment a(249) was the same as that for amplification of fragment a(475) in Example 8, except for template DNA and primers. The following template DNA was used: pCLuRA-TDH3[M178K] (Example 2) (1 µl) (2.85 ng/µl). The PCR conditions were the same as those employed for amplification of fragment a(475) in Example 8, except for annealing temperature. Annealing was carried out at 58° C.

Meanwhile, a DNA fragment containing an amino acid mutation at position 197 of SEQ ID NO: 2 and consisting of the nucleotide sequence ranging from positions 1463 to 2875 of SEQ ID NO: 7 was amplified by PCR. Hereinafter, the DNA fragment is referred to as "fragment b(268)."

The following oligo DNA primers were used for PCR for amplification of fragment b(268): mut-CLuc-CF0: accgtcata-gaattcttcaaactgatcgtg (SEQ ID NO: 40) and 3'-UTR (SEQ ID NO: 19). Furthermore, the composition of the reaction solution for PCR for amplification of fragment b(268) was the same as that for amplification of fragment a(249), except for template DNA and primers. The following template DNA was used: pCLuRA-TDH3[L197P] (the section 16-1 above) (1 µl) (3.53 ng/µl). The PCR conditions were the same as those employed for amplification of fragment a(249).

The thus obtained PCR products of fragment a(249) and fragment b(268) were electrophoresed with 1% agarose, so that they were confirmed to be an approximately 1500-bp DNA fragment and an approximately 1400-bp DNA fragment, respectively. They were mixed and then a mixed solution of fragments a(249) and b(268) was prepared in a manner similar to that in Example 8.

Next, overlap PCR was carried out using the above mixed solution of fragments a(249) and b(268) as a template. Thus, one long fragment (the nucleotide sequence ranging from positions 900 to 1813 of SEQ ID NO: 7) was prepared, in which amino acid at target position was substituted. Hereinafter, the DNA fragment is referred to as "fragment c(249, 268)."

Furthermore, the composition of the reaction solution for PCR for amplification of fragment c(249,268) was the same as that employed for amplification of fragment c(268X) in the section 16-1 above except for template DNA. The following template DNA was used: the mixed solution (1 µl) of fragments a(249) and b(268). The PCR conditions were the same as those employed for amplification of fragment c(268X) in the section 16-1 above, except for annealing temperature and extension time alone. Annealing was carried out at 60° C. and extension was carried out for 1 minute and 30 seconds.

The thus obtained PCR products of fragment c(249,268) and fragment d(268) in the section 16-1 above were electrophoresed with 0.7% agarose, so that they were confirmed to be an approximately 800-bp DNA fragment and an approximately 7000-bp DNA fragment, respectively. They were mixed and then a mixed solution of fragments c(249,268) and d(268) was prepared in a manner similar to that in Example 8.

Next, in a manner similar to that in Example 8, a clone was obtained, in which, amino acid at position 178 of the amino acid sequence shown in SEQ ID NO: 2 was mutated from methionine to lysine and amino acid at position 197 of the same was mutated from leucine to proline. A pCLuRA-TDH3 plasmid, in which, amino acid at position 178 of the amino acid sequence shown in SEQ ID NO: 2 was mutated from methionine to lysine and amino acid at position 197 of the same was mutated from leucine to proline is defined as "pCLuRA-TDH3[M178K,L197P]."

16-3. Mutagenesis of Amino Acid at Position 21 within the Signal Sequence of αCLuc Amino acid at position 21 within the signal sequence of αCLuc shown in SEQ ID NO: 6 was substituted with leucine. Mutagenesis is carried out as follows. A DNA fragment containing a mutation corresponding to position 21 in the amino acid sequence shown in SEQ ID NO: 6 and a DNA fragment containing two mutations at positions 178 and 197 of the amino acid sequence shown in SEQ ID NO: 2 were amplified by PCR. Preparation was carried out by overlap PCR using the two DNA fragments.

A DNA fragment consisting of the nucleotide sequence ranging from positions 1 to 966 of SEQ ID NO: 7 and containing an amino acid mutation at position 21 shown in SEQ ID NO: 6 was amplified by PCR. Hereinafter, the DNA fragment is referred to as "fragment a(21)."

The composition of the reaction solution for PCR for amplification of fragment a(21) was the same as that employed for amplification of fragment a(238) in Example 12 except for template DNA and primers. The following template DNA and oligo DNA primers were used: pCLuRA-TDH3[αP21L] (1 µl) (4.25 ng/µl), and FAR-F (SEQ ID NO: 16) and vec-CLuc-R (SEQ ID NO: 10). The PCR conditions were the same as those employed for amplification of fragment a(238) in Example 12, except for annealing temperature. Annealing was carried out at 53° C.

Meanwhile, a DNA fragment consisting of the nucleotide sequence ranging from positions 900 to 2875 of SEQ ID NO: 7 and containing amino acid mutations at positions 178 and 197 of SEQ ID NO: 2 was amplified by PCR. Hereinafter, the DNA fragment is referred to as "fragment b(249,268)."

The composition of the reaction solution for PCR for amplification of fragment b(249,268) was the same as that employed for amplification of fragment a(21) except for template DNA and primers. The following template DNA and oligo DNA primers were used: pCLuRA-TDH3[M178K,L197P] (the section 16-2 above) (1 µl) (1.56 ng/µl), and mut-CLuc-F (SEQ ID NO: 8) and 3'-UTR (SEQ ID NO: 19). The PCR conditions were the same as those employed for amplification of fragment a(21).

The thus obtained PCR products of fragment a(21) and fragment b(249,268) were electrophoresed with 1% agarose, so that they were confirmed to be an approximately 1000-bp DNA fragment and an approximately 1900-bp DNA fragment. They were mixed and then a mixed solution of fragments a(21) and b(249,268) was prepared in a manner similar to that in Example 8.

Next, overlap PCR was carried out using the above mixed solution of fragments a(21) and b(249,268) as a template. Thus, one long fragment (the nucleotide sequence ranging from positions 461 to 1813 of SEQ ID NO: 7) was prepared, in which amino acid at target position was substituted. Hereinafter, the DNA fragment is referred to as "fragment c(21,249,268)."

The following oligo DNA primers were used for PCR for amplification of fragment c(21,249,268): SQ-GPD1-F0: ATGTATCTATCTCATTTTCTTACA (SEQ ID NO: 41) and mut-CLuc-NR2 (SEQ ID NO: 9). Furthermore, the composition of the reaction solution for PCR for amplification of fragment c(21,249,268) was the same as that employed for amplification of fragment c(238,446) in Example 12, except for template DNA and primers. The following template DNA was used: the mixed solution (1 µl) of fragments a(21) and b(249,268). The PCR conditions were the same as those employed for amplification of fragment a(238) in Example 12, except for annealing temperature. Annealing was carried out at 51° C.

Meanwhile, a linear DNA fragment lacking a portion ranging from positions 526 to 1703 of SEQ ID NO: 7 in the sequence of pCLuRA-TDH3 was amplified by PCR. Hereinafter, the DNA fragment is referred to as "fragment d(21,249,268)."

The following oligo DNA primers were used for PCR for amplification of fragment d(21,249,268): SQ-GPD 1-R0: CAGCTTTTTCCAAATCAGAGAGAGCAG (SEQ ID NO: 42) and SQ-CLuc-NF2 (SEQ ID NO: 11). Furthermore, the composition of the reaction solution for PCR for amplification of fragment d(21,249,268) was the same as that employed for amplification of fragment d(238,446) in Example 12 except for primers. The PCR conditions were the same as those employed for amplification of fragment d(238, 446) in Example 12.

The thus obtained PCR products of fragments c(21,249, 268) and d(21,249,268) were electrophoresed with 0.7% agarose, so that they were confirmed to be an approximately 1300-bp DNA fragment and an approximately 7000-bp DNA fragment. They were mixed and then a mixed solution of fragments c(21,249,268) and d(21,249,268) was prepared in a manner similar to that in Example 8.

Next, the emission spectra of the thus obtained clones were measured in a manner similar to that in Example 8 using mixed solution of fragments c(21,249,268) and d(21,249, 268).

As shown in Table 2, the emission spectral peak of the thus prepared M178K/L197P double mutant CLuc (the $2^{nd}$ mutant luciferase) was 447 nm.

Example 17

K375R/Q403P Double Mutant CLuc

A gene encoding double (K375R and Q403P) mutant CLuc (the $1^{st}$ mutant luciferase) with respect to the amino acid sequence shown in SEQ ID NO: 2 was prepared. Mutagenesis was carried out in a manner similar to that in Example 12.

A DNA fragment consisting of the nucleotide sequence ranging from positions 900 to 2087 of SEQ ID NO: 7 and containing an amino acid mutation at position 375 is hereinafter referred to as "fragment a(446)."

The following oligo DNA primers were used for PCR for amplification of fragment a(446): mut-CLuc-F (SEQ ID NO: 8) and SQ-CLuc-F002-rev: caaccagaatctgttttccatcaa (SEQ ID NO: 43). Furthermore, the composition of the reaction solution for PCR for amplification of fragment a(446) was the same as that employed for amplification of fragment a(238) in Example 12, except for template DNA and primers. The following template DNA was used: pCLuRA-TDH3[αP21L, K375R] (Example 4) (1 µl) (2.0 ng/µl). The PCR conditions were the same as those employed for amplification of fragment a(238) in Example 12.

Meanwhile, a DNA fragment consisting of nucleotide sequence ranging from positions 2064 to 2875 of SEQ ID NO: 7 and containing an amino acid mutation at position 403 is hereinafter referred to as "fragment b'(474)."

The following oligo DNA primers were used for PCR for amplification of fragment b'(474): SQ-CLuc-F002: ttgatggaaaacagattctggttg (SEQ ID NO: 44) and 3'-UTR (SEQ ID NO: 19). Furthermore, the composition of the reaction solution for PCR for amplification of fragment b'(474) was the same as that employed for amplification of fragment b(474) in Example 13 except for primers. The PCR conditions were the same as those employed for amplification of fragment b(446) in Example 12.

The thus obtained PCR products of fragments a(446) and b'(474) were electrophoresed with 1% agarose, so that they were confirmed to be an approximately 1100-bp DNA fragment and an approximately 800-bp DNA fragment, respectively. They were mixed and then a mixed solution of fragments a(446) and b'(474) was prepared in a manner similar to that in Example 8.

Next, overlap PCR was carried out using the above mixed solution of fragments a(446) and b'(474) as a template. Thus, one long fragment (the nucleotide sequence ranging from positions 1554 to 2663 of SEQ ID NO: 7) was prepared, in which amino acid at target position was substituted. Hereinafter, the DNA fragment is referred to as "fragment c(446, 474)."

The composition of the reaction solution for PCR for amplification of fragment c(446,474) was the same as that employed for amplification of fragment c(475X) in Example 8 except for template DNA. The following template DNA was used: the mixed solution (1 µl) of fragments a (446) and b'(474). The PCR conditions were the same as those employed for amplification of fragment c(238,446) in Example 12.

The thus obtained PCR product of fragment c(446,474) was electrophoresed with 0.7% agarose. A mixed solution of fragments c(446,474) and d (Example 8) was prepared in a manner similar to that in Example 8.

Next, the emission spectra of the thus obtained clones were measured in a manner similar to that in Example 12 using 10 µl of the mixed solution of fragments c(446,474) and d.

As shown in Table 2, the emission spectral peak of the thus prepared K375R/Q403P double mutant CLuc (the $1^{st}$ mutant luciferase) was 460 nm.

Example 18

K375R/N404G Double Mutant CLuc

A gene encoding double (K375R and N404G) mutant CLuc (the $1^{st}$ and the $4^{th}$ mutant luciferases) with respect to the amino acid sequence shown in SEQ ID NO: 2 was prepared. Mutagenesis was carried out in a manner similar to that in Example 12.

A DNA fragment consisting of the nucleotide sequence ranging from positions 2064 to 2875 of SEQ ID NO: 7 and containing an amino acid mutation at position 404 is hereinafter referred to as "fragment b'(475)."

The composition of the reaction solution for PCR for amplification of fragment b'(475) was the same as that employed for amplification of fragment b'(474) in Example 17 except for template DNA. The following template DNA was used: pCLuRA-TDH3[N404G] (Example 8) (1 µl) (2.70 ng/µl). The PCR conditions were the same as those in Example 12.

The thus obtained PCR products of fragments a(446) and b'(475) in Example 17 were electrophoresed with 1% agarose. A mixed solution of fragments a(446) and b'(475) was prepared in a manner similar to that in Example 12.

Next, overlap PCR was carried out using the above mixed solution of fragments a(446) and b'(475) as a template. Thus, one long fragment (the nucleotide sequence ranging from positions 1554 to 2663 of SEQ ID NO: 7) was prepared, in which amino acid at target position was substituted. Hereinafter, the DNA fragment is referred to as "fragment c(446, 475)."

The composition of the reaction solution for PCR for amplification of fragment c(446,475) was the same as that employed for amplification of fragment c(475X) in Example 8 except for template DNA. The following template DNA was used: the mixed solution (1 µl) of fragments a(446) and b'(475). The PCR conditions were the same as those employed for amplification of fragment c(475X) in Example 8.

The thus obtained PCR product of fragment c(446,475) was electrophoresed with 0.7% agarose. A mixed solution of fragments c(446,475) and d (Example 8) was prepared in a manner similar to that in Example 8.

Next, the emission spectra of the thus obtained clones were measured in a manner similar to that in Example 12 using 10 µl of the mixed solution of fragments c(446,475) and d.

As shown in Table 2, the emission spectral peak of the thus prepared K375R/N404G double mutant CLuc (the $1^{st}$ and the 4 h mutant luciferases) was 461 nm.

Example 19

K375R/T405I Double Mutant CLuc

A gene encoding double (K375R and T405I) mutant CLuc (the $1^{st}$ and the $5^{th}$ mutant luciferases) with respect to the amino acid sequence shown in SEQ ID NO: 2 was prepared. Mutagenesis was carried out in a manner similar to that in Example 12.

A DNA fragment consisting of the nucleotide sequence ranging from positions 2064 to 2875 of SEQ ID NO: 7 and containing an amino acid mutation at position 405 is hereinafter referred to as "fragment b'(476)."

The composition of the reaction solution for PCR for amplification of fragment b'(476) was the same as that employed for amplification of fragment b'(474) in Example 17, except for template DNA. The following template DNA was used: pCLuRA-TDH3[αP21L,T405I] (Example 5) (1 µl) (2.0 ng/11). The PCR conditions were the same as those employed for amplification of fragment b(446) in Example 12.

The thus obtained PCR products of fragment a(446) of Example 17 and fragment b'(476) were electrophoresed with 1% agarose. A mixed solution of fragments a(446) and b'(476) was prepared in a manner similar to that in Example 17.

Next, overlap PCR was carried out using the above mixed solution of fragments a(446) and b'(476) as a template. Thus, one long fragment (the nucleotide sequence ranging from positions 1554 to 2663 of SEQ ID NO: 7) was prepared, in which amino acid at target position was substituted. Hereinafter, the DNA fragment is referred to as "fragment c(446, 476)."

The composition of the reaction solution for PCR for amplification of fragment c(446,476) was the same as that employed for PCR in Example 8 except for template DNA. The following template DNA was used: the mixed solution (1 µl) of fragments a(446) and b'(476). The PCR conditions were the same as those employed for amplification of fragment c(238,446) in Example 12.

The thus obtained PCR product of fragment c(446,476) was electrophoresed with 0.7% agarose. A mixed solution of fragments c(446,476) and d (Example 8) was prepared in a manner similar to that in Example 8.

Next, the emission spectra of the thus obtained clones were measured in a manner similar to that in Example 8 using 10 µl of the mixed solution of fragments c(446,476) and d.

As shown in Table 2, the emission spectral peak of the thus prepared K375R/T405I double mutant CLuc (the 1$^{st}$ and the 5$^{th}$ mutant luciferases) was 463 nm.

Example 20

Q403P/N404G Double Mutant CLuc

A gene encoding double (Q403P and N404G) mutant CLuc (the 4$^{th}$ mutant luciferase) with respect to the amino acid sequence shown in SEQ ID NO: 2 was prepared. Mutagenesis was carried out in a manner similar to that in Example 12.

A DNA fragment consisting of the nucleotide sequence ranging from positions 1 to 2119 of SEQ ID NO: 7 is hereinafter referred to as "fragment a(474)."

The following oligo DNA primers were used for PCR for amplification of fragment a(474): FAR-F (SEQ ID NO: 16) and Q474-rev:agagctgtacgggacggacac (SEQ ID NO: 45). Furthermore, the composition of the reaction solution for PCR for amplification of fragment a(474) was the same as that employed for amplification of fragment a(475) in Example 8 except for primers. The PCR conditions were the same as those employed for amplification of fragment a(475) in Example 8, except for annealing temperature. Annealing was carried out at 55° C.

Meanwhile, a DNA fragment consisting of the nucleotide sequence ranging from positions 2099 to 2875 of SEQ ID NO: 7 and containing amino acid mutations at positions 403 and 404 is hereinafter referred to as "fragment b(474,475)."

The following oligo DNA primers were used for PCR for amplification of fragment b(474,475): Q474P/N475G-Fw: gtgtccgtcccgtacagctctcccgggacttccatctactggcaagat (SEQ ID NO: 46) and 3'-UTR (SEQ ID NO: 19). Furthermore, the composition of the reaction solution for PCR for amplification of fragment b(474,475) was the same as that employed for amplification of fragment b(475X) in Example 8 except for primers. The PCR conditions were the same as those employed for amplification of fragment b(475X) in Example 8, except for annealing temperature. Annealing was carried out at 58° C.

Next, a mixed solution of fragments a(474) and b(474,475) was prepared in a manner similar to that in Example 8.

Overlap PCR was carried out using the above mixed solution of fragments a(474) and b(474,475) as a template. Thus, one long fragment (the nucleotide sequence ranging from positions 1554 to 2663 of SEQ ID NO: 7) was prepared, in which amino acid at target position was substituted. Hereinafter, the DNA fragment is referred to as "fragment c(474,475)."

The composition of the reaction solution for PCR for amplification of fragment c(474,475) was the same as that employed for amplification of fragment c(475X) in Example 8 except for template DNA. The following template DNA was used: the mixed solution (1 μl) of fragments a(474) and b(474, 475). The PCR conditions were the same as those employed for amplification of fragment c(475X) in Example 8, except for annealing temperature and extension time. Annealing was carried out at 60° C. and extension was carried out for 1 minute and 30 seconds.

The thus obtained PCR product of fragment c(474,475) was electrophoresed with 0.7% agarose. A mixed solution of fragments c(474,475) and d (Example 8) was prepared in a manner similar to that in Example 8.

Next, the emission spectra of the thus obtained clones were measured in a manner similar to that in Example 8 using 10 μl of the mixed solution of fragments c(474,475) and d.

As shown in Table 2, the emission spectral peak of the thus prepared Q403P/N404G double mutant CLuc (the 4$^{th}$ mutant luciferase) was 462 nm.

Example 21

Q403P/T405I Double Mutant CLuc

A gene encoding double (Q403P and T405I) mutant CLuc (the 5$^{th}$ mutant luciferase) with respect to the amino acid sequence shown in SEQ ID NO: 2 was prepared. Mutagenesis was carried out in a manner similar to that in Example 12.

A DNA fragment consisting of the nucleotide sequence ranging from positions 2099 to 2875 of SEQ ID NO: 7 and containing amino acid mutation at position 403 and the same at position 405 is hereinafter referred to as "fragment b(474, 476)."

The following oligo DNA primers were used for PCR for amplification of fragment b(474,476): Q474P/T476I-Fw: gtgtccgtcccgtacagctctcccaacatctccatctactggcaagatggt (SEQ ID NO: 47) and 3'-UTR (SEQ ID NO: 19). The composition of the reaction solution in PCR for amplification of fragment b(474,476) was the same as that employed for amplification of fragment b(475X) in Example 8, except for primers. The PCR conditions were the same as those employed for amplification of fragment b(474,475) in Example 20.

Next, a mixed solution of fragments a(474) and b(474,476) was prepared in a manner similar that in Example 8.

Overlap PCR was carried out using the above mixed solution of fragments a(474) (Example 20) and b(474,476) as a template. Thus, one long fragment (the nucleotide sequence ranging from positions 1554 to 2663 of SEQ ID NO: 7) was prepared, in which amino acid at target position was substituted. Hereinafter, the DNA fragment is referred to as "fragment c(474,476)."

The composition of the reaction solution in PCR for amplification of fragment c(474,476) was the same as that employed for amplification of fragment c(475X) in Example 8, except for template DNA. The following template DNA was used: the mixed solution (1 μl) of fragments a(474) and b(474,476). The PCR conditions were the same as those employed for amplification of fragment c(474,475) in Example 20.

The thus obtained PCR product of fragment c(474,476) was electrophoresed with 0.7% agarose. A mixed solution of fragments c(474,476) and d (Example 8) was prepared in a manner similar to that in Example 8.

Next, the emission spectra of the thus obtained clones were measured using 10 μl of the mixed solution of fragments c(474,476) and d in a manner similar to that in Example 8.

As shown in Table 2, the emission spectral peak of the thus prepared Q403P/T405I double mutant CLuc (the 5$^{th}$ mutant luciferase) was 459 nm.

Example 22

N404G/T405I Double Mutant CLuc

A gene encoding double (N404G and T405I) mutant CLuc (the 4$^{th}$ and the 5$^{th}$ mutant luciferases) with respect to the amino acid sequence shown in SEQ ID NO: 2 was prepared. Mutagenesis was carried out in a manner similar to that in Example 12.

A DNA fragment consisting of the nucleotide sequence ranging from positions 2102 to 2875 of SEQ ID NO: 7 and containing amino acid mutations at positions 404 and 405 is hereinafter referred to as "fragment b(475,476)."

The following oligo DNA primers were used for PCR for amplification of fragment b(475,476): N475G/T476I-Fw: tccgtcccgtacagctctcaggggatctccatctactggcaagatggt (SEQ ID NO: 48) and 3'-UTR (SEQ ID NO: 19). Furthermore, the composition of the reaction solution for PCR for amplification of fragment b(475,476) was the same as that employed for amplification of fragment b(475X) in Example 8 except for primers. The PCR conditions were the same as those employed for amplification of fragment b(474,475) in Example 20.

Next, a mixed solution of fragments a(475) (Example 8) and b(475,476) was prepared in a manner similar to that in Example 8.

Overlap PCR was carried out using the above mixed solution of fragments a(475) and b(475,476) as a template. Thus, one long fragment (the nucleotide sequence ranging from positions 1554 to 2663 of SEQ ID NO: 7) was prepared, in which amino acid at target position was substituted. Hereinafter, the DNA fragment is referred to as "fragment c(475, 476)."

The composition of the reaction solution in PCR for amplification of fragment c(475,476) was the same as that employed for amplification of fragment c(475X) in Example 8, except for template DNA. The following template DNA was used: the mixed solution (1 μl) of fragments a(475) and b(475,476). The PCR conditions were the same as those employed for amplification of fragment c(474,475) in Example 20.

The thus obtained PCR product of fragment c(475,476) was electrophoresed with 0.7% agarose. The experiment was conducted in a manner similar to that in Example 8, so that a mixed solution of fragments c(475,476) and d (Example 8) was prepared.

Next, the emission spectra of the thus obtained clones were measured in a manner similar to that in Example 8 using 10 μl of the mixed solution of fragments c(475,476) and d.

As shown in Table 2, the emission spectral peak of the thus prepared N404G/T405I double mutant CLuc (the $4^{th}$ and the $5^{th}$ mutant luciferases) was 461 nm.

Example 23

Q403P/N404G/T405I Triple Mutant CLuc and Q403P/N404G/T405M Triple Mutant CLuc 23-1. Preparation (1) of Triple Mutant CLuc Gene with Mutations at Positions 403, 404, and 405

A gene encoding triple (Q403P, N404G, and T405I) mutant CLuc (the $4^{th}$ and the $5^{th}$ mutant luciferases) with respect to the amino acid sequence shown in SEQ ID NO: 2 was prepared. Mutagenesis was carried out in a manner similar to that in Example 12.

A DNA fragment consisting of the nucleotide sequence ranging from positions 2099 to 2875 of SEQ ID NO: 7 and containing amino acid mutations at positions 403, 404, and 405 is hereinafter referred to as "fragment b(474,475,476I)."

The following oligo DNA primers were used for PCR for amplification of fragment b(474,475,476I): Q474P/N475G/T476I-Fw: gtgtccgtcccgtacagctctcccgg-gatctccatctactggcaagatggt (SEQ ID NO: 49) and 3'-UTR (SEQ ID NO: 19). Furthermore, the composition of the reaction solution in PCR for amplification of fragment b(474,475, 476I) was the same as that employed for amplification of fragment b(475X) in Example 8, except for primers. The PCR conditions were the same as those employed for amplification of fragment b(474,475) in Example 20.

Next, a mixed solution of fragments a(474) (Example 20) and b(474,475,476I) was prepared in a manner similar to that in Example 8.

Overlap PCR was carried out using the above mixed solution of fragments a(474) and b(474,475,476I) as a template. Thus, one long fragment (the nucleotide sequence ranging from positions 1554 to 2663 of SEQ ID NO: 7) was prepared, in which amino acid at target position was substituted. Hereinafter, the DNA fragment is referred to as "fragment c(474, 475,476I)."

The composition of the reaction solution for PCR for amplification of fragment c(474,475,476I) was the same as that employed for amplification of fragment c(475X) in Example 8 except for template DNA. The following template DNA was used: the mixed solution (1 μl) of fragments a(474) and b(474,475,476I). The PCR conditions were the same as those employed for amplification of fragment c(474,475) in Example 20.

The thus obtained PCR product of fragment c(474,475, 476I) was electrophoresed with 0.7% agarose. A mixed solution of fragments c(474,475,476I) and d (Example 8) was prepared in a manner similar to that in Example 8.

The emission spectra of the thus obtained clones were measured in a manner similar to that in Example 8 using 10 μl of the mixed solution of fragments c(474,475,476I) and d.

As shown in Table 2, the emission spectral peak of the thus prepared Q403P/N404G/T405I triple mutant CLuc (the $4^{th}$ and the $5^{th}$ mutant luciferases) was 462 nm.

23-2. Preparation (2) of Triple Mutant CLuc Gene with Mutations at Positions 403, 404, and 405

A gene encoding triple (Q403P, N404G, and T405M) mutant CLuc (the $4^{th}$ and the $5^{th}$ mutant luciferases) with respect to the amino acid sequence shown in SEQ ID NO: 2 was prepared. Mutagenesis was carried out in a manner similar to that in Example 12.

A DNA fragment consisting of the nucleotide sequence ranging from positions 2099 to 2875 of SEQ ID NO: 7 and containing amino acid mutations at positions 403, 404, and 405 is hereinafter referred to as "fragment b(474,475, 476M)."

The following oligo DNA primers were used for PCR for amplification of fragment b(474,475,476M): Q474P/N475G/T476M-Fw: gtgtccgtcccgtacagctctcccgg-gatgtccatctactggcaagatggt (SEQ ID NO: 50) and 3'-UTR (SEQ ID NO: 19). Furthermore, the composition of the reaction solution in PCR for amplification of fragment b(474,475, 476M) was the same as that employed for amplification of fragment b(475X) in Example 8, except for primers. The PCR conditions were the same as those employed for amplification of fragment b(474,475) in Example 20.

Next, a mixed solution of fragments a(474) (Example 20) and b(474,475,476M) was prepared in a manner similar to that in Example 8.

Overlap PCR was carried out using the above mixed solution of fragments a(474) and b(474,475,476M) as a template. Thus, one long fragment (the nucleotide sequence ranging from positions 1554 to 2663 of SEQ ID NO: 7) was prepared, in which amino acid at target position was substituted. Hereinafter, the DNA fragment is referred to as "fragment c(474, 475,476M)."

The composition of the reaction solution for PCR for amplification of fragment c(474,475,476M) was the same as that employed for amplification of fragment c(475X) in Example 8 except for template DNA. The following template DNA was used: the mixed solution (1 μl) of fragments a(474) and b(474,475,476M). The PCR conditions employed herein were the same as those employed for amplification of fragment c(474,475) in Example 20.

The thus obtained PCR product of fragment c(474,475, 476M) was electrophoresed with 0.7% agarose. A mixed solution of fragments c(474,475,476M) and d (Example 8) was prepared in a manner similar to that in Example 8.

Next, the emission spectra of the thus obtained clones were measured in a manner similar to that in Example 8 using 10 µl of the mixed solution of fragments c(474,475,476M) and d.

As shown in Table 2, the emission spectral peak of the thus prepared Q403P/N404G/T405M triple mutant CLuc (the 4th and the 5th mutant luciferases) was 462 nm. A pCLuRA-TDH3 plasmid, in which amino acid at position 403 of the amino acid sequence shown in SEQ ID NO: 2 was mutated from glutamine to proline, amino acid at position 404 of the same was mutated from asparagine to glycine, and amino acid at position 405 of the same was mutated from threonine to methionine, is defined as "pCLuRA-TDH3[Q403P,N404G, T405M]."

Example 24

Q403P/N404G/T405M/S406L Quadruple Mutant CLuc

A gene encoding quadruple (Q403P, N404G, T405M, and S406L) mutant CLuc (the 4th to the 6th mutant luciferases) with respect to the amino acid sequence shown in SEQ ID NO: 2 was prepared. Mutagenesis was carried out in a manner similar to that in Example 12.

A DNA fragment consisting of the nucleotide sequence ranging from positions 2099 to 2875 of SEQ ID NO: 7 and containing amino acid mutations at positions 403, 404, 405, and 406 is hereinafter referred to as "fragment b(474,475, 476,477)."

The following oligo DNA primers were used for PCR for amplification of fragment b(474,475,476,477): Q474P/ N475G/T476M/S477L-Fw: gtgtccgtcccgtacagctctcccgg-gatgctcatctactggcaagatggtgac (SEQ ID NO: 51) and 3'-UTR (SEQ ID NO: 19). Furthermore, the composition of the reaction solution for PCR for amplification of fragment b(474, 475,476,477) was the same as that employed for amplification of fragment b(475X) in Example 8 except for primers. The PCR conditions were the same as those employed for amplification of fragment b(475X) in Example 8 except for annealing temperature. Annealing was carried out at 55° C.

Next, a mixed solution of fragments a(474) (Example 20) and b(474,475,476,477) was prepared in a manner similar to that in Example 8.

Overlap PCR was carried out using the above mixed solution of fragments a(474) and b(474,475,476,477) as a template. Thus, one long fragment (the nucleotide sequence ranging from positions 1554 to 2663 of SEQ ID NO: 7) was prepared, in which amino acid at target position was substituted. Hereinafter, the DNA fragment is referred to as "fragment c(474,475,476,477)."

The composition of the reaction solution for PCR for amplification of fragment c(474,475,476,477) was the same as that employed for amplification of fragment c(475X) in Example 8, except for template DNA. The following template DNA was used: the mixed solution (1 µl) of fragments a(474) and b(474,475,476,477). The PCR conditions were the same as those employed for amplification of fragment c(475X) in Example 8 except for annealing temperature. Annealing was carried out at 61° C.

The thus obtained PCR product of fragment c(474,475, 476,477) was electrophoresed with 0.7% agarose and then a mixed solution of fragments c(474,475,476,477) and d (Example 8) was prepared in a manner similar to that in Example 8.

Next, the emission spectra of the thus obtained clones were measured in a manner similar to that in Example 8 using 10 µl of the mixed solution of fragments c(474,475,476,477) and d.

As shown in Table 2, the emission spectral peak of the thus prepared Q403P/N404G/T405M/S406L quadruple mutant CLuc (the 4th to the 6th mutant luciferases) was 461 nm.

Example 25

Preparation of Q403P/N404G/T405M/S406L/I407A Quintuple Mutant CLuc Gene

A gene encoding quintuple (Q403P, N404G, T405M, S406L, and I407A) mutant CLuc (the 4th to the 7th mutant luciferases) with respect to the amino acid sequence shown in SEQ ID NO: 2 was prepared. Mutagenesis was carried out in a manner similar to that in Example 12.

A DNA fragment consisting of the nucleotide sequence ranging from positions 2099 to 2875 of SEQ ID NO: 7 and containing amino acid mutations at positions 403, 404, 405, 406, and 407 is hereinafter referred to as "fragment b(474, 475,476,477,478)."

The following oligo DNA primers were used for PCR for amplification of fragment b(474,475,476,477,478): Q474P/ N475G/T476M/S477L/I478A-Fw: gtgtccgtcccgtacagctctc-ccgggatgctcgcctactggcaagatggtgacata (SEQ ID NO: 52) and 3'-UTR (SEQ ID NO: 19). Furthermore, the composition of the reaction solution for PCR for amplification of fragment b(474,475,476,477,478) was the same as that employed for amplification of fragment b(475X) in Example 8 except for primers. The PCR conditions were the same as those employed for amplification of fragment b(268) in the section 16-2 of Example 16.

Next, a mixed solution of fragments a(474) and b(474,475, 476,477,478) was prepared in a manner similar to that in Example 8.

Overlap PCR was carried out using the above mixed solution of fragments a(474) and b(474,475,476,477,478) as a template. Thus, one long fragment (the nucleotide sequence ranging from positions 1554 to 2663 of SEQ ID NO: 7) was prepared, in which amino acid at target position was substituted. Hereinafter, the DNA fragment is referred to as "fragment c(474,475,476,477,478)."

The composition of the reaction solution for PCR for amplification of fragment c(474,475,476,477,478) was the same as that employed for amplification of fragment c(475X) in Example 8 except for template DNA. The following template DNA was used: the mixed solution (1 µl) of fragments a(474) and b(474,475,476,477,478). The PCR conditions were the same as those employed for amplification of fragment c(249,268) in the section 16-2 of Example 16.

The PCR product of fragment c(474,475,476,477,478) was electrophoresed with 0.7% agarose and then a mixed solution of fragments c(474,475,476,477,478) and d (Example 8) was prepared in a manner similar to that in Example 8.

Next, the emission spectra of the thus obtained clones were measured in a manner similar to that in Example 8 using 10 µl of the mixed solution of fragments c(474,475,476,477,478) and d.

As shown in Table 2, the emission spectral peak of the thus prepared Q403P/N404G/T405M/S406L/I407A quintuple mutant CLuc (the 4th to the 7th mutant luciferases) was 460 nm. A pCLuRA-TDH3 plasmid having, with respect to the amino acid sequence shown in SEQ ID NO: 2, amino acid at position 403 mutated from glutamine to proline, amino acid at position 404 mutated from asparagine to glycine, amino acid at position 405 mutated from threonine to methionine, amino acid at position 406 mutated from serine to leucine and amino acid at position 407 mutated from isoleucine to alanine, is defined as "pCLuRA-TDH3[Q403P,N404G,T405M,S406L, I407A]."

Example 26

Preparation of T167K/Q403P/N404G/T405M/S406L/I407A Sextuple Mutant CLuc Gene

A gene encoding sextuple (T167K, Q403P, N404G, T405M, S406L, and I407A) mutant CLuc (the $3^{rd}$ to the $7^{th}$ mutant luciferases) with respect to the amino acid sequence shown in SEQ ID NO: 2 was prepared. Mutagenesis was carried out in a manner similar to that in Example 12.

Meanwhile, a DNA fragment consisting of the nucleotide sequence ranging from positions 1 to 1813 of SEQ ID NO: 7 and containing an amino acid mutation at position 167 is hereinafter referred to as "fragment a'(238)."

The composition of the reaction solution for PCR for amplification of fragment a'(238) was the same as that employed for amplification of fragment a(238) in Example 12 except for primers. The following oligo DNA primers were used: FAR-F (SEQ ID NO: 16) and mut-CLuc-NR2 (SEQ ID NO: 9). The PCR conditions employed herein were the same as those employed for amplification of fragment a(475) in Example 8, except for annealing temperature. Annealing was carried out at 53° C.

Meanwhile, a DNA fragment consisting of the nucleotide sequence ranging from positions 1704 to 2875 of SEQ ID NO: 7 and containing amino acid mutations at positions 403, 404, 405, 406, and 407 is hereinafter referred to as "fragment b'(474,475,476,477,478)."

The composition of the reaction solution for PCR for amplification of fragment b'(474,475,476,477,478) was the same as that employed for amplification of fragment b(446) in Example 12 except for template DNA and primers. The following template DNA and oligo DNA primers were used: pCLuRA-TDH3[Q403P,N404G,T405M,S406L,I407A] (Example 25) (1 μl) (1.45 ng/μl), SQ-CLuc-NF2 (SEQ ID NO: 11), and 3'-UTR (SEQ ID NO: 19). Furthermore, the PCR conditions employed herein were the same as those employed for amplification of fragment a'(238).

The PCR products of the thus obtained fragments a'(238) and b'(474,475,476,477,478) were electrophoresed with 1% agarose, so that they were confirmed to be an approximately 1800-bp DNA fragment and an approximately 1200-bp DNA fragment, respectively. They were mixed and then a mixed solution of fragments a'(238) and b'(474,475,476,477,478) was prepared in a manner similar to that in Example 8.

Next, overlap PCR was carried out using the above mixed solution of fragments a'(238) and b'(474,475,476,477,478) as a template. Thus, one long fragment (the nucleotide sequence ranging from positions 461 to 2663 of SEQ ID NO: 7 was prepared, in which amino acid at target position was substituted. Hereinafter, the DNA fragment is referred to as "fragment c(238,474,475,476,477,478)."

The composition of the reaction solution for PCR for amplification of fragment c(238,474,475,476,477,478) was the same as that employed for amplification of fragment c(475X) in Example 8 except for template DNA and primers. The following template DNA and oligo DNA primers were used: the mixed solution (1 μl) of fragments a'(238) and b'(474,475,476,477,478), SQ-GPD1-F0 (SEQ ID NO: 41), and mut-CLuc-R (SEQ ID NO: 13). Furthermore, the PCR conditions employed herein were the same as those employed for amplification of fragment c(475X) in Example 8, except for annealing temperature and extension time. Annealing was carried out at 51° C. and extension was carried out for 2 minutes and 30 seconds.

Meanwhile, a linear DNA fragment lacking a portion ranging from positions 526 to 2575 of SEQ ID NO: 7 in the sequence of pCLuRA-TDH3 was amplified by PCR. Hereinafter, the DNA fragment is referred to as "fragment d(238, 474,475,476,477,478)."

The composition of the reaction solution for PCR for amplification of fragment d(238,474,475,476,477,478) was the same as that employed for amplification of fragment d in Example 8 except for primers. The following oligo DNA primers were used in the PCR: SQ-GPD1-R0 (SEQ ID NO: 42) and vec-CLuc-F (SEQ ID NO: 14). Furthermore, the PCR conditions employed herein were the same as those employed for amplification of fragment d in Example 8.

The PCR products of fragments c(238,474,475,476,477, 478) and d(238,474,475,476,477,478), were electrophoresed with 0.7% agarose, so that they were confirmed to be an approximately 2200-bp DNA fragment and an approximately 7000-bp DNA fragment, respectively. They were mixed and then a mixed solution of fragments c(238,474,475,476,477, 478) and d(238,474,475,476,477,478) was prepared in a manner similar to that in Example 8.

Next, the emission spectra of the thus obtained clones were measured in a manner similar to that in Example 8 using 10 μl of the mixed solution of fragments c(238,474,475,476,477, 478) and d(238,474,475,476,477,478).

As shown in Table 2, the emission spectral peak of the thus prepared T167K/Q403P/N404G/T405M/S406L/I407A sextuple mutant CLuc (the $3^{rd}$ to the $7^{th}$ mutant luciferases) was 461 nm.

Example 27

K375R/Q403P/N404G/T405M/S406L/I407A Sextuple Mutant CLuc

A gene encoding sextuple (K375R, Q403P, N404G, T405M, S406L, and I407A) mutant CLuc (the $1^{st}$ and the $4^{th}$ to the $7^{th}$ mutant luciferases) with respect to the amino acid sequence shown in SEQ ID NO: 2 was prepared. Furthermore, amino acid at position 21 within the signal sequence of αCLuc shown in SEQ ID NO: 6 was substituted with leucine. Mutagenesis was carried out in a manner similar to that in Example 12.

The DNA fragment consisting of the nucleotide sequence ranging from positions 1 to 2087 of SEQ ID NO: 7 and containing an amino acid mutation at position 21 of SEQ ID NO: 6 and an amino acid mutation at position 375 of SEQ ID NO: 2 was amplified by PCR. Hereinafter, the DNA fragment is referred to as "fragment a(21,446)."

The composition of the reaction solution for PCR for amplification of fragment a(21,446) was the same as that employed for amplification of fragment a(238) in Example 12 except for template DNA and primers. The following template DNA and oligo DNA primers were used: pCLuRA-TDH3[αP21L,K375R] (Example 4) (1 μl) (2.0 ng/μl), FAR-F (SEQ ID NO: 16), and SQ-CLuc-F002-rev (SEQ ID NO: 43). Furthermore, the PCR conditions employed herein were the same as those employed for amplification of fragment a(21) in the section 16-3 of Example 16.

Meanwhile, a DNA fragment consisting of the nucleotide sequence ranging from positions 2064 to 2875 of SEQ ID NO: 7 and containing amino acid mutations at positions 403, 404, 405, 406, and 407 was amplified by PCR. Hereinafter, the DNA fragment is referred to as "fragment b"(474,475, 476,477,478)."

The composition of the reaction solution for PCR for amplification of fragment b"(474,475,476,477,478) was the same as that employed for amplification of fragment a(238) in Example 12 except for template DNA and primers. The following template DNA and oligo DNA primers were used: pCLuRA-TDH3[Q403P,N404G,T405M,S406L,I407A] (Example 25) (1 μl) (1.45 ng/μl), SQ-CLuc-F002 (SEQ ID NO: 44), and 3'-UTR (SEQ ID NO: 19). Furthermore, the PCR conditions employed herein were the same as those employed for amplification of fragment a(21) in the section 16-3 of Example 16.

The PCR products of the thus obtained fragment a(21,446) and fragment b"(474,475,476,477,478) were electrophoresed with 1% agarose, so that they were confirmed to be an approximately 2100-bp DNA fragment and an approximately 800-bp DNA fragment, respectively. They were mixed, so that a mixed solution of fragments a(21,446) and b"(474,475, 476,477,478) was prepared in a manner similar to that in Example 8.

Next, overlap PCR was carried out using the above mixed solution of fragments a(21,446) and b"(474,475,476,477, 478) as a template. Thus, one long fragment (comprising the nucleotide sequence ranging from positions 461 to 2663 of SEQ ID NO: 7) was prepared, in which amino acid at target position was substituted. Hereinafter, the DNA fragment is referred to as "fragment c(21,446,474,475,476,477,478)."

The composition of the reaction solution for PCR for amplification of fragment c(21,446,474,475,476,477,478) was the same as that employed for amplification of fragment c(238,474,475,476,477,478) in Example 26 except for template DNA. The following template DNA was used: the mixed solution (1 μl) of fragments a(21,446) and b"(474,475, 476,477,478). Furthermore, the PCR conditions employed herein were the same as those employed for amplification of fragment c(21,249,268) in the section 16-3 of Example 16.

The thus obtained PCR product of fragment c(21,446,474, 475,476,477,478) was electrophoresed with 0.7% agarose, so that a mixed solution of fragments c(21,446,474,475,476, 477,478) and d(238,474,475,476,477,478) (Example 26) was prepared in a manner similar to that in Example 26.

Next, the emission spectra of the thus obtained clones were measured in a manner similar to that in Example 8 using 10 μl of the mixed solution of fragments c(21,446,474,475,476, 477,478) and d(238,474,475,476,477,478).

As shown in Table 2, the emission spectral peak of the thus prepared K375R/Q403P/N404G/T405M/S406L/I407A sextuple mutant CLuc (the 1$^{st}$ and the 4$^{th}$ to the 7$^{th}$ mutant luciferases) was 460 nm.

Example 28

T167K/K375R/Q403P/N404G/T405M/S406L/I407A Septuple Mutant CLuc

A gene encoding septuple (T167K, K375R, Q403P, N404G, T405M, S406L, and I407A) mutant CLuc (the 1$^{st}$ and the 3$^{rd}$ to the 7$^{th}$ mutant luciferases) with respect to the amino acid sequence shown in SEQ ID NO: 2 was prepared. Furthermore, amino acid at position 21 within the signal sequence of αCLuc shown in SEQ ID NO: 6 was substituted with leucine. Mutagenesis was carried out in a manner similar to that in Example 12.

A DNA fragment consisting of the nucleotide sequence ranging from positions 900 to 2087 of SEQ ID NO: 7 and containing mutations at amino acid positions 167 and 375 was amplified by PCR. Hereinafter, the DNA fragment is referred to as "fragment a'(238,446)."

The composition of the reaction solution for PCR for amplification of fragment a'(238,446) was the same as that employed for amplification of fragment a(238) in Example 12 except for template DNA and primers. The following template DNA and oligo DNA primers were used: pCLuRA-TDH3[T167K,K375R] (Example 12) (11) (3.42 ng/μl), mutCLuc-F (SEQ ID NO: 8), and SQ-CLuc-F002-rev (SEQ ID NO: 43). Furthermore, the PCR conditions employed herein were the same as those employed for amplification of fragment a(21) in the section 16-3 of Example 16.

The PCR product of the thus obtained fragment a'(238, 446) was electrophoresed with 1% agarose, so that it was confirmed to be an approximately 1100-bp DNA fragment. Fragments a'(238,446), a(21) (the section 16-1 of Example 16) and b"(474,475,476,477,478) (Example 27) were mixed, so that a mixed solution of fragments a(21), a'(238,446) and b"(474,475,476,477,478) was prepared in a manner similar to that in Example 8.

Overlap PCR was carried out using the above mixed solution of fragments a(21), a'(238,446) and b"(474,475,476,477, 478) as a template. Thus, one long fragment (consisting of the nucleotide sequence ranging from positions 461 to 2663 of SEQ ID NO: 7) was prepared, in which amino acid at target position was substituted. Hereinafter, the DNA fragment is referred to as "fragment c(21,238,446,474,475,476,477, 478)."

The composition of the reaction solution for PCR for amplification of fragment c(21,238,446,474,475,476,477, 478) was the same as that employed for amplification of fragment c(238,474,475,476,477,478) in Example 26 except for template DNA. The following template DNA was used: the mixed solution (1 μl) of fragments a(21), a'(238,446) and b"(474,475,476,477,478). Furthermore, the PCR conditions employed herein were the same as those employed for amplification of fragment c(21,249,268) in the section 16-3 of Example 16.

The thus obtained PCR product of fragment c(21,238,446, 474,475,476,477,478) was electrophoresed with 0.7% agarose. The experiment was conducted in a manner similar to that in Example 26, so that a mixed solution of fragments c(21,238,446,474,475,476,477,478) and d(238,446,474,475, 476,477,478) (Example 26) was prepared.

Next, the emission spectra of the thus obtained clones were measured in a manner similar to that in Example 8 using 10 μl of the mixed solution of fragments c(21,238,446,474,475, 476,477,478) and d(238,446,474,475,476,477,478).

As shown in Table 2, the emission spectral peak of the thus prepared T167K/K375R/Q403P/N404G/T405M/S406L/ I407A septuple mutant CLuc (the 1$^{st}$ and the 3$^{rd}$ to the 7$^{th}$ mutant luciferases) was 461 nm.

Example 29

Preparation of Mutant CLuc Via Random Mutagenesis of Q403P/N404G/T405M Triple Mutant CLuc 29-1. Introduction of His-tag into the C-Terminus of Q403P/ N404G/T405M Triple Mutant CLuc A CLuc-(GS)3H6 gene was prepared by ligating an His-tag gene downstream of a CLuc gene regarding triple (Q403P, N404G, and T405M) mutant CLuc (the 4th and the 5th mutant luciferases) with respect to the amino acid sequence shown in SEQ ID NO: 2. Furthermore, amino acid at position 21 within the signal sequence of αCLuc shown in SEQ ID NO: 6 was substituted with leucine.

A DNA fragment consisting of the nucleotide sequence ranging from positions 900 to 2552 of SEQ ID NO: 7 and containing amino acid mutations at positions 403, 404, and 405 is hereinafter referred to as "fragment c'(474,475,476)."

The following oligo DNA primers were used for PCR for amplification of fragment c'(474,475,476): mut-CLuc-F (SEQ ID NO: 8) and c-trm-r: ctagggtgtctccatgctttatgta (SEQ ID NO: 53). Furthermore, the composition of the reaction solution for PCR for amplification of fragment c'(474,475,476) was the same as that employed for amplification of fragment c(475X) in Example 8, except for template DNA and primers. The following template DNA was used: pCLuRA-TDH3[Q403P,N404G,T405M] (the section 23-2 of Example 23) (1 µl) (1.82 ng/µl). The PCR conditions employed herein were the same as those employed for amplification of fragment c(475X) in Example 8, except for annealing temperature and extension time. Annealing was carried out at 57° C. and extension was carried out for 2 minutes.

Meanwhile, a linear DNA fragment lacking a portion ranging from positions 967 to 2363 of SEQ ID NO: 7 in the sequence of pCLuRA-TDH3[αP21L,-(GS)3H6] (Example 6) was amplified by PCR. Hereinafter, the DNA fragment is referred to as "fragment d(474,475,476)."

The following primers were used for PCR for amplification of fragment d(474,475,476): vec-CLuc-R (SEQ ID NO: 10) and SQ-CLuc-F003: aagctgaacgactctgcaatagtc (SEQ ID NO: 54). The composition of the reaction solution for PCR for amplification of fragment d(474,475,476) was the same as that employed for amplification of fragment d in Example 8 except for template DNA and primers. The following template DNA was used: pCLuRA-TDH3[αP21L,-(GS)3H6] (Example 6) (1 µl) (1.0 ng/µl). The PCR conditions were the same as those employed for amplification of fragment d in Example 8.

The thus obtained PCR products of fragments c'(474,475,476) and d(474,475,476) were electrophoresed with 0.7% agarose, so that they were confirmed to be an approximately 1700-bp DNA fragment and an approximately 7000-bp DNA fragment, respectively. They were mixed and then a mixed solution of fragments c'(474,475,476) and d(474,475,476) was prepared in a manner similar to that in Example 8.

Next, a clone having, with respect to the amino acid sequence shown in SEQ ID NO: 2, amino acid at position 403 mutated from glutamine to proline, amino acid at position 404 mutated from asparagine to glycine, and amino acid at position 405 mutated from threonine to methionine and having, with respect to the amino acid sequence shown in SEQ ID NO: 6, amino acid at position 21 mutated from proline to leucine and a His-tag gene introduced downstream of the mutant CLuc gene was obtained in a manner similar to that in Example 8 using 10 µl of the mixed solution of fragments c'(474,475,476) and d(474,475,476). A pCLuRA-TDH3 plasmid having, with respect to the amino acid sequence shown in SEQ ID NO: 2, amino acid at position 403 mutated from glutamine to proline, amino acid at position 404 mutated from asparagine to glycine, amino acid at position 405 mutated from threonine to methionine and having, with respect to the amino acid sequence shown in SEQ ID NO: 6, amino acid at position 21 mutated from proline to leucine and a His-tag gene introduced downstream of the mutant CLuc gene, is defined as "pCLuRA-TDH3[αP21L,Q403P,N404G,T405M,-(GS) 3H6]."

29-2. Random Mutagenesis of pCLuRA-TDH3[αP21L, Q403P,N404G,T405M,-(GS)3H6]

pCLuRA-TDH3[αP21L,Q403P,N404G,T405M,-(GS) 3H6] was subjected to random mutation. In addition, an explanation is given using the nucleotide numbers (positions) of SEQ ID NO: 23. Mutagenesis was carried out as follows. CLuc was divided into an N-terminal side portion ranging from positions 900 to 1813 and a C-terminal side portion ranging from 1554 to 2699 of SEQ ID NO: 23 and the portions were separately amplified by PCR using different nucleotide concentrations.

The nucleotide sequence ranging from positions 900 to 1813 of SEQ ID NO: 23 was amplified by error prone PCR. The DNA fragment is referred to as "fragment c(474,475, 476)-N." Furthermore, the nucleotide sequence ranging from positions 1554 to 2699 and containing amino acid mutations at positions 403, 404, and 405 of the amino acid sequence shown in SEQ ID NO: 2 was amplified by error prone PCR. The DNA fragment is referred to as "fragment c(474,475, 476)-C."

The composition of the reaction solution for error prone PCR for amplification of fragment c(474,475,476)-N is as follows: Taq DNA polymerase (Roche): 1 µl (5 U/µl); pCLuRA-TDH3[αP21L,-(GS)3H6] (Example 6) plasmid solution (150 ng/µl): 1 µl; 10×PCR buffer w/o $Mg^{2+}$; for Taq (Roche): 10 µl; 10×dNTP mixture for error prone PCR: 10 µl; 25 mM magnesium chloride: 28 µl; 5 mM manganese chloride: 2.5 µl; mut-CLuc-F (SEQ ID NO: 8): 3 µl; mut-CLuc-NR2 (SEQ ID NO: 9): 3 µl; and sterile water: 41.5 µl. Furthermore, the composition of 10×dNTP mixture for error prone PCR is as follows: 100 mM dCTP: 100 µl; 100 mM dTTP: 100 µl; 100 mM dGTP: 100 µl; 100 mM dATP: 100 µl; and sterile water: 760 µl. PCR was carried out for 30 cycles each consisting of 94° C. for 1 minute (denaturation), 45° C. for 1 minute (annealing), and 72° C. for 1 minute (extension).

Meanwhile, the composition of the reaction solution for error prone PCR for amplification of fragment c(474,475, 476)-C was the same as that employed for error prone PCR for amplification of fragment c(474,475,476)-N, except for template DNA, primers, and the amount of sterile water. The following template DNA, oligo DNA primers, and amount of sterile water were used: pCLuRA-TDH3[αP21L,Q403P, N404G,T405M,-(GS)3H6] (the section 29-1 above) plasmid solution (0.5 µl) (288 ng/µl), mut-CLuc-CF1 (SEQ ID NO: 12) and mut-CLuc-R (SEQ ID NO: 13), and sterile water (42 µl). The PCR conditions were the same as those for error prone PCR for amplification of fragment c(474,475,476)-N.

The thus obtained PCR products of fragments c(474,475, 476)-N and c(474,475,476)-C were electrophoresed with 1% agarose, so that an approximately 900-bp c(474,475,476)-N fragment and an approximately 1100-bp c(474,475,476)-C fragment could be confirmed. They were separately subjected to purification using GeneElute MINUS EtBr SPIN COLUMNS (Sigma), phenol extraction, and then ethanol precipitation. The resultants were each dissolved in 10 µl of sterile water ("a solution of fragment c(474,475,476)-N" and "a solution of fragment c(474,475,476)-C," respectively).

Next, fragments c(474,475,476)-N and c(474,475,476)-C were each amplified by PCR. The thus amplified fragments are defined as "fragment c(474,475,476)-N(2)" and "fragment c(474,475,476)-C(2)," respectively.

The composition of the reaction solution for PCR for amplification of fragment c(474,475,476)-N(2) was the same as that employed for amplification of fragment c(475X) in Example 8, except for template DNA and primers. The following template DNA and oligo DNA primers were used: the solution (1 µl) of fragment c(474,475,476)-N, mut-CLuc-F (SEQ ID NO: 8), and mut-CLuc-NR2 (SEQ ID NO: 9).

Meanwhile, the composition of the reaction solution for PCR for amplification of fragment c(474,475,476)-C(2) was the same as that employed for amplification of fragment c(474,475,476)-N(2), except for template DNA and primers. The following template DNA and oligo DNA primers were used: the solution (1 µl) of fragment c(474,475,476)-C, mut-CLuc-CF1 (SEQ ID NO: 12), and mut-CLuc-R (SEQ ID NO: 13).

Furthermore, the PCR conditions for amplification of fragments c(474,475,476)-N(2) and c(474,475,476)-C(2) were the same as those employed for amplification of fragment c(475X) in Example 8, except for annealing temperature and extension time. Annealing was carried out at 60° C. and extension was carried out for 1 minute and 30 seconds.

The thus obtained PCR products of fragments c(474,475, 476)-N(2) and c(474,475,476)-C(2) were electrophoresed with 1% agarose, so that an approximately 900-bp fragment c(474,475,476)-N(2) and an approximately 1100-bp fragment c(474,475,476)-C(2) could be confirmed. They were each subjected to purification using GeneElute MINUS EtBr SPIN COLUMNS (Sigma), phenol extraction, and then ethanol precipitation. The resultants were each dissolved in 20 µl of sterile water ("a solution of fragment c(474,475,476)-N (2)" and "a solution of fragment c(474,475,476)-C(2)," respectively).

Meanwhile, a linear DNA lacking a portion ranging from positions 967 to 1703 of SEQ ID NO: 23 in the sequence of pCLuRA-TDH3[αP21L,-(GS)3H6] (Example 6) was amplified by PCR. Hereinafter, the DNA fragment is referred to as "fragment d(474,475,476)-N." Furthermore, a linear DNA lacking a portion ranging from 1664 to 2611 of SEQ ID NO: 23 was amplified by PCR. The DNA fragment is referred to as "fragment d(474,475,476)-C."

The composition of the reaction solution for PCR for amplification of fragment d(474,475,476)-N was the same as that employed for amplification of fragment d in Example 8, except for template DNA and primers. The following template DNA and oligo DNA primers were used: pCLuRA-TDH3[αP21L,Q403P,N404G,T405M,-(GS) 3H6] (the section 29-1 above) (1 µl) (288 ng/µl), vec-CLuc-R (SEQ ID NO: 10), and SQ-CLuc-NF2 (SEQ ID NO: 11).

Furthermore, the composition of the reaction solution for PCR for amplification of fragment d(474,475,476)-C was the same as that employed for amplification of fragment d(474, 475,476)-N, except for template DNA and primers. The following template DNA and oligo DNA primers were used: pCLuRA-TDH3[αP21L,-(GS)3H6] (Example 6) (1 µl) (150 ng/µl), SQ-CLuc-CR1 (SEQ ID NO: 15), and vec-CLuc-F (SEQ ID NO: 14).

The PCR conditions for amplification of fragments d(474, 475,476)-N and d(474,475,476)-C were the same as those employed for amplification of fragment d in Example 8.

The thus obtained PCR products of fragments d(474,475, 476)-N and d(474,475,476)-C were electrophoresed with 0.7% agarose, so that an approximately 7000-bp d(474,475, 476)-N fragment and an approximately 7000-bp d(474,475, 476)-C fragment could be confirmed. They were each subjected to purification using GeneElute MINUS EtBr SPIN COLUMNS (Sigma), phenol extraction, and then ethanol precipitation. The resultants were each dissolved in 10 µl of sterile water ("a solution of fragment d(474,475,476)-N" and "a solution of fragment d(474,475,476)-C," respectively).

Next, a mixed solution of fragments c(474,475,476)-N(2) and d(474,475,476)-N was prepared by mixing 10 µl of the solution of fragment c(474,475,476)-N(2) and 5 µl of the solution of fragment d(474,475,476)-N. Similarly, a mixed solution of fragments c(474,475,476)-C(2) and d(474,475, 476)-C was prepared. Transformation was carried out in a manner similar to that in Example 12 using them, thereby constructing "an N-terminal library of αP21L,Q403P, N404G,T405M,-(GS)3H6 mutant" and "a C-terminal library of αP21L,Q403P,N404G,T405M,-(GS)3H6 mutant," respectively.

Hereinafter, in a manner similar to that in Example 8, clones suspected of having undergone emission spectral shift were selected and then the emission spectra were measured.

As shown in Table 2, the emission spectral peaks of the thus selected Y280D/R372L/Q403P/N404G/T405M quintuple mutant CLuc and I276N/Q403P/N404G/T405M quadruple mutant CLuc (the 4$^{th}$ and the 5$^{th}$ mutant luciferases) were both 462 nm.

The above pCLuRA-TDH3 plasmid having, with respect to amino acid sequence shown in SEQ ID NO: 2, amino acid at position 280 mutated from tyrosine to aspartic acid, amino acid at position 372 mutated from arginine to leucine, amino acid at position 403 mutated from glutamine to proline, amino acid at position 404 mutated from asparagine to glycine, amino acid at position 405 mutated from threonine to methionine and having, with respect to the amino acid sequence shown in SEQ ID NO: 6, amino acid at position 21 mutated from proline to leucine and a His-tag gene introduced downstream of the CLuc gene is defined as "pCLuRA-TDH3[αP21L,Y280D,R372L,Q403P,N404G,T405M,-(GS) 3H6]."

Example 30

Preparation of Mutant CLuc Via Random Mutagenesis of Y280D/R372L/Q403P/N404G/T405M Quintuple Mutant CLuc pCLuRA-TDH3[αP21L,Y280D,R372L,Q403P,N404G, T405M,-(GS)3H6] was subjected to random mutation. Mutagenesis was carried out in a manner similar to that in the section 29-2 of Example 29.

In this Example, an explanation is given using nucleotide numbers (positions) of SEQ ID NO: 23. The nucleotide sequence ranging from positions 900 to 1717 of SEQ ID NO: 23 was amplified by error prone PCR. The DNA fragment is referred to as "fragment c(351,443,474,475,476)-N." Furthermore, the nucleotide sequence ranging from positions 1554 to 2699 and containing amino acid mutations at positions 280, 372, 403, 404, and 405 of the amino acid sequence shown in SEQ ID NO: 2 was amplified by error prone PCR. The DNA fragment is referred to as "fragment c(351,443, 474,475,476)-C."

The composition of the reaction solution for error prone PCR for amplification of fragment c(351,443,474,475, 476)-N was the same as that employed for error prone PCR for amplification of fragment c(474,475,476)-C in the section 29-2 of Example 29, except for template DNA and primers. The following template DNA and oligo DNA primers were used: pCLuRA-TDH3[αP21L,Y280D,R372L,Q403P, N404G,T405M,-(GS) 3H6] (the section 29-2 of Example 29) (0.5 µl) (329 ng/µl), mut-CLuc-F (SEQ ID NO: 8), and K340-rev: gtacggctcgagaagaccttt (SEQ ID NO: 55).

Furthermore, the composition of the reaction solution for error prone PCR for amplification of fragment c(351,443, 474,475,476)-C was the same as that for error prone PCR for amplification of fragment c(351,443,474,475,476)-N, except for primers. The following oligo DNA primers were used: mut-CLuc-CF1 (SEQ ID NO: 12) and mut-CLuc-R (SEQ ID NO: 13).

The error prone PCR conditions for amplification of fragments c(351,443,474,475,476)-N and c(351,443,474,475,476)-C were the same as those employed for amplifying fragments c(474,475,476)-N and c(474,475,476)-C, separately in the section 29-2 of Example 29.

A solution of fragment c(351,443,474,475,476)-N and a solution of fragment c(351,443,474,475,476)-C were prepared as follows in a manner similar to that in the section 29-2 of Example 29.

Next, fragments c(351,443,474,475,476)-N and c(351,443,474,475,476)-C were separately amplified by PCR. The thus amplified fragments are referred to as "fragment c(351,443,474,475,476)-N(2)" and "fragment c(351,443,474,475,476)-C (2)," respectively.

The composition of the reaction solution for PCR for amplification of fragment c(351,443,474,475,476)-N(2) was the same as that employed for amplification of fragment c(475X) in Example 8, except for template DNA and primers. The following template DNA and oligo DNA primers were used: a solution of fragment c(351,443,474,475,476)-N, mut-CLuc-F (SEQ ID NO: 8), and K340-rev (SEQ ID NO: 55).

Furthermore, the composition of the reaction solution for PCR for amplification of fragment c(351,443,474,475,476)-C(2) was the same as that employed for amplification of fragment c(474,475,476)-C(2) in the section 29-2 of Example 29, except for template DNA. The following template DNA was used: a solution of fragment c(351,443,474,475,476)-C.

The thus obtained PCR products of fragments c(351,443,474,475,476)-N(2) and c(351,443,474,475,476)-C(2) were electrophoresed with 1% agarose and then a solution of fragment c(474,475,476)-N(2) and a solution of fragment c(474,475,476)-C(2) were prepared in a manner similar to that in the section 29-2 in Example 29.

Meanwhile, a linear DNA lacking a portion ranging from positions 967 to 1703 of SEQ ID NO: 23 in the sequence of pCLuRA-TDH3[αP21L,Y280D,R372L,Q403P,N404G,T405M,-(GS)3H6] was amplified by PCR. Hereinafter, the DNA fragment is referred to as "fragment d(351,443,474,475,476)-N."

The composition of the reaction solution for PCR for amplification of fragment d(351,443,474,475,476)-N was the same as that employed for amplification of fragment d in Example 8, except for template DNA and primers. The following template DNA and oligo DNA primers were used: pCLuRA-TDH3[αP21L,Y280D,R372L,Q403P,N404G,T405M,-(GS)3H6], vec-CLuc-R (SEQ ID NO: 10), and SQ-CLuc-NF2 (SEQ ID NO: 11). Furthermore, the PCR conditions were the same as those employed for amplification of fragment d in Example 8.

Hereinafter, a solution of fragment d(351,443,474,475,476)-N was prepared in a manner similar to that in the section 29-2 of Example 29.

Next, a mixed solution of fragments c(351,443,474,475,476)-N(2) and d(351,443,474,475,476)-N was prepared by mixing 10 μl of the solution of fragment c(351,443,474,475,476)-N(2) with 5 μl of the solution of fragment d(351,443,474,475,476)-N. Similarly, a mixed solution of fragments c(351,443,474,475,476)-C(2) and d(474,475,476)-C was prepared by mixing 10 μl of the solution of fragment c(351,443,474,475,476)-C(2) with 5 μl of the solution of fragment d(474,475,476)-C (the section 29-2 of Example 29). Transformation was carried out in a manner similar to that in Example 12 using them, thereby constructing "an N-terminal library of αP21L,Y280D,R372L,Q403P,N404G,T405M,-(GS)3H6 mutant" and "a C-terminal library of αP21L,Y280D,R372L,Q403P,N404G,T405M,-(GS) 3H6 mutant," respectively.

Hereafter, clones suspected of having undergone emission spectral shift were selected in a manner similar to that in Example 8 and then the emission spectra were measured.

Mutant CLucs contained in the thus selected clones are as shown below.

(1) V258A/Y280D/R372L/Q403P/N404G/T405M/E479V septuple mutant CLuc (in the mutant CLuc, a linker sequence (GSGSGS) located between CLuc and a histidine tag contained an amino acid substitution, however, this was thought to have no effect on the emission spectral peak)

(2) R87S/Y280D/R372L/Q403P/N404G/T405M sextuple mutant CLuc (3) K38R/R79S/Y280D/R372L/Q403P/N404G/T405M septuple mutant CLuc (4) L191Q/Y280D/R372L/Q403P/N404G/T405M sextuple mutant CLuc (5) V75E/K126E/M223I/Y280D/R372L/Q403P/N404G/T405M eightfold mutant CLuc (6) K38I/Y280D/R372L/Q403P/N404G/T405M sextuple mutant CLuc (7) S45G/E170G/Y280D/R372L/Q403P/N404G/T405M septuple mutant CLuc All of them correspond to the 4$^{th}$ and the 5$^{th}$ mutant luciferases. The emission spectral peak of each mutant CLuc is shown in the following Table 2.

TABLE 2

| Mutant CLuc | Maximum emission spectral wavelength (nm) |
|---|---|
| N404G | 458 |
| N404S | 458 |
| T405M | 457 |
| S406L | 460 |
| I407A | 460 |
| T167K/K375R | 460 |
| T167K/Q403P | 458 |
| T167K/N404G | 460 |
| T167K/T405I | 460 |
| M178K/L197P | 447 |
| K375R/Q403P | 460 |
| K375R/N404G | 461 |
| K375R/T405I | 463 |
| Q403P/N404G | 462 |
| Q403P/T405I | 459 |
| N404G/T405I | 461 |
| Q403P/N404G/T405I | 462 |

TABLE 2-continued

| Mutant CLuc | Maximum emission spectral wavelength (nm) |
|---|---|
| Q403P/N404G/T405M | 462 |
| Q403P/N404G/T405M/S406L | 461 |
| Q403P/N404G/T405M/S406L/I407A | 460 |
| T167K/Q403P/N404G/T405M/S406L/I407A | 461 |
| K375R/Q403P/N404G/T405M/S406L/I407A | 460 |
| T167K/K375R/Q403P/N404G/T405M/S406L/I407A | 461 |
| I276N/Q403P/N404G/T405M | 462 |
| Y280D/R372L/Q403P/N404G/T405M | 462 |
| V258A/Y280D/R372L/Q403P/N404G/T405M/E479V | 463 |
| R87S/Y280D/R372L/Q403P/N404G/T405M | 464 |
| K38R/R79S/Y280D/R372L/Q403P/N404G/T405M | 462 |
| L191Q/Y280D/R372L/Q403P/N404G/T405M | 464 |
| V75E/K126E/M223I/Y280D/R372L/Q403P/N404G/T405M | 465 |
| K38I/Y280D/R372L/Q403P/N404G/T405M | 463 |
| S45G/E170G/Y280D/R372L/Q403P/N404G/T405M | 464 |

Among the above clones, a pCLuRA-TDH3 plasmid having, with respect to the amino acid sequence shown in SEQ ID NO: 2, amino acid at position 191 mutated from leucine to glutamine, amino acid at position 280 mutated from tyrosine to aspartic acid, amino acid at position 372 mutated from arginine to leucine, amino acid at position 403 mutated from glutamine to proline, amino acid at position 404 mutated from asparagine to glycine, amino acid at position 405 mutated from threonine to methionine and having, with respect to the amino acid sequence shown in SEQ ID NO: 6, amino acid at position 21 mutated from proline to leucine and a His-Tag gene introduced downstream of the mutant CLuc gene, is defined as "pCLuRA-TDH3[αP21L,L191 Q,Y280D,R372L,Q403P,N404G,T405M-(GS)3H6]."

Example 31

Preparation of Mutant CLuc Via Random Mutagenesis of L191Q/Y280D/R372L/Q403P/N404G/T405M Sextuple Mutant CLuc pCLuRA-TDH3[αP21L,L191Q,Y280D,R372L,Q403P,N404G,T405M-(GS) 3H6] was subjected to random mutation. Mutagenesis was carried out in a manner similar to that in the section 29-2 of Example 29.

In this Example, an explanation is given using the nucleotide positions (numbers) of SEQ ID NO: 23. The nucleotide sequence ranging from positions 900 to 1813 of SEQ ID NO: 23 and containing mutations at positions 191 and 280 of the amino acid sequence shown in SEQ ID NO: 2 was amplified by error prone PCR. The DNA fragment is referred to as "fragment c(262,351,443,474,475,476)-N."

The composition of the reaction solution for error prone PCR for amplification of fragment c(262,351,443,474,475,476)-N was the same as that employed for error prone PCR for amplification of fragment c(474,475,476)-N in the section 29-2 of Example 29, except for template DNA and the amount of sterile water. The following template DNA and amount of sterile water were used: pCLuRA-TDH3[αP21L,L191Q,Y280D,R372L,Q403P,N404G,T405M-(GS)3H6] (Example 30) (0.5 µl) (298 ng/µl) and 42 µl of sterile water. Furthermore, the error prone PCR conditions for amplification of fragment c(262,351,443,474,475,476)-N were the same as those employed for amplification of fragments c(474,475,476)-N and c(474,475,476)-C in the section 29-2 of Example 29.

Hereafter, a solution of fragment c(262,351,443,474,475,476)-N was prepared in a manner similar to that in the section 29-2 of Example 29.

Meanwhile, the nucleotide sequence ranging from positions 900 to 1663 of SEQ ID NO: 23 and containing a mutation at position 191 of the amino acid sequence shown in SEQ ID NO: 2 was amplified by PCR. The thus amplified fragment is referred to as "fragment c(262,351,443,474,475,476)-N(2)."

The composition of the reaction solution for PCR for amplification of fragment c(262,351,443,474,475,476)-N(2) was the same as that employed for amplification of fragment c(475X) in Example 8, except for template DNA and primers. The following template DNA and oligo DNA primers were used: the solution of fragment c(262,351,443,474,475,476)-N, mut-CLuc-F (SEQ ID NO: 8), and SQ-CLuc-CR1 (SEQ ID NO: 15).

The thus obtained PCR product of fragment c(262,351,443,474,475,476)-N(2) was electrophoresed with 1% agarose, so that an approximately 700-bp fragment c(262,351,443,474,475,476)-N(2) could be confirmed. Hereafter, a solution of fragment c(262,351,443,474,475,476)-N(2) was prepared in a manner similar to that in the section 29-2 of Example 29.

Furthermore, linear DNA lacking positions 1664 to 2611 of SEQ ID NO: 23 in the sequence of pCLuRA-TDH3 [αP21L,L191Q,Y280D,R372L,Q403P,N404G,T405M-(GS) 3H6] and containing a mutation at position 191 of the amino acid sequence shown in SEQ ID NO: 2 was amplified by PCR. The DNA fragment is referred to as "fragment d(262,351,443,474,475,476)-C."

The composition of the reaction solution for amplification of fragment d(262,351,443,474,475,476)-C was the same as that employed for amplification of fragment d(474,475,476)-C in the section 29-2 of Example 29, except for template DNA. The following template DNA was used: pCLuRA-TDH3[αP21L,L191Q,Y280D,R372L,Q403P,N404G,T405M-(GS)3H6]. Furthermore, the PCR conditions for amplification of fragment d(262,351,443,474,475,476)-C were the same as those employed for amplification of fragment d in Example 8.

Hereafter, a solution of fragment d(262,351,443,474,475,476)-C was prepared in a manner similar to that in the section 29-2 of Example 29.

Next, a mixed solution of fragments c(262,351,443,474,475,476)-N(2) and d(351,443,474,475,476)-N was prepared by mixing 10 µl of the solution of fragment c(262,351,443,474,475,476)-N(2) with 5 µl of the solution of fragment d(351,443,474,475,476)-N (Example 30). Similarly, a mixed solution of fragments c(351,443,474,475,476)-N(2) and d(262,351,443,474,475,476) was prepared by mixing 10 μl of the solution of fragment c(351,443,474,475,476)-N(2) (Example 30) with 5 μl of the solution of fragment d(262,351, 443,474,475,476)-C. Transformation was carried out using them in a manner similar to that in Example 12, thereby constructing "an N-terminal library of αP21L,L262Q, Y351D,R443L,Q474P,N475G,T476M,-(GS)3H6 mutant" and "a C-terminal library of αP21L,L262Q,Y351D,R443L, Q474P,N475G,T476M,-(GS)3H6 mutant."

Hereafter, clones suspected of having undergone emission spectral shift were selected in a manner similar to that in Example 8 and then the emission spectra were measured.

The emission spectral peak of the thus selected L191Q/Q235R/Y280D/R372L/Q403P/N404G/T405M septuple mutant CLuc (the 8th mutant luciferase) was 466 nm. Furthermore, the emission spectral peak of M178R/L191Q/Y280D/R372L/Q403P/N404G/T405M septuple mutant CLuc (the 9th mutant luciferase) was 435 nm. The difference between the two mutant CLucs in terms of peak wavelength was 31 nm. Thus, two types of mutant luciferase differing in terms of luminescent color were obtained, which can be sufficiently separated with the use of optical filters and program analysis.

All publications, patents, and patent applications cited herein are incorporated herein by reference in their entirety.

The invention claimed is:

1. A mutant luciferase selected from the following (a) to (d):
   (a) a protein comprising the amino acid sequence of SEQ ID NO: 2, but in which the methionine at position 178 is substituted with another amino acid;
   (b) a protein comprising an amino acid sequence at least 90% identical to SEQ ID NO: 2, wherein the residue corresponding to the methionine at position 178 in SEQ ID NO: 2 is substituted with another amino acid, and wherein said protein has luciferase activity with an emission spectral peak of 449 nm or less;
   (c) a protein comprising residues 19-553 of SEQ ID NO: 2, but in which the methionine at position 178 is substituted with another amino acid; and
   (d) a protein comprising an amino acid sequence at least 90% identical to residues 19-553 of SEQ ID NO: 2, wherein the residue corresponding to the methionine at position 178 in SEQ ID NO: 2 is substituted with another amino acid, and wherein said protein has luciferase activity with an emission spectral peak of 449 nm or less.

2. The mutant luciferase according to claim 1, wherein said substitution is with lysine.

3. The mutant luciferase according to claim 1, wherein the emission spectral peak ranges from 420 nm to 449 nm.

4. A mutant luciferase selected from the following (a) to (d):
   (a) a protein comprising the amino acid sequence of SEQ ID NO: 2, but in which the methionine at position 178, the leucine at position 191, the tyrosine at position 280, the arginine at position 372, the glutamine at position 403, the asparagine at position 404, and the threonine at position 405, are substituted with other amino acids;
   (b) a protein comprising an amino acid sequence at least 90% identical to SEQ ID NO: 2, wherein the residues corresponding to the methionine at position 178, the leucine at position 191, the tyrosine at position 280, the arginine at position 372, the glutamine at position 403, the asparagine at position 404, and the threonine at position 405 of SEQ ID NO: 2, are substituted with other amino acids, and wherein said protein has luciferase activity with an emission spectral peak of 435 nm or less;
   (c) a protein comprising residues 19-553 of SEQ ID NO: 2, but in which the methionine at position 178, the leucine at position 191, the tyrosine at position 280, the arginine at position 372, the glutamine at position 403, the asparagine at position 404, and the threonine at position 405, are substituted with other amino acids; and
   (d) a protein comprising an amino acid sequence at least 90% identical to residues 19-553 of SEQ ID NO: 2, wherein the residues corresponding to the methionine at position 178, the leucine at position 191, the tyrosine at position 280, the arginine at position 372, the glutamine at position 403, the asparagine at position 404, and the threonine at position 405 of SEQ ID NO: 2, are substituted with other amino acids, and wherein said protein has luciferase activity with an emission spectral peak of 435 nm or less.

5. A fusion protein, wherein a foreign protein or peptide is linked to the mutant luciferase according to any one of claims 1 and 4.

6. A polynucleotide encoding the mutant luciferase according to any one of claims 1 and 4, or encoding the fusion protein according to claim 5.

7. A recombinant vector comprising the polynucleotide according to claim 6.

8. A transformant comprising the recombinant vector according to claim 7.

9. The transformant according to claim 8, wherein said transformant comprises the polynucleotide of claim 6 operatively linked to a first promoter sequence, and further comprises polynucleotide encoding a protein selected from the following (a) to (c) operatively linked to a second promoter, wherein said first and second promoters are different:
   (a) a protein comprising the amino acid sequence of SEQ ID NO: 2;
   (b) a protein comprising residues 19-553 of SEQ ID NO: 2; and
   (c) a fusion protein in which a foreign protein or peptide is linked to the protein of (a) or (b).

10. A method for comparing the transcriptional activity of different promoters, comprising the steps of:
   (a) causing a culture or a culture supernatant of the transformant according to claim 9 to come into contact with a luciferin or a derivative thereof; and
   (b) measuring the luminescence intensity of the emission spectrum based on the activity of each luciferase.

* * * * *

SEQUENCE LISTING

<160> NUMBER OF SEQ ID NOS: 55

<210> SEQ ID NO 1
<211> LENGTH: 1662
<212> TYPE: DNA
<213> ORGANISM: Cypridina noctiluca
<220> FEATURE:
<221> NAME/KEY: CDS
<222> LOCATION: (1)..(1662)

<400> SEQUENCE: 1

```
atg aag acc tta att ctt gcc gtt gca tta gtc tac tgc gcc act gtt      48
Met Lys Thr Leu Ile Leu Ala Val Ala Leu Val Tyr Cys Ala Thr Val
 1               5                  10                  15 cat tgc cag gac tgt cct tac gaa cct gat cca cca aac aca gtt cca      96
His Cys Gln Asp Cys Pro Tyr Glu Pro Asp Pro Pro Asn Thr Val Pro
             20                  25                  30 act tcc tgt gaa gct aaa gaa gga gaa tgt att gat agc agc tgt ggc     144
Thr Ser Cys Glu Ala Lys Glu Gly Glu Cys Ile Asp Ser Ser Cys Gly
         35                  40                  45 acc tgc acg aga gac ata cta tca gat gga ctg tgt gaa aat aaa cca     192
Thr Cys Thr Arg Asp Ile Leu Ser Asp Gly Leu Cys Glu Asn Lys Pro
     50                  55                  60 gga aaa aca tgt tgc cga atg tgt cag tat gta att gaa tgc aga gta     240
Gly Lys Thr Cys Cys Arg Met Cys Gln Tyr Val Ile Glu Cys Arg Val
 65                  70                  75                  80 gag gct gca gga tgg ttt aga aca ttc tat gga aag aga ttc cag ttc     288
Glu Ala Ala Gly Trp Phe Arg Thr Phe Tyr Gly Lys Arg Phe Gln Phe
                 85                  90                  95 cag gaa cct ggt aca tac gtg ttg ggt caa gga acc aag ggc ggc gac     336
Gln Glu Pro Gly Thr Tyr Val Leu Gly Gln Gly Thr Lys Gly Gly Asp
            100                 105                 110 tgg aag gtg tcc atc acc ctg gag aac ctg gat gga acc aag ggg gct     384
Trp Lys Val Ser Ile Thr Leu Glu Asn Leu Asp Gly Thr Lys Gly Ala
        115                 120                 125 gtg ctg acc aag aca aga ctg gaa gtg gct gga gac atc att gac atc     432
Val Leu Thr Lys Thr Arg Leu Glu Val Ala Gly Asp Ile Ile Asp Ile
    130                 135                 140 gct caa gct act gag aat ccc atc act gta aac ggt gga gct gac cct     480
Ala Gln Ala Thr Glu Asn Pro Ile Thr Val Asn Gly Gly Ala Asp Pro
145                 150                 155                 160 atc atc gcc aac ccg tac acc atc ggc gag gtc acc atc gct gtt gtt     528
Ile Ile Ala Asn Pro Tyr Thr Ile Gly Glu Val Thr Ile Ala Val Val
                165                 170                 175 gag atg cca ggc ttc aac atc acc gtc ata gaa ttc ttc aaa ctg atc     576
Glu Met Pro Gly Phe Asn Ile Thr Val Ile Glu Phe Phe Lys Leu Ile
            180                 185                 190
```

```
gtg atc gac atc ctc gga gga aga tct gta aga atc gcc cca gac aca      624
Val Ile Asp Ile Leu Gly Gly Arg Ser Val Arg Ile Ala Pro Asp Thr
        195                 200                 205 gca aac aaa gga atg atc tct ggc ctc tgt gga gat ctt aaa atg atg      672
Ala Asn Lys Gly Met Ile Ser Gly Leu Cys Gly Asp Leu Lys Met Met
    210                 215                 220 gaa gat aca gac ttc act tca gat cca gaa caa ctc gct att cag cct      720
Glu Asp Thr Asp Phe Thr Ser Asp Pro Glu Gln Leu Ala Ile Gln Pro
225                 230                 235                 240 aag atc aac cag gag ttt gac ggt tgt cca ctc tat gga aat cct gat      768
Lys Ile Asn Gln Glu Phe Asp Gly Cys Pro Leu Tyr Gly Asn Pro Asp
                245                 250                 255 gac gtt gca tac tgc aaa ggt ctt ctc gag ccg tac aag gac agc tgc      816
Asp Val Ala Tyr Cys Lys Gly Leu Leu Glu Pro Tyr Lys Asp Ser Cys
            260                 265                 270 cgc aac ccc atc aac ttc tac tac tac acc atc tcc tgc gcc ttc gcc      864
Arg Asn Pro Ile Asn Phe Tyr Tyr Tyr Thr Ile Ser Cys Ala Phe Ala
        275                 280                 285 cgc tgt atg ggt gga gac gag cga gcc tca cac gtg ctg ctt gac tac      912
Arg Cys Met Gly Gly Asp Glu Arg Ala Ser His Val Leu Leu Asp Tyr
    290                 295                 300 agg gag acg tgc gct gct ccc gaa act aga gga acc tgc gtt ttg tct      960
Arg Glu Thr Cys Ala Ala Pro Glu Thr Arg Gly Thr Cys Val Leu Ser
305                 310                 315                 320 gga cat act ttc tac gat aca ttt gac aaa gca aga tat caa ttc cag     1008
Gly His Thr Phe Tyr Asp Thr Phe Asp Lys Ala Arg Tyr Gln Phe Gln
                325                 330                 335 ggt ccc tgc aag gag att ctt atg gcc gcc gac tgt ttc tgg aac act     1056
Gly Pro Cys Lys Glu Ile Leu Met Ala Ala Asp Cys Phe Trp Asn Thr
            340                 345                 350 tgg gat gtg aag gtt tca cac agg aat gtt gac tct tac act gaa gta     1104
Trp Asp Val Lys Val Ser His Arg Asn Val Asp Ser Tyr Thr Glu Val
        355                 360                 365 gag aaa gta cga atc agg aaa caa tcg act gta gta gaa ctc att gtt     1152
Glu Lys Val Arg Ile Arg Lys Gln Ser Thr Val Val Glu Leu Ile Val
    370                 375                 380 gat gga aaa cag att ctg gtt gga gga gaa gcc gtg tcc gtc ccg tac     1200
Asp Gly Lys Gln Ile Leu Val Gly Gly Glu Ala Val Ser Val Pro Tyr
385                 390                 395                 400 agc tct cag aac act tcc atc tac tgg caa gat ggt gac ata ctg act     1248
Ser Ser Gln Asn Thr Ser Ile Tyr Trp Gln Asp Gly Asp Ile Leu Thr
                405                 410                 415 aca gcc atc cta cct gaa gct ctg gtg gtc aag ttc aac ttc aag caa     1296
Thr Ala Ile Leu Pro Glu Ala Leu Val Val Lys Phe Asn Phe Lys Gln
            420                 425                 430 ctg ctc gtc gta cat att aga gat cca ttc gat ggt aag act tgc ggt     1344
Leu Leu Val Val His Ile Arg Asp Pro Phe Asp Gly Lys Thr Cys Gly
        435                 440                 445 att tgc ggt aac tac aac cag gat ttc agt gat gat tct ttt gat gct     1392
Ile Cys Gly Asn Tyr Asn Gln Asp Phe Ser Asp Asp Ser Phe Asp Ala
    450                 455                 460 gaa gga gcc tgt gat ctg acc ccc aac cca ccg gga tgc acc gaa gaa     1440
Glu Gly Ala Cys Asp Leu Thr Pro Asn Pro Pro Gly Cys Thr Glu Glu
465                 470                 475                 480 cag aaa cct gaa gct gaa cga ctc tgc aat agt ctc ttc gcc ggt caa     1488
Gln Lys Pro Glu Ala Glu Arg Leu Cys Asn Ser Leu Phe Ala Gly Gln
                485                 490                 495 agt gat ctt gat cag aaa tgt aac gtg tgc cac aag cct gac cgt gtc     1536
Ser Asp Leu Asp Gln Lys Cys Asn Val Cys His Lys Pro Asp Arg Val
            500                 505                 510
```

```
gaa cga tgc atg tac gag tat tgc ctg agg gga caa cag ggt ttc tgt    1584
Glu Arg Cys Met Tyr Glu Tyr Cys Leu Arg Gly Gln Gln Gly Phe Cys
    515                 520                 525 gac cac gca tgg gag ttc aag aaa gaa tgc tac ata aag cat gga gac    1632
Asp His Ala Trp Glu Phe Lys Lys Glu Cys Tyr Ile Lys His Gly Asp
530                 535                 540 acc cta gaa gta cca gat gaa tgc aaa tag                            1662
Thr Leu Glu Val Pro Asp Glu Cys Lys
545                 550

<210> SEQ ID NO 2
<211> LENGTH: 553
<212> TYPE: PRT
<213> ORGANISM: Cypridina noctiluca

<400> SEQUENCE: 2

Met Lys Thr Leu Ile Leu Ala Val Ala Leu Val Tyr Cys Ala Thr Val
 1               5                  10                  15

His Cys Gln Asp Cys Pro Tyr Glu Pro Asp Pro Pro Asn Thr Val Pro
            20                  25                  30

Thr Ser Cys Glu Ala Lys Glu Gly Glu Cys Ile Asp Ser Ser Cys Gly
        35                  40                  45

Thr Cys Thr Arg Asp Ile Leu Ser Asp Gly Leu Cys Glu Asn Lys Pro
    50                  55                  60

Gly Lys Thr Cys Cys Arg Met Cys Gln Tyr Val Ile Glu Cys Arg Val
65                  70                  75                  80

Glu Ala Ala Gly Trp Phe Arg Thr Phe Tyr Gly Lys Arg Phe Gln Phe
                85                  90                  95

Gln Glu Pro Gly Thr Tyr Val Leu Gly Gln Gly Thr Lys Gly Gly Asp
            100                 105                 110

Trp Lys Val Ser Ile Thr Leu Glu Asn Leu Asp Gly Thr Lys Gly Ala
        115                 120                 125

Val Leu Thr Lys Thr Arg Leu Glu Val Ala Gly Asp Ile Ile Asp Ile
    130                 135                 140

Ala Gln Ala Thr Glu Asn Pro Ile Thr Val Asn Gly Gly Ala Asp Pro
145                 150                 155                 160

Ile Ile Ala Asn Pro Tyr Thr Ile Gly Glu Val Thr Ile Ala Val Val
                165                 170                 175

Glu Met Pro Gly Phe Asn Ile Thr Val Ile Glu Phe Phe Lys Leu Ile
            180                 185                 190

Val Ile Asp Ile Leu Gly Gly Arg Ser Val Arg Ile Ala Pro Asp Thr
        195                 200                 205

Ala Asn Lys Gly Met Ile Ser Gly Leu Cys Gly Asp Leu Lys Met Met
210                 215                 220

Glu Asp Thr Asp Phe Thr Ser Asp Pro Glu Gln Leu Ala Ile Gln Pro
225                 230                 235                 240

Lys Ile Asn Gln Glu Phe Asp Gly Cys Pro Leu Tyr Gly Asn Pro Asp
                245                 250                 255

Asp Val Ala Tyr Cys Lys Gly Leu Leu Glu Pro Tyr Lys Asp Ser Cys
            260                 265                 270

Arg Asn Pro Ile Asn Phe Tyr Tyr Tyr Thr Ile Ser Cys Ala Phe Ala
        275                 280                 285

Arg Cys Met Gly Gly Asp Glu Arg Ala Ser His Val Leu Leu Asp Tyr
    290                 295                 300

Arg Glu Thr Cys Ala Ala Pro Glu Thr Arg Gly Thr Cys Val Leu Ser
305                 310                 315                 320
```

```
Gly His Thr Phe Tyr Asp Thr Phe Asp Lys Ala Arg Tyr Gln Phe Gln
                325                 330                 335

Gly Pro Cys Lys Glu Ile Leu Met Ala Ala Asp Cys Phe Trp Asn Thr
            340                 345                 350

Trp Asp Val Lys Val Ser His Arg Asn Val Asp Ser Tyr Thr Glu Val
                355                 360                 365

Glu Lys Val Arg Ile Arg Lys Gln Ser Thr Val Val Glu Leu Ile Val
        370                 375                 380

Asp Gly Lys Gln Ile Leu Val Gly Glu Ala Val Ser Val Pro Tyr
385                 390                 395                 400

Ser Ser Gln Asn Thr Ser Ile Tyr Trp Gln Gly Asp Ile Leu Thr
                405                 410                 415

Thr Ala Ile Leu Pro Glu Ala Leu Val Val Lys Phe Asn Phe Lys Gln
                420                 425                 430

Leu Leu Val Val His Ile Arg Asp Pro Phe Asp Gly Lys Thr Cys Gly
            435                 440                 445

Ile Cys Gly Asn Tyr Asn Gln Asp Phe Ser Asp Ser Phe Asp Ala
        450                 455                 460

Glu Gly Ala Cys Asp Leu Thr Pro Asn Pro Gly Cys Thr Glu Glu
465                 470                 475                 480

Gln Lys Pro Glu Ala Glu Arg Leu Cys Asn Ser Leu Phe Ala Gly Gln
                485                 490                 495

Ser Asp Leu Asp Gln Lys Cys Asn Val Cys His Lys Pro Asp Arg Val
                500                 505                 510

Glu Arg Cys Met Tyr Glu Tyr Cys Leu Arg Gly Gln Gln Gly Phe Cys
            515                 520                 525

Asp His Ala Trp Glu Phe Lys Lys Glu Cys Tyr Ile Lys His Gly Asp
        530                 535                 540

Thr Leu Glu Val Pro Asp Glu Cys Lys
545                 550

<210> SEQ ID NO 3
<211> LENGTH: 89
<212> TYPE: PRT
<213> ORGANISM: Saccharomyces cerevisiae

<400> SEQUENCE: 3

Met Arg Phe Pro Ser Ile Phe Thr Ala Val Leu Phe Ala Ala Ser Ser
 1               5                  10                  15

Ala Leu Ala Ala Pro Val Asn Thr Thr Thr Glu Asp Glu Thr Ala Gln
             20                  25                  30

Ile Pro Ala Glu Ala Val Ile Gly Tyr Ser Asp Leu Glu Gly Asp Phe
         35                  40                  45

Asp Val Ala Val Leu Pro Phe Ser Asn Ser Thr Asn Asn Gly Leu Leu
     50                  55                  60

Phe Ile Asn Thr Thr Ile Ala Ser Ile Ala Ala Lys Glu Glu Gly Val
 65                  70                  75                  80

Ser Leu Glu Lys Arg Glu Ala Glu Ala
                 85

<210> SEQ ID NO 4
<211> LENGTH: 19
<212> TYPE: PRT
<213> ORGANISM: Saccharomyces cerevisiae

<400> SEQUENCE: 4

Met Leu Leu Gln Ala Phe Leu Phe Leu Leu Ala Gly Phe Ala Ala Lys
```

<210> SEQ ID NO 5
<211> LENGTH: 62
<212> TYPE: PRT
<213> ORGANISM: Saccharomyces cerevisiae

<400> SEQUENCE: 5

```
Met Asn Phe Leu Ser Phe Lys Thr Thr Lys His Tyr His Ile Phe Arg
 1               5                  10                  15

Tyr Val Asn Ile Arg Asn Asp Tyr Arg Leu Leu Met Ile Met Ile Ile
                20                  25                  30

Gly Thr Val Ala Thr Gly Leu Val Pro Ala Ile Thr Ser Ile Leu Thr
            35                  40                  45

Gly Arg Val Phe Asp Leu Leu Ser Val Phe Val Ala Asn Gly
        50                  55                  60
```

<210> SEQ ID NO 6
<211> LENGTH: 624
<212> TYPE: PRT
<213> ORGANISM: Artificial Sequence
<220> FEATURE:
<223> OTHER INFORMATION: Synthetic fusion protein

<400> SEQUENCE: 6

```
Met Arg Phe Pro Ser Ile Phe Thr Ala Val Leu Phe Ala Ala Ser Ser
 1               5                  10                  15

Ala Leu Ala Ala Pro Val Asn Thr Thr Thr Glu Asp Glu Thr Ala Gln
                20                  25                  30

Ile Pro Ala Glu Ala Val Ile Gly Tyr Ser Asp Leu Glu Gly Asp Phe
            35                  40                  45

Asp Val Ala Val Leu Pro Phe Ser Asn Ser Thr Asn Asn Gly Leu Leu
        50                  55                  60

Phe Ile Asn Thr Thr Ile Ala Ser Ile Ala Ala Lys Glu Glu Gly Val
 65                  70                  75                  80

Ser Leu Glu Lys Arg Glu Ala Glu Ala Gln Asp Cys Pro Tyr Glu Pro
                85                  90                  95

Asp Pro Pro Asn Thr Val Pro Thr Ser Cys Glu Ala Lys Glu Gly Glu
            100                 105                 110

Cys Ile Asp Ser Ser Cys Gly Thr Cys Thr Arg Asp Ile Leu Ser Asp
        115                 120                 125

Gly Leu Cys Glu Asn Lys Pro Gly Lys Thr Cys Cys Arg Met Cys Gln
    130                 135                 140

Tyr Val Ile Glu Cys Arg Val Glu Ala Ala Gly Trp Phe Arg Thr Phe
145                 150                 155                 160

Tyr Gly Lys Arg Phe Gln Phe Gln Glu Pro Gly Thr Tyr Val Leu Gly
                165                 170                 175

Gln Gly Thr Lys Gly Gly Asp Trp Lys Val Ser Ile Thr Leu Glu Asn
            180                 185                 190

Leu Asp Gly Thr Lys Gly Ala Val Leu Thr Lys Thr Arg Leu Glu Val
        195                 200                 205

Ala Gly Asp Ile Ile Asp Ile Ala Gln Ala Thr Glu Asn Pro Ile Thr
    210                 215                 220

Val Asn Gly Gly Ala Asp Pro Ile Ile Ala Asn Pro Tyr Thr Ile Gly
225                 230                 235                 240

Glu Val Thr Ile Ala Val Val Glu Met Pro Gly Phe Asn Ile Thr Val
```

```
                245                 250                 255
Ile Glu Phe Phe Lys Leu Ile Val Ile Asp Ile Leu Gly Gly Arg Ser
                260                 265                 270

Val Arg Ile Ala Pro Asp Thr Ala Asn Lys Gly Met Ile Ser Gly Leu
            275                 280                 285

Cys Gly Asp Leu Lys Met Met Glu Asp Thr Asp Phe Thr Ser Asp Pro
        290                 295                 300

Glu Gln Leu Ala Ile Gln Pro Lys Ile Asn Gln Glu Phe Asp Gly Cys
305                 310                 315                 320

Pro Leu Tyr Gly Asn Pro Asp Asp Val Ala Tyr Cys Lys Gly Leu Leu
                325                 330                 335

Glu Pro Tyr Lys Asp Ser Cys Arg Asn Pro Ile Asn Phe Tyr Tyr Tyr
            340                 345                 350

Thr Ile Ser Cys Ala Phe Ala Arg Cys Met Gly Gly Asp Glu Arg Ala
        355                 360                 365

Ser His Val Leu Leu Asp Tyr Arg Glu Thr Cys Ala Ala Pro Glu Thr
    370                 375                 380

Arg Gly Thr Cys Val Leu Ser Gly His Thr Phe Tyr Asp Thr Phe Asp
385                 390                 395                 400

Lys Ala Arg Tyr Gln Phe Gln Gly Pro Cys Lys Glu Ile Leu Met Ala
                405                 410                 415

Ala Asp Cys Phe Trp Asn Thr Trp Asp Val Lys Val Ser His Arg Asn
            420                 425                 430

Val Asp Ser Tyr Thr Glu Val Glu Lys Val Arg Ile Arg Lys Gln Ser
        435                 440                 445

Thr Val Val Glu Leu Ile Val Asp Gly Lys Gln Ile Leu Val Gly Gly
    450                 455                 460

Glu Ala Val Ser Val Pro Tyr Ser Ser Gln Asn Thr Ser Ile Tyr Trp
465                 470                 475                 480

Gln Asp Gly Asp Ile Leu Thr Thr Ala Ile Leu Pro Glu Ala Leu Val
                485                 490                 495

Val Lys Phe Asn Phe Lys Gln Leu Leu Val Val His Ile Arg Asp Pro
            500                 505                 510

Phe Asp Gly Lys Thr Cys Gly Ile Cys Gly Asn Tyr Asn Gln Asp Phe
        515                 520                 525

Ser Asp Asp Ser Phe Asp Ala Glu Gly Ala Cys Asp Leu Thr Pro Asn
    530                 535                 540

Pro Pro Gly Cys Thr Glu Glu Gln Lys Pro Glu Ala Glu Arg Leu Cys
545                 550                 555                 560

Asn Ser Leu Phe Ala Gly Gln Ser Asp Leu Asp Gln Lys Cys Asn Val
                565                 570                 575

Cys His Lys Pro Asp Arg Val Glu Arg Cys Met Tyr Glu Tyr Cys Leu
            580                 585                 590

Arg Gly Gln Gln Gly Phe Cys Asp His Ala Trp Glu Phe Lys Lys Glu
        595                 600                 605

Cys Tyr Ile Lys His Gly Asp Thr Leu Glu Val Pro Asp Glu Cys Lys
    610                 615                 620

<210> SEQ ID NO 7
<211> LENGTH: 2875
<212> TYPE: DNA
<213> ORGANISM: Artificial Sequence
<220> FEATURE:
<223> OTHER INFORMATION: Partial nucleotide sequence of plasmid
      pCLuRA-TDH3
<220> FEATURE:
```

<221> NAME/KEY: CDS
<222> LOCATION: (701)..(2575)

<400> SEQUENCE: 7

```
aaccctcact aaagggaaca aaagctggct agaactagtg gatcccgagt ttatcattat    60
caatactgcc atttcaaaga atacgtaaat aattaatagt agtgattttc ctaactttat   120
ttagtcaaaa aattagcctt ttaattctgc tgtaacccgt acatgcccaa aataggggc    180 gggttacaca gaatatataa catcgtaggt gtctgggtga acagtttatt cctggcatcc   240
actaaatata atggagcccg ctttttaagc tggcatccag aaaaaaaaag aatcccagca   300
ccaaaatatt gttttcttca ccaaccatca gttcataggc ccattctctt agcgcaacta   360
cagagaacag gggcacaaac aggcaaaaaa cgggcacaac ctcaatggag tgatgcaacc   420
tgcctggagt aaatgatgac acaaggcaat tgacccacgc atgtatctat ctcattttct   480
tacaccttct attaccttct gctctctctg atttggaaaa agctgaaaaa aaaggttgaa   540
accagttccc tgaaattatt cccctacttg actaataagt atataaagac ggtaggtatt   600
gattgtaatt ctgtaaatct atttcttaaa cttcttaaat tctacttttta tagttagtct   660 ttttttttagt tttaaaacac caagaactta gtttcgaggg atg aga ttt cct tca    715
                                               Met Arg Phe Pro Ser
                                                 1               5 att ttt act gct gtt tta ttc gca gca tcc tcc gca tta gct gct cca    763
Ile Phe Thr Ala Val Leu Phe Ala Ala Ser Ser Ala Leu Ala Ala Pro
           10                  15                  20 gtc aac act aca aca gaa gat gaa acg gca caa att ccg gct gaa gct    811
Val Asn Thr Thr Thr Glu Asp Glu Thr Ala Gln Ile Pro Ala Glu Ala
         25                  30                  35 gtc atc ggt tac tca gat tta gaa ggg gat ttc gat gtt gct gtt ttg    859
Val Ile Gly Tyr Ser Asp Leu Glu Gly Asp Phe Asp Val Ala Val Leu
     40                  45                  50 cca ttt tcc aac agc aca aat aac ggg tta ttg ttt ata aat act act    907
Pro Phe Ser Asn Ser Thr Asn Asn Gly Leu Leu Phe Ile Asn Thr Thr
 55                  60                  65 att gcc agc att gct gct aaa gaa gaa ggg gta tct ctc gag aaa aga    955
Ile Ala Ser Ile Ala Ala Lys Glu Glu Gly Val Ser Leu Glu Lys Arg
 70                  75                  80                  85 gag gct gaa gct cag gac tgt cct tac gaa cct gat cca cca aac aca   1003
Glu Ala Glu Ala Gln Asp Cys Pro Tyr Glu Pro Asp Pro Pro Asn Thr
             90                  95                 100 gtt cca act tcc tgt gaa gct aaa gaa gga gaa tgt att gat agc agc   1051
Val Pro Thr Ser Cys Glu Ala Lys Glu Gly Glu Cys Ile Asp Ser Ser
        105                 110                 115 tgt ggc acc tgc acg aga gac ata cta tca gat gga ctg tgt gaa aat   1099
Cys Gly Thr Cys Thr Arg Asp Ile Leu Ser Asp Gly Leu Cys Glu Asn
    120                 125                 130 aaa cca gga aaa aca tgt tgc cga atg tgt cag tat gta att gaa tgc   1147
Lys Pro Gly Lys Thr Cys Cys Arg Met Cys Gln Tyr Val Ile Glu Cys
135                 140                 145 aga gta gag gct gca gga tgg ttt aga aca ttc tat gga aag aga ttc   1195
Arg Val Glu Ala Ala Gly Trp Phe Arg Thr Phe Tyr Gly Lys Arg Phe
150                 155                 160                 165 cag ttc cag gaa cct ggt aca tac gtg ttg ggt caa gga acc aag ggc   1243
Gln Phe Gln Glu Pro Gly Thr Tyr Val Leu Gly Gln Gly Thr Lys Gly
            170                 175                 180 ggc gac tgg aag gtg tcc atc acc ctg gag aac ctg gat gga acc aag   1291
Gly Asp Trp Lys Val Ser Ile Thr Leu Glu Asn Leu Asp Gly Thr Lys
        185                 190                 195 ggg gct gtg ctg acc aag aca aga ctg gaa gtg gct gga gac atc att   1339
```

-continued

```
                Gly Ala Val Leu Thr Lys Thr Arg Leu Glu Val Ala Gly Asp Ile Ile
                            200                 205                 210 gac atc gct caa gct act gag aat ccc atc act gta aac ggt gga gct        1387
Asp Ile Ala Gln Ala Thr Glu Asn Pro Ile Thr Val Asn Gly Gly Ala
215                 220                 225 gac cct atc atc gcc aac ccg tac acc atc ggc gag gtc acc atc gct        1435
Asp Pro Ile Ile Ala Asn Pro Tyr Thr Ile Gly Glu Val Thr Ile Ala
230                 235                 240                 245 gtt gtt gag atg cca ggc ttc aac atc acc gtc ata gaa ttc ttc aaa        1483
Val Val Glu Met Pro Gly Phe Asn Ile Thr Val Ile Glu Phe Phe Lys
                250                 255                 260 ctg atc gtg atc gac atc ctc gga gga aga tct gta aga atc gcc cca        1531
Leu Ile Val Ile Asp Ile Leu Gly Gly Arg Ser Val Arg Ile Ala Pro
            265                 270                 275 gac aca gca aac aaa gga atg atc tct ggc ctc tgt gga gat ctt aaa        1579
Asp Thr Ala Asn Lys Gly Met Ile Ser Gly Leu Cys Gly Asp Leu Lys
        280                 285                 290 atg atg gaa gat aca gac ttc act tca gat cca gaa caa ctc gct att        1627
Met Met Glu Asp Thr Asp Phe Thr Ser Asp Pro Glu Gln Leu Ala Ile
295                 300                 305 cag cct aag atc aac cag gag ttt gac ggt tgt cca ctc tat gga aat        1675
Gln Pro Lys Ile Asn Gln Glu Phe Asp Gly Cys Pro Leu Tyr Gly Asn
310                 315                 320                 325 cct gat gac gtt gca tac tgc aaa ggt ctt ctc gag ccg tac aag gac        1723
Pro Asp Asp Val Ala Tyr Cys Lys Gly Leu Leu Glu Pro Tyr Lys Asp
                330                 335                 340 agc tgc cgc aac ccc atc aac ttc tac tac tac acc atc tcc tgc gcc        1771
Ser Cys Arg Asn Pro Ile Asn Phe Tyr Tyr Tyr Thr Ile Ser Cys Ala
            345                 350                 355 ttc gcc cgc tgt atg ggt gga gac gag cga gcc tca cac gtg ctg ctt        1819
Phe Ala Arg Cys Met Gly Gly Asp Glu Arg Ala Ser His Val Leu Leu
        360                 365                 370 gac tac agg gag acg tgc gct gct ccc gaa act aga gga acc tgc gtt        1867
Asp Tyr Arg Glu Thr Cys Ala Ala Pro Glu Thr Arg Gly Thr Cys Val
375                 380                 385 ttg tct gga cat act ttc tac gat aca ttt gac aaa gca aga tat caa        1915
Leu Ser Gly His Thr Phe Tyr Asp Thr Phe Asp Lys Ala Arg Tyr Gln
390                 395                 400                 405 ttc cag ggt ccc tgc aag gag att ctt atg gcc gcc gac tgt ttc tgg        1963
Phe Gln Gly Pro Cys Lys Glu Ile Leu Met Ala Ala Asp Cys Phe Trp
                410                 415                 420 aac act tgg gat gtg aag gtt tca cac agg aat gtt gac tct tac act        2011
Asn Thr Trp Asp Val Lys Val Ser His Arg Asn Val Asp Ser Tyr Thr
            425                 430                 435 gaa gta gag aaa gta cga atc agg aaa caa tcg act gta gta gaa ctc        2059
Glu Val Glu Lys Val Arg Ile Arg Lys Gln Ser Thr Val Val Glu Leu
        440                 445                 450 att gtt gat gga aaa cag att ctg gtt gga gga gaa gcc gtg tcc gtc        2107
Ile Val Asp Gly Lys Gln Ile Leu Val Gly Gly Glu Ala Val Ser Val
455                 460                 465 ccg tac agc tct cag aac act tcc atc tac tgg caa gat ggt gac ata        2155
Pro Tyr Ser Ser Gln Asn Thr Ser Ile Tyr Trp Gln Asp Gly Asp Ile
470                 475                 480                 485 ctg act aca gcc atc cta cct gaa gct ctg gtg gtc aag ttc aac ttc        2203
Leu Thr Thr Ala Ile Leu Pro Glu Ala Leu Val Val Lys Phe Asn Phe
                490                 495                 500 aag caa ctg ctc gtc gta cat att aga gat cca ttc gat ggt aag act        2251
Lys Gln Leu Leu Val Val His Ile Arg Asp Pro Phe Asp Gly Lys Thr
            505                 510                 515 tgc ggt att tgc ggt aac tac aac cag gat ttc agt gat gat tct ttt        2299
```

```
                    Cys Gly Ile Cys Gly Asn Tyr Asn Gln Asp Phe Ser Asp Asp Ser Phe
                                    520                 525                 530 gat gct gaa gga gcc tgt gat ctg acc ccc aac cca ccg gga tgc acc           2347
Asp Ala Glu Gly Ala Cys Asp Leu Thr Pro Asn Pro Pro Gly Cys Thr
535                 540                 545 gaa gaa cag aaa cct gaa gct gaa cga ctc tgc aat agt ctc ttc gcc           2395
Glu Glu Gln Lys Pro Glu Ala Glu Arg Leu Cys Asn Ser Leu Phe Ala
550                 555                 560                 565 ggt caa agt gat ctt gat cag aaa tgt aac gtg tgc cac aag cct gac           2443
Gly Gln Ser Asp Leu Asp Gln Lys Cys Asn Val Cys His Lys Pro Asp
                570                 575                 580 cgt gtc gaa cga tgc atg tac gag tat tgc ctg agg gga caa cag ggt           2491
Arg Val Glu Arg Cys Met Tyr Glu Tyr Cys Leu Arg Gly Gln Gln Gly
            585                 590                 595 ttc tgt gac cac gca tgg gag ttc aag aaa gaa tgc tac ata aag cat          2539
Phe Cys Asp His Ala Trp Glu Phe Lys Lys Glu Cys Tyr Ile Lys His
                600                 605                 610 gga gac acc cta gaa gta cca gat gaa tgc aaa tag tctagagggc                2585
Gly Asp Thr Leu Glu Val Pro Asp Glu Cys Lys
615                 620 cgcatcatgt aattagttat gtcacgctta cattcacgcc ctcccccac atccgctcta         2645 accgaaaagg aaggagttag acaacctgaa gtctaggtcc ctatttattt ttttatagtt         2705
atgttagtat taagaacgtt atttatattt caaattttc ttttttttct gtacagacgc          2765
gtgtacgcat gtaacattat actgaaaacc ttgcttgaga aggttttggg acgctcgaag         2825
gctttaattt gcggccggta cccaattcgc cctatagtga gtcgtattac                    2875

<210> SEQ ID NO 8
<211> LENGTH: 30
<212> TYPE: DNA
<213> ORGANISM: Artificial Sequence
<220> FEATURE:
<223> OTHER INFORMATION: Synthetic oligonucleotide primer

<400> SEQUENCE: 8
atactactat tgccagcatt gctgctaaag                                              30

<210> SEQ ID NO 9
<211> LENGTH: 30
<212> TYPE: DNA
<213> ORGANISM: Artificial Sequence
<220> FEATURE:
<223> OTHER INFORMATION: Synthetic oligonucleotide primer

<400> SEQUENCE: 9
cacgtgtgag gctcgctcgt ctccacccat                                              30

<210> SEQ ID NO 10
<211> LENGTH: 25
<212> TYPE: DNA
<213> ORGANISM: Artificial Sequence
<220> FEATURE:
<223> OTHER INFORMATION: Synthetic oligonucleotide primer

<400> SEQUENCE: 10
gcttcagcct ctcttttctc gagag                                                   25

<210> SEQ ID NO 11
<211> LENGTH: 30
<212> TYPE: DNA
<213> ORGANISM: Artificial Sequence
<220> FEATURE:
<223> OTHER INFORMATION: Synthetic oligonucleotide primer
```

```
<400> SEQUENCE: 11
ttctcgagcc gtacaaggac agctgccgca                                30

<210> SEQ ID NO 12
<211> LENGTH: 30
<212> TYPE: DNA
<213> ORGANISM: Artificial Sequence
<220> FEATURE:
<223> OTHER INFORMATION: Synthetic oligonucleotide primer

<400> SEQUENCE: 12
tctctggcct ctgtggagat cttaaaatga                                30

<210> SEQ ID NO 13
<211> LENGTH: 30
<212> TYPE: DNA
<213> ORGANISM: Artificial Sequence
<220> FEATURE:
<223> OTHER INFORMATION: Synthetic oligonucleotide primer

<400> SEQUENCE: 13
aactccttcc ttttcggtta gagcggatgt                                30

<210> SEQ ID NO 14
<211> LENGTH: 25
<212> TYPE: DNA
<213> ORGANISM: Artificial Sequence
<220> FEATURE:
<223> OTHER INFORMATION: Synthetic oligonucleotide primer

<400> SEQUENCE: 14
tctagagggc cgcatcatgt aatta                                     25

<210> SEQ ID NO 15
<211> LENGTH: 30
<212> TYPE: DNA
<213> ORGANISM: Artificial Sequence
<220> FEATURE:
<223> OTHER INFORMATION: Synthetic oligonucleotide primer

<400> SEQUENCE: 15
tggacaaccg tcaaactcct ggttgatctt                                30

<210> SEQ ID NO 16
<211> LENGTH: 30
<212> TYPE: DNA
<213> ORGANISM: Artificial Sequence
<220> FEATURE:
<223> OTHER INFORMATION: Synthetic oligonucleotide primer

<400> SEQUENCE: 16
aaccctcact aaagggaaca aaagctggct                                30

<210> SEQ ID NO 17
<211> LENGTH: 21
<212> TYPE: DNA
<213> ORGANISM: Artificial Sequence
<220> FEATURE:
<223> OTHER INFORMATION: Synthetic oligonucleotide primer

<400> SEQUENCE: 17
gtacgggttg gcgatgatag g                                         21

<210> SEQ ID NO 18
<211> LENGTH: 45
```

```
<212> TYPE: DNA
<213> ORGANISM: Artificial Sequence
<220> FEATURE:
<223> OTHER INFORMATION: Synthetic oligonucleotide primer
<220> FEATURE:
<221> NAME/KEY: misc_feature
<222> LOCATION: (22)..(24)
<223> OTHER INFORMATION: n is a, c, g, or t

<400> SEQUENCE: 18
cctatcatcg ccaacccgta cnnnatcggc gaggtcacca tcgct         45

<210> SEQ ID NO 19
<211> LENGTH: 25
<212> TYPE: DNA
<213> ORGANISM: Artificial Sequence
<220> FEATURE:
<223> OTHER INFORMATION: Synthetic oligonucleotide primer

<400> SEQUENCE: 19
gtaatacgac tcactatagg gcgaa         25

<210> SEQ ID NO 20
<211> LENGTH: 636
<212> TYPE: PRT
<213> ORGANISM: Artificial Sequence
<220> FEATURE:
<223> OTHER INFORMATION: Synthetic fusion protein

<400> SEQUENCE: 20
```

```
Met Arg Phe Pro Ser Ile Phe Thr Ala Val Leu Phe Ala Ala Ser Ser
 1               5                  10                  15

Ala Leu Ala Ala Leu Val Asn Thr Thr Thr Glu Asp Glu Thr Ala Gln
            20                  25                  30

Ile Pro Ala Glu Ala Val Ile Gly Tyr Ser Asp Leu Glu Gly Asp Phe
        35                  40                  45

Asp Val Ala Val Leu Pro Phe Ser Asn Ser Thr Asn Asn Gly Leu Leu
    50                  55                  60

Phe Ile Asn Thr Thr Ile Ala Ser Ile Ala Ala Lys Glu Glu Gly Val
65                  70                  75                  80

Ser Leu Glu Lys Arg Glu Ala Glu Ala Gln Asp Cys Pro Tyr Glu Pro
                85                  90                  95

Asp Pro Pro Asn Thr Val Pro Thr Ser Cys Glu Ala Lys Glu Gly Glu
            100                 105                 110

Cys Ile Asp Ser Ser Cys Gly Thr Cys Thr Arg Asp Ile Leu Ser Asp
        115                 120                 125

Gly Leu Cys Glu Asn Lys Pro Gly Lys Thr Cys Cys Arg Met Cys Gln
    130                 135                 140

Tyr Val Ile Glu Cys Arg Val Glu Ala Ala Gly Trp Phe Arg Thr Phe
145                 150                 155                 160

Tyr Gly Lys Arg Phe Gln Phe Gln Glu Pro Gly Thr Tyr Val Leu Gly
                165                 170                 175

Gln Gly Thr Lys Gly Gly Asp Trp Lys Val Ser Ile Thr Leu Glu Asn
            180                 185                 190

Leu Asp Gly Thr Lys Gly Ala Val Leu Thr Lys Thr Arg Leu Glu Val
        195                 200                 205

Ala Gly Asp Ile Ile Asp Ile Ala Gln Ala Thr Glu Asn Pro Ile Thr
    210                 215                 220

Val Asn Gly Gly Ala Asp Pro Ile Ile Ala Asn Pro Tyr Thr Ile Gly
225                 230                 235                 240
```

```
Glu Val Thr Ile Ala Val Val Glu Met Pro Gly Phe Asn Ile Thr Val
                245                 250                 255

Ile Glu Phe Phe Lys Leu Ile Val Ile Asp Ile Leu Gly Gly Arg Ser
            260                 265                 270

Val Arg Ile Ala Pro Asp Thr Ala Asn Lys Gly Met Ile Ser Gly Leu
        275                 280                 285

Cys Gly Asp Leu Lys Met Met Glu Asp Thr Asp Phe Thr Ser Asp Pro
    290                 295                 300

Glu Gln Leu Ala Ile Gln Pro Lys Ile Asn Gln Glu Phe Asp Gly Cys
305                 310                 315                 320

Pro Leu Tyr Gly Asn Pro Asp Asp Val Ala Tyr Cys Lys Gly Leu Leu
                325                 330                 335

Glu Pro Tyr Lys Asp Ser Cys Arg Asn Pro Ile Asn Phe Tyr Tyr Tyr
            340                 345                 350

Thr Ile Ser Cys Ala Phe Ala Arg Cys Met Gly Gly Asp Glu Arg Ala
        355                 360                 365

Ser His Val Leu Leu Asp Tyr Arg Glu Thr Cys Ala Ala Pro Glu Thr
    370                 375                 380

Arg Gly Thr Cys Val Leu Ser Gly His Thr Phe Tyr Asp Thr Phe Asp
385                 390                 395                 400

Lys Ala Arg Tyr Gln Phe Gln Gly Pro Cys Lys Glu Ile Leu Met Ala
                405                 410                 415

Ala Asp Cys Phe Trp Asn Thr Trp Asp Val Lys Val Ser His Arg Asn
            420                 425                 430

Val Asp Ser Tyr Thr Glu Val Glu Lys Val Arg Ile Arg Lys Gln Ser
        435                 440                 445

Thr Val Val Glu Leu Ile Val Asp Gly Lys Gln Ile Leu Val Gly Gly
    450                 455                 460

Glu Ala Val Ser Val Pro Tyr Ser Ser Gln Asn Thr Ser Ile Tyr Trp
465                 470                 475                 480

Gln Asp Gly Asp Ile Leu Thr Thr Ala Ile Leu Pro Glu Ala Leu Val
                485                 490                 495

Val Lys Phe Asn Phe Lys Gln Leu Leu Val Val His Ile Arg Asp Pro
            500                 505                 510

Phe Asp Gly Lys Thr Cys Gly Ile Cys Gly Asn Tyr Asn Gln Asp Phe
        515                 520                 525

Ser Asp Asp Ser Phe Asp Ala Glu Gly Ala Cys Asp Leu Thr Pro Asn
    530                 535                 540

Pro Pro Gly Cys Thr Glu Gln Lys Pro Glu Ala Glu Arg Leu Cys
545                 550                 555                 560

Asn Ser Leu Phe Ala Gly Gln Ser Asp Leu Asp Gln Lys Cys Asn Val
                565                 570                 575

Cys His Lys Pro Asp Arg Val Glu Arg Cys Met Tyr Glu Tyr Cys Leu
            580                 585                 590

Arg Gly Gln Gln Gly Phe Cys Asp His Ala Trp Glu Phe Lys Lys Glu
        595                 600                 605

Cys Tyr Ile Lys His Gly Asp Thr Leu Glu Val Pro Asp Glu Cys Lys
    610                 615                 620

Gly Ser Gly Ser Gly Ser His His His His His
625                 630                 635

<210> SEQ ID NO 21
<211> LENGTH: 45
<212> TYPE: DNA
<213> ORGANISM: Artificial Sequence
```

-continued

```
<220> FEATURE:
<223> OTHER INFORMATION: Synthetic oligonucleotide primer

<400> SEQUENCE: 21
caccaccatc accaccatta gtctagaggg ccgcatcatg taatt         45

<210> SEQ ID NO 22
<211> LENGTH: 45
<212> TYPE: DNA
<213> ORGANISM: Artificial Sequence
<220> FEATURE:
<223> OTHER INFORMATION: Synthetic oligonucleotide primer

<400> SEQUENCE: 22
agaaccagaa ccagaacctt tgcattcatc tggtacttct aggt          45

<210> SEQ ID NO 23
<211> LENGTH: 2911
<212> TYPE: DNA
<213> ORGANISM: Artificial Sequence
<220> FEATURE:
<223> OTHER INFORMATION: Partial nucleotide sequence of plasmid
      pCLuRA-TDH3 [alphaP21L,-(GS)3H6]
<220> FEATURE:
<221> NAME/KEY: CDS
<222> LOCATION: (701)..(2611)

<400> SEQUENCE: 23
```

| | |
|---|---:|
| aaccctcact aaagggaaca aaagctggct agaactagtg gatcccgagt ttatcattat | 60 |
| caatactgcc atttcaaaga atacgtaaat aattaatagt agtgattttc ctaactttat | 120 |
| ttagtcaaaa aattagcctt ttaattctgc tgtaacccgt acatgcccaa atagggggc | 180 |
| gggttacaca gaatatataa catcgtaggt gtctgggtga acagtttatt cctggcatcc | 240 |
| actaaatata atggagcccg cttttaagc tggcatccag aaaaaaaaag aatcccagca | 300 |
| ccaaaatatt gttttcttca ccaaccatca gttcataggt ccattctctt agcgcaacta | 360 |
| cagagaacag gggcacaaac aggcaaaaaa cgggcacaac ctcaatggag tgatgcaacc | 420 |
| tgcctggagt aaatgatgac acaaggcaat tgacccacgc atgtatctat ctcattttct | 480 |
| tacaccttct attaccttct gctctctctg atttggaaaa agctgaaaaa aaaggttgaa | 540 |
| accagttccc tgaaattatt ccctacttg actaataagt atataaagac ggtaggtatt | 600 |
| gattgtaatt ctgtaaatct atttcttaaa cttcttaaat tctacttta tagttagtct | 660 |

| | | | | | | |
|---|---|---|---|---|---|---:|
| tttttttagt tttaaacac caagaactta gtttcgaggg | atg | aga | ttt | cct | tca | 715 |
| | Met | Arg | Phe | Pro | Ser | |
| | 1 | | | | 5 | |

| | | | | | | | | | | | | |
|---|---|---|---|---|---|---|---|---|---|---|---|---:|
| att | ttt | act | gct | gtt | tta | ttc | gca | gca | tcc | tcc | gca | tta | gct | gct | cta | 763 |
| Ile | Phe | Thr | Ala | Val | Leu | Phe | Ala | Ala | Ser | Ser | Ala | Leu | Ala | Ala | Leu | |
| | | | 10 | | | | | 15 | | | | | 20 | | | |

| | | | | | | | | | | | | |
|---|---|---|---|---|---|---|---|---|---|---|---|---:|
| gtc | aac | act | aca | aca | gaa | gat | gaa | acg | gca | caa | att | ccg | gct | gaa | gct | 811 |
| Val | Asn | Thr | Thr | Thr | Glu | Asp | Glu | Thr | Ala | Gln | Ile | Pro | Ala | Glu | Ala | |
| | | 25 | | | | | 30 | | | | | 35 | | | | |

| | | | | | | | | | | | | |
|---|---|---|---|---|---|---|---|---|---|---|---|---:|
| gtc | atc | ggt | tac | tca | gat | tta | gaa | ggg | gat | ttc | gat | gtt | gct | gtt | ttg | 859 |
| Val | Ile | Gly | Tyr | Ser | Asp | Leu | Glu | Gly | Asp | Phe | Asp | Val | Ala | Val | Leu | |
| | 40 | | | | | 45 | | | | | 50 | | | | | |

| | | | | | | | | | | | | |
|---|---|---|---|---|---|---|---|---|---|---|---|---:|
| cca | ttt | tcc | aac | agc | aca | aat | aac | ggg | tta | ttg | ttt | ata | aat | act | act | 907 |
| Pro | Phe | Ser | Asn | Ser | Thr | Asn | Asn | Gly | Leu | Leu | Phe | Ile | Asn | Thr | Thr | |
| 55 | | | | | 60 | | | | | 65 | | | | | | |

| | | | | | | | | | | | | |
|---|---|---|---|---|---|---|---|---|---|---|---|---:|
| att | gcc | agc | att | gct | gct | aaa | gaa | gaa | ggg | gta | tct | ctc | gag | aaa | aga | 955 |
| Ile | Ala | Ser | Ile | Ala | Ala | Lys | Glu | Glu | Gly | Val | Ser | Leu | Glu | Lys | Arg | |
| 70 | | | | | 75 | | | | | 80 | | | | | 85 | |

| | | | | | | | | | | |
|---|---|---|---|---|---|---|---|---|---|---:|
| gag | gct | gaa | gct | cag | gac | tgt | cct | tac | gaa | cct | gat | cca | cca | aac | aca | 1003 |

-continued

| | | |
|---|---|---|
| Glu Ala Glu Ala Gln Asp Cys Pro Tyr Glu Pro Asp Pro Asn Thr<br>          90                  95                  100 | | |
| gtt cca act tcc tgt gaa gct aaa gaa gga gaa tgt att gat agc agc<br>Val Pro Thr Ser Cys Glu Ala Lys Glu Gly Glu Cys Ile Asp Ser Ser<br>                105                110                115 | 1051 |
| tgt ggc acc tgc acg aga gac ata cta tca gat gga ctg tgt gaa aat<br>Cys Gly Thr Cys Thr Arg Asp Ile Leu Ser Asp Gly Leu Cys Glu Asn<br>        120                125                130 | 1099 |
| aaa cca gga aaa aca tgt tgc cga atg tgt cag tat gta att gaa tgc<br>Lys Pro Gly Lys Thr Cys Cys Arg Met Cys Gln Tyr Val Ile Glu Cys<br>135                  140                145 | 1147 |
| aga gta gag gct gca gga tgg ttt aga aca ttc tat gga aag aga ttc<br>Arg Val Glu Ala Ala Gly Trp Phe Arg Thr Phe Tyr Gly Lys Arg Phe<br>150                  155                160              165 | 1195 |
| cag ttc cag gaa cct ggt aca tac gtg ttg ggt caa gga acc aag ggc<br>Gln Phe Gln Glu Pro Gly Thr Tyr Val Leu Gly Gln Gly Thr Lys Gly<br>                170                175              180 | 1243 |
| ggc gac tgg aag gtg tcc atc acc ctg gag aac ctg gat gga acc aag<br>Gly Asp Trp Lys Val Ser Ile Thr Leu Glu Asn Leu Asp Gly Thr Lys<br>                    185                190              195 | 1291 |
| ggg gct gtg ctg acc aag aca aga ctg gaa gtg gct gga gac atc att<br>Gly Ala Val Leu Thr Lys Thr Arg Leu Glu Val Ala Gly Asp Ile Ile<br>        200                205                210 | 1339 |
| gac atc gct caa gct act gag aat ccc atc act gta aac ggt gga gct<br>Asp Ile Ala Gln Ala Thr Glu Asn Pro Ile Thr Val Asn Gly Gly Ala<br>215                  220                225 | 1387 |
| gac cct atc atc gcc aac ccg tac acc atc ggc gag gtc acc atc gct<br>Asp Pro Ile Ile Ala Asn Pro Tyr Thr Ile Gly Glu Val Thr Ile Ala<br>230                  235                240              245 | 1435 |
| gtt gtt gag atg cca ggc ttc aac atc acc gtc ata gaa ttc ttc aaa<br>Val Val Glu Met Pro Gly Phe Asn Ile Thr Val Ile Glu Phe Phe Lys<br>                    250                255              260 | 1483 |
| ctg atc gtg atc gac atc ctc gga gga aga tct gta aga atc gcc cca<br>Leu Ile Val Ile Asp Ile Leu Gly Gly Arg Ser Val Arg Ile Ala Pro<br>                265                270              275 | 1531 |
| gac aca gca aac aaa gga atg atc tct ggc ctc tgt gga gat ctt aaa<br>Asp Thr Ala Asn Lys Gly Met Ile Ser Gly Leu Cys Gly Asp Leu Lys<br>        280                285                290 | 1579 |
| atg atg gaa gat aca gac ttc act tca gat cca gaa caa ctc gct att<br>Met Met Glu Asp Thr Asp Phe Thr Ser Asp Pro Glu Gln Leu Ala Ile<br>295                  300                305 | 1627 |
| cag cct aag atc aac cag gag ttt gac ggt tgt cca ctc tat gga aat<br>Gln Pro Lys Ile Asn Gln Glu Phe Asp Gly Cys Pro Leu Tyr Gly Asn<br>310                  315                320              325 | 1675 |
| cct gat gac gtt gca tac tgc aaa ggt ctt ctc gag ccg tac aag gac<br>Pro Asp Asp Val Ala Tyr Cys Lys Gly Leu Leu Glu Pro Tyr Lys Asp<br>                    330                335              340 | 1723 |
| agc tgc cgc aac ccc atc aac ttc tac tac tac acc atc tcc tgc gcc<br>Ser Cys Arg Asn Pro Ile Asn Phe Tyr Tyr Tyr Thr Ile Ser Cys Ala<br>                345                350              355 | 1771 |
| ttc gcc cgc tgt atg ggt gga gac gag cga gcc tca cac gtg ctg ctt<br>Phe Ala Arg Cys Met Gly Gly Asp Glu Arg Ala Ser His Val Leu Leu<br>        360                365                370 | 1819 |
| gac tac agg gag acg tgc gct gct ccc gaa act aga gga acc tgc gtt<br>Asp Tyr Arg Glu Thr Cys Ala Ala Pro Glu Thr Arg Gly Thr Cys Val<br>375                  380                385 | 1867 |
| ttg tct gga cat act ttc tac gat aca ttt gac aaa gca aga tat caa<br>Leu Ser Gly His Thr Phe Tyr Asp Thr Phe Asp Lys Ala Arg Tyr Gln<br>390                  395                400              405 | 1915 |
| ttc cag ggt ccc tgc aag gag att ctt atg gcc gcc gac tgt ttc tgg | 1963 |

```
                Phe Gln Gly Pro Cys Lys Glu Ile Leu Met Ala Ala Asp Cys Phe Trp
                                410                 415                 420 aac act tgg gat gtg aag gtt tca cac agg aat gtt gac tct tac act           2011
Asn Thr Trp Asp Val Lys Val Ser His Arg Asn Val Asp Ser Tyr Thr
                425                 430                 435 gaa gta gag aaa gta cga atc agg aaa caa tcg act gta gta gaa ctc           2059
Glu Val Glu Lys Val Arg Ile Arg Lys Gln Ser Thr Val Val Glu Leu
            440                 445                 450 att gtt gat gga aaa cag att ctg gtt gga gga gaa gcc gtg tcc gtc           2107
Ile Val Asp Gly Lys Gln Ile Leu Val Gly Gly Glu Ala Val Ser Val
            455                 460                 465 ccg tac agc tct cag aac act tcc atc tac tgg caa gat ggt gac ata           2155
Pro Tyr Ser Ser Gln Asn Thr Ser Ile Tyr Trp Gln Asp Gly Asp Ile
470                 475                 480                 485 ctg act aca gcc atc cta cct gaa gct ctg gtg gtc aag ttc aac ttc           2203
Leu Thr Thr Ala Ile Leu Pro Glu Ala Leu Val Val Lys Phe Asn Phe
                490                 495                 500 aag caa ctg ctc gtc gta cat att aga gat cca ttc gat ggt aag act           2251
Lys Gln Leu Leu Val Val His Ile Arg Asp Pro Phe Asp Gly Lys Thr
                505                 510                 515 tgc ggt att tgc ggt aac tac aac cag gat ttc agt gat gat tct ttt           2299
Cys Gly Ile Cys Gly Asn Tyr Asn Gln Asp Phe Ser Asp Asp Ser Phe
                520                 525                 530 gat gct gaa gga gcc tgt gat ctg acc ccc aac cca ccg gga tgc acc           2347
Asp Ala Glu Gly Ala Cys Asp Leu Thr Pro Asn Pro Pro Gly Cys Thr
535                 540                 545 gaa gaa cag aaa cct gaa gct gaa cga ctc tgc aat agt ctc ttc gcc           2395
Glu Glu Gln Lys Pro Glu Ala Glu Arg Leu Cys Asn Ser Leu Phe Ala
550                 555                 560                 565 ggt caa agt gat ctt gat cag aaa tgt aac gtg tgc cac aag cct gac           2443
Gly Gln Ser Asp Leu Asp Gln Lys Cys Asn Val Cys His Lys Pro Asp
                570                 575                 580 cgt gtc gaa cga tgc atg tac gag tat tgc ctg agg gga caa cag ggt           2491
Arg Val Glu Arg Cys Met Tyr Glu Tyr Cys Leu Arg Gly Gln Gln Gly
                585                 590                 595 ttc tgt gac cac gca tgg gag ttc aag aaa gaa tgc tac ata aag cat           2539
Phe Cys Asp His Ala Trp Glu Phe Lys Lys Glu Cys Tyr Ile Lys His
                600                 605                 610 gga gac acc cta gaa gta cca gat gaa tgc aaa ggt tct ggt tct ggt           2587
Gly Asp Thr Leu Glu Val Pro Asp Glu Cys Lys Gly Ser Gly Ser Gly
615                 620                 625 tct cac cac cat cac cac cat tag tctagagggc cgcatcatgt aattagttat          2641
Ser His His His His His His
630                 635 gtcacgctta cattcacgcc ctccccccac atccgctcta accgaaaagg aaggagttag         2701
acaacctgaa gtctaggtcc ctatttattt ttttatagtt atgttagtat taagaacgtt         2761
atttatattt caaattttc tttttttct gtacagacgc gtgtacgcat gtaacattat           2821
actgaaaacc ttgcttgaga aggttttggg acgctcgaag gctttaattt gcggccggta         2881
cccaattcgc cctatagtga gtcgtattac                                          2911
```

<210> SEQ ID NO 24
<211> LENGTH: 53
<212> TYPE: DNA
<213> ORGANISM: Artificial Sequence
<220> FEATURE:
<223> OTHER INFORMATION: Synthetic oligonucleotide primer
<220> FEATURE:
<221> NAME/KEY: misc_feature
<222> LOCATION: (26)..(28)
<223> OTHER INFORMATION: n is a, c, g, or t

```
<400> SEQUENCE: 24
tgaagtagag aaagtacgaa tcaggnnnca atcgactgta gtagtagaac tca         53

<210> SEQ ID NO 25
<211> LENGTH: 25
<212> TYPE: DNA
<213> ORGANISM: Artificial Sequence
<220> FEATURE:
<223> OTHER INFORMATION: Synthetic oligonucleotide primer

<400> SEQUENCE: 25
cctgattcgt actttctcta cttca                                        25

<210> SEQ ID NO 26
<211> LENGTH: 25
<212> TYPE: DNA
<213> ORGANISM: Artificial Sequence
<220> FEATURE:
<223> OTHER INFORMATION: Synthetic oligonucleotide primer

<400> SEQUENCE: 26
tttcaatcga ctgtagtaga actca                                        25

<210> SEQ ID NO 27
<211> LENGTH: 25
<212> TYPE: DNA
<213> ORGANISM: Artificial Sequence
<220> FEATURE:
<223> OTHER INFORMATION: Synthetic oligonucleotide primer

<400> SEQUENCE: 27
catcaatcga ctgtagtaga actca                                        25

<210> SEQ ID NO 28
<211> LENGTH: 25
<212> TYPE: DNA
<213> ORGANISM: Artificial Sequence
<220> FEATURE:
<223> OTHER INFORMATION: Synthetic oligonucleotide primer

<400> SEQUENCE: 28
ccacaatcga ctgtagtaga actca                                        25

<210> SEQ ID NO 29
<211> LENGTH: 21
<212> TYPE: DNA
<213> ORGANISM: Artificial Sequence
<220> FEATURE:
<223> OTHER INFORMATION: Synthetic oligonucleotide primer

<400> SEQUENCE: 29
ctgagagctg tacgggacgg a                                            21

<210> SEQ ID NO 30
<211> LENGTH: 45
<212> TYPE: DNA
<213> ORGANISM: Artificial Sequence
<220> FEATURE:
<223> OTHER INFORMATION: Synthetic oligonucleotide primer
<220> FEATURE:
<221> NAME/KEY: misc_feature
<222> LOCATION: (22)..(24)
<223> OTHER INFORMATION: n is a, c, g, or t

<400> SEQUENCE: 30
tccgtcccgt acagctctca gnnnacttcc atctactggc aagat                  45
```

<210> SEQ ID NO 31
<211> LENGTH: 21
<212> TYPE: DNA
<213> ORGANISM: Artificial Sequence
<220> FEATURE:
<223> OTHER INFORMATION: Synthetic oligonucleotide primer

<400> SEQUENCE: 31
gttctgagag ctgtacggga c                                      21

<210> SEQ ID NO 32
<211> LENGTH: 45
<212> TYPE: DNA
<213> ORGANISM: Artificial Sequence
<220> FEATURE:
<223> OTHER INFORMATION: Synthetic oligonucleotide primer
<220> FEATURE:
<221> NAME/KEY: misc_feature
<222> LOCATION: (22)..(24)
<223> OTHER INFORMATION: n is a, c, g, or t

<400> SEQUENCE: 32
gtcccgtaca gctctcagaa cnnntccatc tactggcaag atggt            45

<210> SEQ ID NO 33
<211> LENGTH: 21
<212> TYPE: DNA
<213> ORGANISM: Artificial Sequence
<220> FEATURE:
<223> OTHER INFORMATION: Synthetic oligonucleotide primer

<400> SEQUENCE: 33
agtgttctga gagctgtacg g                                      21

<210> SEQ ID NO 34
<211> LENGTH: 45
<212> TYPE: DNA
<213> ORGANISM: Artificial Sequence
<220> FEATURE:
<223> OTHER INFORMATION: Synthetic oligonucleotide primer
<220> FEATURE:
<221> NAME/KEY: misc_feature
<222> LOCATION: (22)..(24)
<223> OTHER INFORMATION: n is a, c, g, or t

<400> SEQUENCE: 34
ccgtacagct ctcagaacac tnnnatctac tggcaagatg gtgac            45

<210> SEQ ID NO 35
<211> LENGTH: 21
<212> TYPE: DNA
<213> ORGANISM: Artificial Sequence
<220> FEATURE:
<223> OTHER INFORMATION: Synthetic oligonucleotide primer

<400> SEQUENCE: 35
ggaagtgttc tgagagctgt a                                      21

<210> SEQ ID NO 36
<211> LENGTH: 45
<212> TYPE: DNA
<213> ORGANISM: Artificial Sequence
<220> FEATURE:
<223> OTHER INFORMATION: Synthetic oligonucleotide primer
<220> FEATURE:
<221> NAME/KEY: misc_feature
<222> LOCATION: (22)..(24)
<223> OTHER INFORMATION: n is a, c, g, or t

<400> SEQUENCE: 36
tacagctctc agaacacttc cnnntactgg caagatggtg acata            45

<210> SEQ ID NO 37
<211> LENGTH: 21
<212> TYPE: DNA
<213> ORGANISM: Artificial Sequence
<220> FEATURE:
<223> OTHER INFORMATION: Synthetic oligonucleotide primer

<400> SEQUENCE: 37
gatgtcgatc acgatcagtt t                                      21

<210> SEQ ID NO 38
<211> LENGTH: 45
<212> TYPE: DNA
<213> ORGANISM: Artificial Sequence
<220> FEATURE:
<223> OTHER INFORMATION: Synthetic oligonucleotide primer
<220> FEATURE:
<221> NAME/KEY: misc_feature
<222> LOCATION: (22)..(24)
<223> OTHER INFORMATION: n is a, c, g, or t

<400> SEQUENCE: 38
aaactgatcg tgatcgacat cnnnggagga agatctgtaa gaatc            45

<210> SEQ ID NO 39
<211> LENGTH: 30
<212> TYPE: DNA
<213> ORGANISM: Artificial Sequence
<220> FEATURE:
<223> OTHER INFORMATION: Synthetic oligonucleotide primer

<400> SEQUENCE: 39
cacgatcagt ttgaagaatt ctatgacggt                             30

<210> SEQ ID NO 40
<211> LENGTH: 30
<212> TYPE: DNA
<213> ORGANISM: Artificial Sequence
<220> FEATURE:
<223> OTHER INFORMATION: Synthetic oligonucleotide primer

<400> SEQUENCE: 40
accgtcatag aattcttcaa actgatcgtg                             30

<210> SEQ ID NO 41
<211> LENGTH: 24
<212> TYPE: DNA
<213> ORGANISM: Artificial Sequence
<220> FEATURE:
<223> OTHER INFORMATION: Synthetic oligonucleotide primer

<400> SEQUENCE: 41
atgtatctat ctcattttct taca                                   24

<210> SEQ ID NO 42
<211> LENGTH: 27
<212> TYPE: DNA
<213> ORGANISM: Artificial Sequence
<220> FEATURE:
<223> OTHER INFORMATION: Synthetic oligonucleotide primer

<400> SEQUENCE: 42 cagcttttc caaatcagag agagcag                                 27

<210> SEQ ID NO 43
<211> LENGTH: 24
<212> TYPE: DNA
<213> ORGANISM: Artificial Sequence
<220> FEATURE:
<223> OTHER INFORMATION: Synthetic oligonucleotide primer

<400> SEQUENCE: 43
caaccagaat ctgttttcca tcaa                                          24

<210> SEQ ID NO 44
<211> LENGTH: 24
<212> TYPE: DNA
<213> ORGANISM: Artificial Sequence
<220> FEATURE:
<223> OTHER INFORMATION: Synthetic oligonucleotide primer

<400> SEQUENCE: 44
ttgatggaaa acagattctg gttg                                          24

<210> SEQ ID NO 45
<211> LENGTH: 21
<212> TYPE: DNA
<213> ORGANISM: Artificial Sequence
<220> FEATURE:
<223> OTHER INFORMATION: Synthetic oligonucleotide primer

<400> SEQUENCE: 45
agagctgtac gggacggaca c                                             21

<210> SEQ ID NO 46
<211> LENGTH: 48
<212> TYPE: DNA
<213> ORGANISM: Artificial Sequence
<220> FEATURE:
<223> OTHER INFORMATION: Synthetic oligonucleotide primer

<400> SEQUENCE: 46
gtgtccgtcc cgtacagctc tcccgggact tccatctact ggcaagat                48

<210> SEQ ID NO 47
<211> LENGTH: 51
<212> TYPE: DNA
<213> ORGANISM: Artificial Sequence
<220> FEATURE:
<223> OTHER INFORMATION: Synthetic oligonucleotide primer

<400> SEQUENCE: 47
gtgtccgtcc cgtacagctc tcccaacatc tccatctact ggcaagatgg t            51

<210> SEQ ID NO 48
<211> LENGTH: 48
<212> TYPE: DNA
<213> ORGANISM: Artificial Sequence
<220> FEATURE:
<223> OTHER INFORMATION: Synthetic oligonucleotide primer

<400> SEQUENCE: 48
tccgtcccgt acagctctca ggggatctcc atctactggc aagatggt                48

<210> SEQ ID NO 49
<211> LENGTH: 51
<212> TYPE: DNA
<213> ORGANISM: Artificial Sequence
<220> FEATURE:
<223> OTHER INFORMATION: Synthetic oligonucleotide primer

```
<400> SEQUENCE: 49
gtgtccgtcc cgtacagctc tcccgggatc tccatctact ggcaagatgg t          51

<210> SEQ ID NO 50
<211> LENGTH: 51
<212> TYPE: DNA
<213> ORGANISM: Artificial Sequence
<220> FEATURE:
<223> OTHER INFORMATION: Synthetic oligonucleotide primer

<400> SEQUENCE: 50
gtgtccgtcc cgtacagctc tcccgggatg tccatctact ggcaagatgg t          51

<210> SEQ ID NO 51
<211> LENGTH: 54
<212> TYPE: DNA
<213> ORGANISM: Artificial Sequence
<220> FEATURE:
<223> OTHER INFORMATION: Synthetic oligonucleotide primer

<400> SEQUENCE: 51
gtgtccgtcc cgtacagctc tcccgggatg ctcatctact ggcaagatgg tgac       54

<210> SEQ ID NO 52
<211> LENGTH: 57
<212> TYPE: DNA
<213> ORGANISM: Artificial Sequence
<220> FEATURE:
<223> OTHER INFORMATION: Synthetic oligonucleotide primer

<400> SEQUENCE: 52
gtgtccgtcc cgtacagctc tcccgggatg ctcgcctact ggcaagatgg tgacata    57

<210> SEQ ID NO 53
<211> LENGTH: 25
<212> TYPE: DNA
<213> ORGANISM: Artificial Sequence
<220> FEATURE:
<223> OTHER INFORMATION: Synthetic oligonucleotide primer

<400> SEQUENCE: 53
ctagggtgtc tccatgcttt atgta                                        25

<210> SEQ ID NO 54
<211> LENGTH: 24
<212> TYPE: DNA
<213> ORGANISM: Artificial Sequence
<220> FEATURE:
<223> OTHER INFORMATION: Synthetic oligonucleotide primerr

<400> SEQUENCE: 54
aagctgaacg actctgcaat agtc                                         24

<210> SEQ ID NO 55
<211> LENGTH: 21
<212> TYPE: DNA
<213> ORGANISM: Artificial Sequence
<220> FEATURE:
<223> OTHER INFORMATION: Synthetic oligonucleotide primer

<400> SEQUENCE: 55
gtacggctcg agaagacctt t                                            21
```